United States Patent
Merighi et al.

(10) Patent No.: US 10,487,346 B2
(45) Date of Patent: *Nov. 26, 2019

(54) BIOSYNTHESIS OF HUMAN MILK OLIGOSACCHARIDES IN ENGINEERED BACTERIA

(71) Applicant: Glycosyn LLC, Woburn, MA (US)

(72) Inventors: Massimo Merighi, Somerville, MA (US); John M. McCoy, Reading, MA (US); Matthew Ian Heidtman, Brighton, MA (US)

(73) Assignee: Glycosyn LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,349

(22) Filed: May 15, 2018

(65) Prior Publication Data

US 2018/0251771 A1    Sep. 6, 2018

Related U.S. Application Data

(60) Continuation of application No. 15/442,131, filed on Feb. 24, 2017, which is a continuation of application No. 14/033,664, filed on Sep. 23, 2013, now Pat. No. 9,587,241, which is a division of application No. 13/398,526, filed on Feb. 16, 2012, now Pat. No. 9,453,230.

(60) Provisional application No. 61/443,470, filed on Feb. 16, 2011.

(51) Int. Cl.

| | |
|---|---|
| C12P 19/18 | (2006.01) |
| C12P 19/26 | (2006.01) |
| C12P 19/00 | (2006.01) |
| C12N 9/00 | (2006.01) |
| C12N 9/10 | (2006.01) |
| C12N 9/38 | (2006.01) |
| C07H 3/06 | (2006.01) |
| C07H 13/04 | (2006.01) |
| C12N 15/70 | (2006.01) |
| C12N 9/14 | (2006.01) |

(52) U.S. Cl.
CPC .............. *C12P 19/00* (2013.01); *C07H 3/06* (2013.01); *C07H 13/04* (2013.01); *C12N 9/00* (2013.01); *C12N 9/1051* (2013.01); *C12N 9/14* (2013.01); *C12N 9/2471* (2013.01); *C12N 15/70* (2013.01); *C12P 19/18* (2013.01); *C12P 19/26* (2013.01); *C12Y 204/01* (2013.01); *C12Y 204/01065* (2013.01); *C12Y 302/01023* (2013.01); *C12Y 306/03018* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,270,181 A | 12/1993 | McCoy et al. |
| 7,268,221 B2 | 9/2007 | Caimi et al. |
| 7,521,212 B1 † | 4/2009 | Samain |
| 7,820,422 B2 | 10/2010 | Samain |
| 9,453,230 B2 | 9/2016 | Merighi et al. |
| 9,587,241 B2 | 3/2017 | Merighi et al. |
| 9,970,018 B2 | 5/2018 | Merighi et al. |
| 2008/0145899 A1 | 6/2008 | Johnson et al. |
| 2017/0226547 A1 | 8/2017 | Merighi et al. |
| 2017/0268010 A1 | 9/2017 | Merighi et al. |
| 2018/0251771 A1 † | 9/2018 | Merighi |

FOREIGN PATENT DOCUMENTS

| | | |
|---|---|---|
| JP | 2013535962 A | 9/2013 |
| JP | 2014504874 A | 2/2014 |
| JP | 2017093453 A | 6/2017 |
| WO | WO-2006034225 A2 | 3/2006 |
| WO | WO-2010070104 A1 | 6/2010 |
| WO | WO-2012007481 A2 | 1/2012 |
| WO | WO-2012097950 A1 | 7/2012 |
| WO | 2012112777 A2 | 8/2012 |
| WO | 2015150328 A1 | 10/2015 |

OTHER PUBLICATIONS

Albermann et al. "Synthesis of the Milk Oligosaccharide 2'-Fucosyllactose Using Recombinant Bacterial Enzymes." *Carbohydr. Res.* 334.2(2001):97-103.

Amonsen et al. "Human Parainfluenza Viruses hPIV1 and hPIV3 Bind Oligosaccharides with a 2-3-Linked Sialic Acids that are Distinct from those Bound by H5 Avian Influenza Virus Hemagglutinin." *J. Virol.* 81.15(2007):8341-8345.

Bao et al. "Capillary Electrophoresis of Acidic Oligosaccharides from Human Milk." *Electrophoresis.* 29.12(2008):2508-2515.

Bao et al. "Simultaneous Quantification of Sialyloligosaccharides from Human Milk by Capillary Electrophoresis." *Anal. Biochem.* 370(2007):206-214.

Belfort et al. "Characterization of the *Escherichia coli* thyA Gene and its Amplified Thymidylate Synthetase Product." *PNAS.* 80.7(1983):1858-1861.

Bettler et al. "The Living Factory: In vivo Production of N-Acetyllactosamine Containing Carbohydrates in *E. coli*." *Glycoconj. J.* 16.3(1999):205-212.

Bode et al. "Inhibition of Monocyte, Lymphocyte, and Neutrophil Adhesion to Endothelial Cells by Human Milk Oligosaccharides." *Thrombosis Haemostasis.* 92.6(2004):1402-1410.

Charlwood et al. "A Detailed Analysis of Neutral and Acidic Carbohydrates in Human Milk." *Anal. Biochem.* 273.2(1999):261-277.

(Continued)

*Primary Examiner* — Rebecca E Prouty

(74) *Attorney, Agent, or Firm* — Mintz Levin Cohn Ferris Glovsky and Popeo, P.C.; Ingrid A. Beattie

(57) ABSTRACT

The invention provides compositions and methods for engineering bacteria to produce fucosylated oligosaccharides, and the use thereof in the prevention or treatment of infection.

24 Claims, 24 Drawing Sheets

Specification includes a Sequence Listing.

(56) References Cited

OTHER PUBLICATIONS

Chaturvedi et al. "Fucosylated Human Milk Oligosaccharides Vary Between Individuals and Over the Course of Lactation." Glycobiol. 11.5(2001):365-372.
Chaturvedi et al. "Survival of Human Milk Oligosaccharides in the Intestine of Infants." Adv. Exp. Med. Biol. 501(2001):315-323.
Couceiro et al. "Influenza Virus Strains Selectively Recognize Sialyloligosaccharides on Human Respiratory Epithelium; The Role of the Host Cell in Selection of Hemagglutinin Receptor Specificity." Virus Res. 29.2(1993):155-165.
Court et al. "Genetic Engineering Using Homologous Recombination." Annu. Rev. Genet. 36(2002):361-388.
Coyne et al., "Bacteroides fragilis NCTC9343 produces at least three distinct capsular polysaccharides: cloning, characterization, and reassignment of polysaccharide B and C biosynthesis loci," Infect Immun. Nov. 2000; 68(11): 6176-81.
Crout et al. "Glycosidases and Glycosyl Transferases in Glycoside and Oligosaccharide Synthesis." Curr. Opin. Chem. Biol. 2.1(1998):98-111.
Danchin. "Cells need safety valves", Bioessays, 31:769-773 (2009).
De Vries et al. "Fucosyltransferases: Structure/Function Studies." Glycobiol. 11.10(2001):119R-128R.
Dumon et al. "In vivo fucosylation of lacto-N-neotetraose and lacto-N-neohexaose by heterologous expression of Helicobacter pylori alpha-1,3 fucosyltransferase in engineered Escherichia coli", Glycoconjugate Journal 18:465-474. (2001).
Dumon et al. "Production of Lewis x Tetrasaccharides by Metabolically Engineered Escherichia coli." Chembiochem. 7.2(2006):359-365.
Dumon et al., "Assessment of the two Helicobacter pylori alpha-1,3-fucosyltransferase ortholog genes for the large-scale synthesis of LewisX human milk oligosaccharides by metabolically engineered Escherichia coli," Biotechnol Prog. Mar.-Apr. 2004; 20(2): 412-419.
Easton et al. "Human Myeloid a 3-Fucosyltransferase is Involved in the Expression of the Sialyl-Lewisx Determinant, a Ligand for E- and P-Selectin." Blood. 81.11(1993):2978-2986.
Endo et al. "Large-Scale Production of N-Acetyllactosamine Through Bacterial Coupling." Carbohydr. Res. 316.1-4(1999):179-183.
Endo et al. "Large-Scale Production of the Carbohydrate Portion of the Sialyl-Tn Epitope, a-Neup5Ac-(2-*6)-D-GalpNAc, Through Bacterial Coupling." Carbohydr. Res. 330.4(2001):439-443.
Endo et al. "Large-Scale Production of the CMP-NeuAc and Sialylated Oligosaccharides Through Bacterial Coupling." Appl. Microbiol. Biotechnol. 53.3(2000):257-261.
Erney et al. "Human Milk Oligosaccharides: A Novel Method Provides Insight into Human Genetics." Adv. Exp. Med. Biol. 501(2001):285-297.
Fierfort et al. "Genetic Engineering of Escherichia coli for the Econominal Production of Sialylated Oligosaccharides." J. Biotechnol. 134.3-4(2008):261-265.
Flowers. "Chemical Synthesis of Oligosaccharides." Meth. Enzymol. 50(1978):93-121.
Garcia et al. "Comparison and Calibration of Different Reporters for Quantitative Analysis of Gene Expression." Biophys. J. 101(2011):535-544.
Ge et al. "Cloning and Heterologous Expression of an a1,3-Fucosyltransferase Gene from the Gastric Pathogen Helicobacter pylori." J. Biol. Chem. 272.34(1997):21357-21363.
GenBank Accession No. YP_211536, Mar. 10, 2005.
GenBank Accession No. AAD407131.1, Jun. 23, 1999.
GenBank Accession No. AAG29920, Nov. 6, 2000.
GenBank Accession No. AAG29921, Nov. 6, 2000.
GenBank Accession No. ADN91474, Sep. 28, 2010.
GenBank Accession No. AF194963, Feb. 20, 2003.
GenBank Accession No. AF285774.2, Nov. 27, 2015.
GenBank Accession No. BAA15899, Nov. 20, 2008.
GenBank Accession No. BAA15900, Nov. 20, 2008.
GenBank Accession No. BAA15913, Nov. 20, 2008.
GenBank Accession No. BAE76573, Nov. 20, 2008.
GenBank Accession No. BAE76575, Nov. 20, 2008.
GenBank Accession No. BAE76576, Nov. 20, 2008.
GenBank Accession No. BAE77265, Nov. 20, 2008.
GenBank Accession No. D00067, Jun. 15, 2010.
GenBank Accession No. E04821, Nov. 4, 2005.
GenBank Accession No. EF452503, Feb. 28, 2008.
GenBank Accession No. HV532291, Dec. 27, 2011.
GenBank Accession No. L20572, Mar. 17, 1994.
GenBank Accession No. M58003, Dec. 6, 1995.
GenBank Accession No. M84410, Apr. 27, 1993.
GenBank Accession No. V00295, Jul. 7, 1995.
GenBank Accession No. V00296, Apr. 18, 2005.
GenBank Accession No. X51872, Jul. 5, 1999.
Gilbert et al. "Biosynthesis of Ganglioside Mimics in Campylobacterjejuni OH4384. Identification of the Glycosyltransferase Genes, Enzymatic Synthesis of Model Compounds, and Characterization of Nanomole Amounts by 600-MHz 1H and 13C NMR Analysis." J. Biol. Chem. 275.6(2000):3896-3906.
Gilbert et al. "Characterization of a Recombinant Neisseria meningitidis a-2,3-Sialyltransferase and its Acceptor Specificity." Eur. J. Biochem. 249.1(1997):187-194.
Gilbert et al. "Cloning of the Lipooligosaccharide a-2,3-Sialyltransferase From the Bacterial Pathogens Neisseria meningitidis and Neisseria gonorrhoeae." J. Biol. Chem. 271.45(1996):28271-28276.
Gottesman et at "Regulation of Capsular Polysaccharide Synthesis in Escherichia coli K12." Mol. MicrobioL 5.7(1991):1599-1606.
Gupte et al. "Isolation and Characterization of rcsB Mutations that Affect Colanic Acid Capsule Synthesis in Escherichia coli K-12." J. Bacteria. 179.13(1997):4328-4335.
Hamosh. "Bioactive Factors in Human Milk." Pediatr. Clin. North Am. 48.1(2001):69-86.
Han et al. "Biotechnological Product of Human Milk Oligosaccharides." Biotechnol. Adv. 30.6(2012):1268-128.
Jeanneau et al. "Structure-Function Analysis of the Human Sialyltransferase ST3Gal I: Role of N-Glycosylation and a Novel Conserved Sialylmotif." J. Biol. Chem. 279.14(2004):13461-13468.
Johnson. "Synthesis of Oligosaccharides by Bacterial Enzymes." Glycoconj. J. 16.2(1999):141-146.
Koeller et al. "Synthesis of Complex Carbohydrates and Glycoconjugates: Enzyme-Based and Programmable One-Pot Strategies." Chem. Rev. 100.12(2000):4465-4494.
Koizumi et al. "Large-Scale Production of UDP-Galactose and Globotriose by Coupling Metabolically Engineered Bacteria." Nat. Biotechnol. 16.9(1998):847-850.
Kuhlenschmidt et al. "Sialic Acid Dependence and Independence of Group A Rotaviruses." Adv. Exp. Med. Biol. 473(1999):309-317.
Legaigneur et al. "Exploring the Acceptor Substrate Recognition of the Human 13-Galactoside a2,6-Sialyltransferase." J. Biol. Chem. 276.24(2001):21608-21617.
Li et al. "Characterization of a Novel a1,2-Fucosyltransferase of Escherichia coli 0128:B12 and Functional Investigation of its Common Motif." Biochem. 47.1(2008):378-387.
Li et al. "Identification of a New al ,2-Fucosyltransferase Involved in 0-Antigen Biosynthesis of Escherichia coli 086:B7 and Formation of H-Type 3 Blood Group Antigen." Biochem. 47.44(2008):11590-11597.
Ma et al. "A Single Aromatic Acid at the Carboxyl Terminus of Helicobacter pylori al ,3/4 Fucosyltransferase Determines Substrate Specificity." J. Biol. Chem. 280.44(2005):36848-36856.
Mandavi et al. "Helicobater pylori SabA Adhesin in Persistent Infection and Chronic Inflammation." Science. 297.5581(2002):573-578.
Martin et al. "Lewis X Biosynthesis in Helicobacter pylori. Molecular Cloning of an a(1,3)-Fucosyltransferase Gene." J. Biol. Chem. 272.34(1997):21349-21356.
Martin-Sosa et al. "Sialyloligosaccharides in Human and Bovine Milk and in Infant Formulas: Variations with the Progression of Lactation." J. Dairy Sci. 86.1(2003):52-59.
Mieschendahl et al. "A Novel Prophage Independent TRP Regulated A PL." Nat. Biotechnol. 4.9(1986):802-808.

(56) References Cited

OTHER PUBLICATIONS

Moran. "Relevance of Fucosylation and Lewis Antigen Expression in the Bacterial Gastroduodenal Pathogen Helicobacter pylori." Carbohydr. Res. 343.12(2008)1952-1965.
Morrow et al. "Human Milk Oligosaccharides are Associated with Protection Against Diarrhea in Breast-Fed Infants." *J. Pediatr.* 145.3(2004):297-303.
Newburg et al. "Innate Protection Conferred by Fucosylated Oligosaccharides of Human Milk Against Diarrhea in Breastfed Infants." *Glycobiol.* 14.3(2004):253-263.
Newburg et al. "Role of Human-Milk Lactadherin in Protection Against Symptomatic Rotavirus Infection." *Lancet.* 351. 9110(1998):1160-1164.
Newburg. "Bioactive Components of Human Milk: Evolution, Efficiency, and Protection." *Adv. Exp. Med. Biol.* 501(2001):3-10.
Newburg. "Human Milk Glycoconjugates that Inhibit Pathogens." *Curr. Med. Chem.* 6.2(1999):117-127.
Ninonuevo et al. "A Strategy for Annotating the Human Milk Glycome." *J. Agric. Food Chem.* 54.20(2006):7471-7480.
Palcic. "Biocatalytic Synthesis of Oligosacchrides." *Curr. Opin. Biotechnol.* 10.6(1999):616-624.
Parkkinen et al. "Isolation of Sialyl Oligosaccharides and Sialyl Oligosaccharide Phosphates from Bovine Colostrum and Human Urine." Meth. EnymoL 138(1987):289-300.
Rasko et al. "Cloning and Characterization of the a(1,3/4) Fucosyltransferase of Helicobacter pylori." J. Biol. Chem. 275. 7(2000):4988-4994.
Ringenberg et al. "Redirection of Sialic Acid Metabolism in Genetically Engineered *Escherichia coli.*" *Glycobiol.* 11.7(2001):533-539.
Roberfroid et al. "Prebiotic Effects: Metabolic and Health Benefits." *Br. J. Nutr.* 104.S2(2010):S1-S63.
Ruiz-Palacios et al. "Campylobacterijejuni Binds Intestinal H(0) Antigen (Fuc al, 2Gal (31, 4GlcNAc) and Fucosyloligosaccharides of Human Milk Inhibit its Binding and Infection." J. Biol. Chem. 278.16(2003):14112-14120.
Rydell et al. "Human Noroviruses Recognize Sialyl Lewis x Neoglycoprotein." *Glycobiol.* 19.3(2009):309-320.
Sanger et al. "Nucleotide Sequence of Bacteriophage A DNA." J. Mol. Biol. 162.4(1982):729-773.
Scharfman et al. "Sialyl-Lex and Suflo-Sialyl-Lex Determinants are Receptors for *P. aeruginosa.*" *Glycoconj.* J. 17.10(2000):735-740.
Seeberger. "Automated Carbohydrate Synthesis to Drive Chemical Glycomics." *Chme. Commun. (Camb).* 10(2003):1115-1121.
Shen et al. "Resolution of Structural Isomers of Sialylated Oligosaccharides by Capillary Electrophoresis." *J. Chromatogr. A.* 921. 2(2001):315-321.
Stevenson et al. "Organization of the *Escherichia coli* K-12 Gene Cluster Responsible for Production of the Extracellular Polysaccharide Colanic Acid." *J. Bacteriol.* 178.16(1996):4885-4893.
Taniguchi. "Promoter Structure and Transcriptional Regulation of Human 13-Galactoside a2, 3-Sialyltransferase Genes." Curr. Drug Targets. 9.4(2008):310-316.
Thomason et al. "*E. coli* Genome Manipulation by P1 Transduction." *Curr. Protoc. Mol. Biol.* Chapter 1, Unit 1.17(2007).
Tsai et al. "Influence of the Length of the Lipooligosaccharide a Chain on its Sialylation in the Neisseria meningitidis." Infect. Immun. 70.1(2002):407-411.
UniProt Accession No. P0A9M0 (Feb. 2008).
Wang et al. "Molecular Genetic Basis for the Variable Expression of Lewis Y Antigen in Helicobacter pylori: Analysis of the a (1,2) Fucosyltransferase Gene." Mol. Microbiol. 31.4(1999):1265-1274.
Ward et al. "In vitro Fermentability of Human Milk Oligosaccharides by Several Strains of Bifidobacteria." *Mol. Nutr. Food Res.* 51.11(2007):1398-1405.
Wymer et al. "Enzyme-Catalyzed Synthesis of Carbohydrates." *Curr. Opin. Chem. Biol.* 4.1(2000):110-119.
Zhang et al. "Helicobacter Hepaticus Hh0072 Gene Encodes a Novel al-3-Fucosyltransferase Belonging to CAZy GT11 Family." Glycobiol. 20.9(2010):1077-1088.

Albertson et al., Construction and use of a new vector/transposon, pLBT::mini-Tn10:lac:kan, to identify environmentally responsive genes in a marine bacterium. FEMS Microbiol Lett. Jul. 1, 1996;140(2-3):287-94.
Atkins et al., Low activity of -galactosidase in frameshift mutants of *Escherichia coli.* Proc Natl Acad Sci U S A. May 1972;69(5):1192-5.
Ebel et al., *Escherichia coli* RcsA, a positive activator of colanic acid capsular polysaccharide synthesis, functions to activate its own expression. J Bacteriol. Jan. 1999;181(2):577-84.
Ring et al., Multiple replacements establish the importance of tyrosine-503 in beta-galactosidase (*Escherichia coli*). Arch Biochem Biophys. Dec. 1990;283(2):342-50.
Xiong et al., Downstream deletion analysis of the lac promoter. J Bacteriol. Aug. 1991;173(15):4570-7.
Bachmann (1972) "Pedigrees of some mutant strains of *Escherichia coli* K 12," Bacteriological Reviews. 36(4):525-557.
Beckwith (1964) "A Deletion Analysis of the Lac Operator Region in *Escherichia coli,*" J. Mol. Biol. 8:427-430.
Croucher et al. (1983) "Bacterial populations associated with different regions of the human colon wall," Appl Environ Microbiol. 45:1025-1033.
Drouillard et al. (Mar. 2006) "Large-Scale Synthesis of H-Antigen Oligosaccharides by Expressing Helicobacter pylori α1,2-Fucosyltransferase in Metabolically Engineered *Escherichia coli* Cells," Angewandte Chemie International Edition. 45(11):1778-1780.
Endo et al. (Oct. 1, 2000) "Large Scale Production of Oligosaccharides Using Engineered Bacteria," Current Opinion in Structural Biology. 10(5):536-541.
Hoban et al. (1958) "Gradient Elution of Disaccharides on Stearic Acid Treated Charcoal Column," Analytical Chemistry. 30(7):1294-1296.
Lavallie et al. (1993) "A thioredoxin gene fusion expression system that circumvents inclusion body formation in the *E. coli* cytoplasm," Nature Biotechnology. 11(2):187-193.
McCoy et al. (1994) "Expression and purification of thioredoxin fusion proteins," Current Protocols in Molecular Biology. 28(1):16-18.
Miller (1972) "Assay of B-Galactosidase," Experiments in Molecular Genetics. 48:352-355.
Mitchell (Jul. 2, 2003) "Identification and analysis of 'extended 10' promoters in *Escherichia coli,*" Nucleic Acids Research. 31(16):4689-4695.
Thomason (Jan. 2015) "Global Transcriptional Start Site Mapping Using Differential RNA Sequencing Reveals Novel Antisense RNAs in *Escherichia coli,*" 197(1):18-28.
Wang et al. (Nov. 1999) "Novel helicobacter pylori alpha1 ,2 fucosyltransferase, a key enzyme in the synthesis of Lewis antigens," Microbiology. 145(11):3245-3253.
Ward et al. (2006) "In vitro fermentation of breast milk oligosaccharides by Bifidobacterium infantis and Lactobacillus gasseri," Appl Environ Microbiol. 72:4497-4499.
Chaturvedi et al. (1997) "Milk oligosaccharide profiles by reversed-phased HPLC of their perbenzoylated derivatives," Anal Biochem. 251:89-97.
Chessa et al. (2009) "*Salmonella enterica* serotype Typhimurium Std fimbriae bind terminal alpha(1,2)fucose residues in the cecal mucosa," Mol Microbiol. 71:864-875.
Chin et al. (2015) "Enhanced Production of 2'-Fucosyllactose in Engineered *Escherichia coli* BL21star(DE3) by Modulation of Lactose Metabolism and Fucosyltransferase," Journal of Biotechnology. 210:107-115.
Duijts et al. (2009) "Breastfeeding protects against infectious diseases during infancy in industrialized countries; A systematic review," Matern Child Nutr. 5:199-210.
Farag et al. (2007) "Helicobacter pylori infection is associated with severe anemia of pregnancy on Pemba Island, Zanzibar," Am J Trop Med Hyg. 76:541-548.
Fox et al. (2006) "Identification of a bifunctional lipopolysaccharide sialyltransferase in Haemophilus influenzae: incorporation of disialic acid," J Biol Chem. 281:40024-40032.

(56) References Cited

OTHER PUBLICATIONS

Foxall et al. (1992) "The three members of the selectin receptor family recognize a common carbohydrate epitope, the sialyl Lewis(x) oligosaccharide," J Cell Biol. 117:895-902.

GenBank Accession No. AC_000091.1, 12 pages, Accessible on the Internet at URL: https://www.ncbi.nlm.nih.gov/nuccore/AC_000091.1?report=genbank.

Gottsch et al. (2003) "Serial analysis of gene expression in the corneal endothelium of Fuchs' dystrophy," Investigative Ophthalmology & Visual Science. 44(2):594-599.

Hood et al. (2001) "Identification of a lipopolysaccharide alpha-2,3-sialyltransferase from Haemophilus influenza," Mol Microbiol. 39:341-350.

Huang et al. (2003) "Noroviruses bind to human ABO, Lewis, and secretor histo-blood group antigens: identification of 4 distinct strain-specific patterns," J Infect Dis. 188:19-31.

Jiang et al. (2004) "Human milk contains elements that block binding of noroviruses to human histo-blood group antigens in saliva," J Infect Dis. 190:1850-1859.

Kivi et al. (2006) "Helicobacter pylori occurrence and transmission: a family affair?" Scand J Infect Dis. 38:407-417.

Ko et al. (2005) "Noroviruses as a cause of traveler's diarrhea among students from the United States visiting Mexico," J Clin Microbiol. 43:6126-6129.

Li et al. (2007) "The Hd0053 gene of Haemophilus ducreyi encodes an [alpha] 2, 3-sialyltransferase," Biochemical and Biophysical Research Communications. 361:555-560.

Libster et al. (2009) "Breastfeeding prevents severe disease in full term female infants with acute respiratory infection," Pediatr Infect Dis J. 28:131-134.

Lindesmith et al. (2003) "Human susceptibility and resistance to Norwalk virus infection," Nat Med. 9:548-553.

Lorntz et al. (2006) "Early childhood diarrhea predicts impaired school performance," Pediatr Infect Dis J. 25:513-520.

Marcobal et al. (2010) "Consumption of human milk oligosaccharides by gut-related microbes," J Agric Food Chem. 58:5334-5340.

Mohammad et al. (2008) "Prevalence of Helicobacter pylori infection among Egyptian children: impact of social background and effect on growth," Public Health Nutr. 11:230-236.

Morrow et al. (2004) "Human milk oligosaccharide blood group epitopes and innate immune protection against campylobacter and calicivirus diarrhea in breastfed infants," Adv Exp Med Biol. 554:443-446.

Morrow et al. (2005) "Human-milk glycans that inhibit pathogen binding protect breast-feeding infants against infectious diarrhea," J Nutr. 135:1304-1307.

Newburg et al. (2004) "Human milk alpha1,2-linked fucosylated oligosaccharides decrease risk of diarrhea due to stable toxin of *E. coli* in breastfed infants," Adv Exp Med Biol. 554:457-461.

Newburg et al. (2005) "Human milk glycans protect infants against enteric pathogens," Annu Rev Nutr. 25:37-58.

Newburg et al. (2007) "Protection of the neonate by the innate immune system of developing gut and of human milk," Pediatr Res. 61:2-8.

Oriá et al. (2009) "Semantic fluency: a sensitive marker for cognitive impairment in children with heavy diarrhea burdens?" Med Hypotheses. 73:682-686.

Petersson et al. (2006) "Helicobacter pylori SabA adhesin evokes a strong inflammatory response in human neutrophils which is down-regulated by the neutrophil-activating protein," Med Microbiol Immunol. 195:195-206.

Stepans et al. (2006) "Early consumption of human milk oligosaccharides is inversely related to subsequent risk of respiratory and enteric disease in infants," Breastfeed Med. 1:207-215.

Takakura et al. (2007) "Molecular cloning, expression and properties of an alpha/beta-Galactoside alpha2,3-sialyltransferase from *Vibrio* sp. JT-FAJ-16," J Biochem. 142:403-412.

Tsukamoto et al. (2007) "Purification, cloning, and expression of an alpha/beta-galactoside alpha-2,3-sialyltransferase from a luminous marine bacterium, Photobacterium phosphoreum," J Biol Chem. 282:29794-29802.

Xia et al. (2007) "Pseudomonas aeruginosa mucoid strain 8830 binds glycans containing the sialyl-Lewis x epitope," Glycoconj J. 24:87-95.

Lewendon et al. (1995) "Structural and mechanistic studies of galactoside acetyltransferase, the *Escherichia coli* LacA gene product," Journal of Biological Chemistry. 270(44)26326-26331.

Miller JH, Experiment 48 Assay of β-Galactosidase, pp. 352-355, 1972.†

Kawano M, Detection of low-level promoter activity within open reading frame sequences of *Escherichia coli*, pp. 6268-6276, 2005.†

Stephanopoulos G, Declaration of Gregory Stephanopoulos, pp. i, ii, and 1-52, 2019.†

Giacomini A, Experimental conditions may affect reproducibility of the beta-galactosidase assay, pp. 87-90, 1992.†

Schaefer J, A data comparison between a traditional and the single-step β-galactosidase assay, pp. 350-352, 2016.†

† cited by third party

FIG. 13A

```
LOCUS       W3110 delta lon::Kan::lacZ_with_RBS      5049 bp    DNA
linear   BCT 19-FEB-2009
DEFINITION  Escherichia coli str. K-12 substr. W3110 strain K-12.
ACCESSION   AC_000091
VERSION     AC_000091.1  GI:89106884
KEYWORDS    .
SOURCE      Escherichia coli str. K-12 substr. W3110 (unknown)
  ORGANISM  Escherichia coli str. K-12 substr. W3110
            Bacteria; Proteobacteria; Gammaproteobacteria;
Enterobacteriales;
            Enterobacteriaceae; Escherichia.
FEATURES             Location/Qualifiers
     gene            1..112
                     /gene="clpX"
     CDS             1..112
                     /gene="clpX"
                     /note="ECK0432;JW0428;b0438"
                     /codon_start=1
                     /transl_table=11
                     /product="ATPase and specificity subunit of ClpX-ClpP
ATP-dependent serine protease"
                     /protein_id="AP_001088.1"
                     /db_xref="GI:89107308"
/translation="MTDKRKDGSGKLLYCSFCGKSQHEVRKLIAGPSVYICDECVDLC
NDIIREEIKEVAPHRERSALPTPHEIRNHLDDYVIGQEQAKKVLAVAVYNHYKRLRNG
DTSNGVELGKSNILLIGPTGSGKTLLAETLARLLDVPFTMADATTLTEAGYVGEDVEN
IIQKLLQKCDYDVQKAQRGIVYIDEIDKISRKSDNPSITRDVSGEGVQQALLKLIEGT
VAAVPPQGGRKHPQQEFLQVDTSKILFICGGAFAGLDKVISHRVETGSGIGFGATVKA
KSDKASEGELLAQVEPEDLIKFGLIPEFIGRLPVVATLNELSEEALIQILKEPKNALT
KQYQALFNLEGVDLEFRDEALDAIAKKAMARKTGARGLRSIVEAALLDTMYDLPSMED
VEKVVIDESVIDGQSKPLLIYGKPEAQQASGE" (SEQ ID NO: 9)
                     /label="clpX (partial gene)"
     host_DNA        1..302
                     /label="E. coli W3110 chromosome"
     source          1..302
                     /organism="Escherichia coli str. K-12 substr. W3110"
                     /mol_type="genomic DNA"
                     /strain="K-12"
                     /sub_strain="W3110"
                     /db_xref="taxon:316407"
     primer          258..302
                     /label="lon-H1 Lambda red homology region"
     gene            300..302
                     /gene="lon"
     CDS             300..302
                     /gene="lon"
                     /note="ECK0433;JW0429;b0439"
                     /codon_start=1
                     /transl_table=11
                     /product="DNA-binding ATP-dependent protease La"
                     /protein_id="AP_001089.1"
                     /db_xref="GI:89107309"
/translation="MNPERSERIETPVLPLRDVVVYPHMVIPLFVGREKSIRCLEAAM
DHDKKIMLVAQKEASTDEPGVNDLFTVGTVASILQMLKLPDGTVKVLVEGLQRARISA
LSDNGEHFSAKAEYLESPTIDEREQEVLVRTAISQFEGYIKLNKKIPPEVLTSLNSID
DPARLADTIAAHMPLKLADKQSVLEMSDYNERLEYLMAMMESEIDLLQVEKRIRNRVK
KQMEKSQREYYLNEQMKAIQKELGEMDDAPDENEALKRKIDAAKMPKEAKEKAEAELQ
```

FIG. 13B

KLKMMSPMSAEATVVRGYIDWMVQVPWNARSKVKKDLRQAQEILDTDHYGLERVKDRI
LEYLAVQSRVNKIKGPILCLVGPPGVGKTSLGQSIAKATGRKYVRMALGGVRDEAEIR
GHRRTYIGSMPGKLIQKMAKVGVKNPLFLLDEIDKMSSDMRGDPASALLEVLDPEQNV
AFSDHYLEVDYDLSDVMFVATSNSMNIPAPLLDRMEVIRLSGYTEDEKLNIAKRHLLP
KQIERNALKKGELTVDDSAIIGIIRYYTREAGVRGLERETSKLCRKAVKQLLLDKSLK
HIEINGDNLHDYLGVQRFDYGRADNENRVGQVTGLAWTEVGGDLLTIETACVPGKGKL
TYTGSLGEVMQESIQAALTVVRARAEKLGINPDFYEKRDIHVHVPEGATPKDGPSAGI
AMCTALVSCLTGNPVRADVAMTGEITLRGQVLPIGGLKEKLLAAHRGGIKTVLIPFEN
KRDLEEIPDNVIADLDIHPVKRIEEVLTLALQNEPSGMQVVTAK" (SEQ ID NO: 10)

```
                        /label="lon N-terminus (initiator methionine codon
only remains)"
    repeat_unit         303..330
                        /label="Flp site"
    primer_bind         303..322
                        /label="P4 wanner=P1 Baba and Mori"
    source              complement(303..1605)
                        /organism="Template plasmid pKD13"
                        /mol_type="genomic DNA"
                        /db_xref="taxon:170493"
    misc_feature        complement(303..4704)
                        /note="originates from KanR-lacZRBS-"
                        /label=Insert
    repeat_unit         331..364
                        /label="34 nt Flp site scar"
    repeat_unit         331..342
                        /label="Flp site"
    repeat_unit         complement(353..364)
                        /label="FLP site"
    Region              365..1586
                        /label="excised region upon pCP20 introduction"
    KAN_resistance      732..1526
                        /note="kanamycin resistance"
                        /codon_start=1
                        /transl_table=11
                        /product="Tn5 neomycin phosphotransferase"
                        /protein_id="AAL02037.1"
                        /db_xref="GI:15554336"
                        /translation="MIEQDGLHAGSPAAWVERLFGYDWAQQTIGCSDAAVFRLSAQGR
PVLFVKTDLSGALNELQDEAARLSWLATTGVPCAAVLDVVTEAGRDWLLLGEVPGQDL
LSSHLAPAEKVSIMADAMRRLHTLDPATCPFDHQAKHRIERARTRMEAGLVDQDDLDE
EHQGLAPAELFARLKARMPDGEDLVVTHGDACLPNIMVENGRFSGFIDCGRLGVADRY
QDIALATRDIAEELGGEWADRFLVLYGIAAPDSQRIAFYRLLDEFF"(SEQ ID NO: 11)
    repeat_unit         1539..1550
                        /label="Flp site"
    misc_feature        1539..1586
                        /note="natural FRT site"
    repeat_unit         1553..1564
                        /label="Flp site"
    repeat_unit         complement(1575..1586)
                        /label="FLP site"
    primer_bind         complement(1586..1605)
                        /label="P1 Wanner=P2 Baba et al"
    repeat_unit         1587..1605
                        /label="Flp site downstream scar Baba et al"
    Site                join(1615^1616,1610..1617)
                        /note="Name: NotI"
                        /note="Pattern: gcggccgc"
                        /note="cut_0 on positive_strand: 3083^3084"
                        /note="cut_0 on negative_strand: 3087^3088"
                        /note="inhibited by: 5': N4-methylcytosine"
                        /note="site_type: other"
```

FIG. 13C

```
                        /note="restriction site"
                        /label=NotI
        source          1618..4704
                        /organism="Escherichia coli W3110"
                        /mol_type="genomic DNA"
                        /strain="K-12"
                        /sub_strain="W3110"
                        /db_xref="taxon:316407"
                        /note="synonym: Escherichia coli str. K12 substr.
        W3110"
        wild_type_CDS   complement(1618..4692)
                        /gene="lacZ"
                        /note="ECK0341:JW0335:b0344"
                        /codon_start=1
                        /transl_table=11
                        /product="beta-D-galactosidase"
                        /protein_id="BAE76126.1"
                        /db_xref="GI:85674486"
/translation="MTMITDSLAVVLQRRDWENPGVTQLNRLAAHPPFASWRNSEEAR
TDRPSQQLRSLNGEWRFAWFPAPEAVPESWLECDLPEADTVVVPSNWQMHGYDAPIYT
NVTYPITVNPPFVPTENPTGCYSLTFNVDESWLQEGQTRIIFDGVNSAFHLWCNGRWV
GYGQDSRLPSEFDLSAFLRAGENRLAVMVLRWSDGSYLEDQDMWRMSGIFRDVSLLHK
PTTQISDFHVATRFNDDFSRAVLEAEVQMCGELRDYLRVTVSLWQGETQVASGTAPFG
GEIIDERGGYADRVTLRLNVENPKLWSAEIPNLYRAVVELHTADGTLIEAEACDVGFR
EVRIENGLLLLNGKPLLIRGVNRHEHHPLHGQVMDEQTMVQDILLMKQNNFNAVRCSH
YPNHPLWYTLCDRYGLYVVDEANIETHGMVPMNRLTDDPRWLPAMSERVTRMVQRDRN
HPSVIIWSLGNESGHGANHDALYRWIKSVDPSRPVQYEGGGADTTATDIICPMYARVD
EDQPFPAVPKWSIKKWLSLPGETRPLILCEYAHAMGNSLGGFAKYWQAFRQYPRLQGG
FVWDWVDQSLIKYDENGNPWSAYGGDFGDTPNDRQFCMNGLVFADRTPHPALTEAKHQ
QQFFQFRLSGQTIEVTSEYLFRHSDNELLHWMVALDGKPLASGEVPLDVAPQGKQLIE
LPELPQPESAGQLWLTVRVVQPNATAWSEAGHISAWQQWRLAENLSVTLPAASHAIPH
LTTSEMDFCIELGNKRWQFNRQSGFLSQMWIGDKKQLLTPLRDQFTRAPLDNDIGVSE
ATRIDPNAWVERWKAAGHYQAEAALLQCTADTLADAVLITTAHAWQHQGKTLFISRKT
YRIDGSGQMAITVDVEVASDTPHPARIGLNCQLAQVAERVNWLGLGPQENYPDRLTAA
CFDRWDLPLSDMYTPYVFPSENGLRCGTRELNYGPHQWRGDFQFNISRYSQQQLMETS
HRHLLHAEEGTWLNIDGFHMGIGGDDSWSPSVSAEFQLSAGRYHYQLVWCQK"(SEQ ID NO: 12)
                        /label="wild-type lacZ+ CDS"
        epitope_tag     complement(4671..4704)
                        /label="LacFKpnInoRBS cloning primer"
        RBS             complement(4693..4704)
        gene            <4705..4725
                        /gene="lon"
        CDS             <4705..4725
                        /gene="lon"
                        /note="ECK0433:JW0429:b0439"
                        /codon_start=1
                        /transl_table=11
                        /product="DNA-binding ATP-dependent protease La"
                        /protein_id="AP_001089.1"
                        /db_xref="GI:89107309"
/translation="MNPERSERIEIPVLPLRDVVVYPHMVIPLFVGREKSIRCLEAAM
DHDKKIMLVAQKEASTDEPGVNDLFTVGTVASILQMLKLPDGTVKVLVEGLQRARISA
LSDNGEHFSAKAEYLESPTIDEREQEVLVRTAISQFEGYIKLNKKIPPEVLTSLNSID
DPARLADTIAAHMPLKLADKQSVLEMSDVNERLEYLMAMMESEIDLLQVEKRIRNRVK
KQMEKSQREYYLNEQMKAIQKELGEMDDAPDENEALKRKIDAAKMPKEAKEKAEAELQ
KLKMMSPMSAEATVVRGYIDWMVQVPWNARSKVKKDLRQAQEILDTDHYGLERVKDRI
LEYLAVQSRVNKIKGPILCLVGPPGVGKTSLGQSIAKATGRKYVRMALGGVRDEAEIR
GHRRTYIGSMPGKLIQKMAKVGVKNPLFLLDEIDKMSSDMRGDPASALLEVLDPEQNV
AFSDHYLEVDYDLSDVMFVATSNSMNIPAPLLDRMEVIRLSGYTEDEKLNIAKRHLLP
KQIERNALKKGELTVDDSAIIGIIRYYTREAGVRGLEREISKLCRKAVKQLLLDKSLR
```

FIG. 13D

```
HIEINGDNLHDYLGVQRFDYGRADNENRVGQVTGLAWTEVGGDLLTIETACVPGKGKL
TYTGSLGEVMQESIQAALTVVRAKAEKLGINPDFYEKRDIHVHVPEGATPKDGPSAGI
AMCTALVSCLTGNPVRADVAMTGEITLRGQVLPIGGLKEKLLAAHRGGIKTVLIPFEN
KRDLEEIPDNVIADLDIHPVKRIEEVLTLALQNEPSGMQVVTAK" (SEQ ID NO: 13)
                /label="lon C-terminus (encodes 6 C-terminal
residues)"
        host_DNA        4705..5049
                        /label="E. coli W3110 chromosome"
        source          <4705..>5049
                        /organism="Escherichia coli str. K-12 substr. W3110"
                        /mol_type="genomic DNA"
                        /strain="K-12"
                        /sub_strain="W3110"
                        /db_xref="taxon:316407"
        primer          complement(4705..4749)
                        /label="lon-H2 homology region for lambda red"
        gene            4934..>5049
                        /gene="hupB"
        CDS             4934..>5049
                        /gene="hupB"
                        /note="ECK0434;JW0430;b0440"
beta subunit"           /codon_start=1
                        /transl_table=11
                        /product="HU, DNA-binding transcriptional regulator,
                        /protein_id="AP_001090.1"
                        /db_xref="GI:89107310"
/translation="MNKSQLIDKIAAGADISKAAAGRALDAIIASVTESLKEGDDVAL
VGFGTFAVKERAARTGRNPQTGKEITIAAAKVPSFRAGKALKDAVN"(SEQ ID NO: 14)
                        /label="hupB (partial gene)"
ORIGIN
    1 GTCCATGGAA GACGTCGAAA AAGTGGTTAT CGACGAGTCG GTAATTGATG GTCAAAGCAA
   61 ACCGTTGCTG ATTTATGGCA AGCCCGGAAGC GCAACAGGCA TCTGGTGAAT AATTAACCAT
  121 TCCCATACAA TTAGTTAACC AAAAAGGGGG GATTTTATCT CCCCTTTAAT TTTTCCTCTA
  181 TTCTCGGCGT TGAATGTGGG GGAAACATCC CCATATACTG ACGTACATGT TAAATAGATGG
  241 CGTGAAGCAC AGTCGTGTCA TCTGATTACC TGGCGGAAAT TAAACTAAGA GAGAGCTCCA
  301 TGATTCCGGG GATCCGTCGA CCTGCAGTTC GAAGTTCCTA TTCTCTAGAA AGTATAGGAA
  361 CTTCAGAGCG CTTTTTGAAGC TCACGCTGCC GCAAGCACTC AGGGGCGCAAG GGCTGCTAAA
  421 GGAAGCGGAA CAACGTAGAAA GCCAGTCCGC AGAAACGGTG CTGACCCCGG ATGAATGTCA
  481 GCTACTGGGC TATCTGGACA AGGGAAAAGC CAAGCGACAA GAGAAAGCAG GTAGCTTGCA
  541 GTGGGCTTAC ATGGCGGATAG CTAGACTGGG CGGTTTTATG GACAGCACAC GAACCCGAAT
  601 TGCCAGCTGG GGCGCCCTCT GGTAAGGTTG GGAAGCCCTG CAAAGTAAAC TGGATGGCTT
  661 TCTTGCCGCC AAGGATCTGA TGGCGCAGGG GATCAAGATC TGATCAAGAG ACAGGATGAG
  721 GATCGTTTCG CATGATTGAA CAAGATGGAT TGCACGCAGG TTCTCCGGCC GCTTGGGTGG
  781 AGAGGCTATT CGGCTATGAC TGGGCACAAC AGACAATCCG CTGCTCTGAT GCCCCCCTGT
  841 TCCGGCTGTC AGCGCAGGGG CGCCCGGTTC TTTTTGTCAA GACCGACCTG TCCGGTGCCC
  901 TGAATGAACT GCAGGACGAG GCAGCGCGGC TATCGTGGCT GGCCACGACG GGCGTTCCTT
  961 GCGCAGCTGT GCTCGACGTT GTCACTGAAG CGGGAAGGGA CTGGCTGCTA TTGGGCGAAG
 1021 TGCCGGGGCA GGATCTCCTG TCATCTCACC TTGCTCCTGC CGAGAAAGTA TCCATCATGG
 1081 CTGATGCAAT GCGGCGGCTG CATACGCTTG ATCCGGCTAC CTGCCCATTC GACCACCAAG
 1141 CGAAACATCG CATCGAGCGA GCACGTACTC GGATGGAAGC CGGTCTTGTC GATCAGGATG
 1201 ATCTGGACGA AGAGCATCAG GGGCTCGCGC CAGCCGAACT GTTCGCCAGG CTCAAGGCGC
 1261 GCATGCCCGA CGGCGAGGAT CTCGTCGTGA CCCATGGCGA TGCCTGCTTG CCGAATATCA
 1321 TGGTGGAAAA TGGCCGCTTT TCTGGATTCA TCGACTGTGG CCGGCTGGGT GTGGCGGACC
 1381 GCTATCAGGA CATAGCGTTG GCTACCCGTG ATATTGCTGA AGAGCTTGGC GGCGAATGGG
 1441 CTGACCGCTT CCTCGTGCTT TACGGTATCG CCGCTCCCGA TTCGCAGCGC ATCGCCTTCT
 1501 ATCGCCTTCT TGACGAGTTC TTCTAATAAG GGGATCTTGA AGTTCCTATT CCGAAGTTCC
 1561 TATTCTCTAG AAAGTATAGG AACTTCGAAG CAGCTCCAGC CTACATAAAG CGGCCGCTTA
 1621 TTTTTGACAC CAGACCAACT GGTAATGGTA GCGACCGGCG CTCAGCTGGA ATTCCGCGA
 1681 TACTGACGGG CTCCAGGAGT CGTCGCCACC AATCCCCATA TGGAAACCGT CGATATTCAG
 1741 CCATGTGCCT TCTTCCGCGT GCAGCAGATG GCGATGGCTG GTTTCCATCA GTTGCTGTTG
```

FIG. 13E

```
1801 ACTGTAGCGG CTGATGTTGA ACTGGAAGTC GCCGCGCCAC TGGTGTGGGC CATAATTCAA
1861 TTCGCGCGTC CCGCAGCGCA GACCGTTTTC GCTCGGGAAG ACGTACGGGG TATACATGTC
1921 TGACAATGGC AGATCCAGC GGTCAAAACA GGCGGCAGTA AGGCGGTCGG GATAGTTTTC
1981 TTGCGGCCCT AATCCGAGCC AGTTTACCCG CTCTGCTACC TGCGCCAGCT GGCAGTTCAG
2041 GCCAATCCGC GCCGGATGCG GTGTATCGCT CGCCACTTCA ACATCAACGG TAATCGCCAT
2101 TTGACCACTA CCATCAATCC GGTAGGTTTT CCGGCTGATA AATAAGGTTT TCCCCTGATG
2161 CTGCCACGCG TGAGCGGTCG TAATCAGCAC CGCATCAGCA AGTGTATCTG CCGTGCACTG
2221 CAACAACGCT GCTTCGGCCT GGTAATGGCC CGCCGCCTTC CAGCGTTCGA CCCAGGCGTT
2281 AGGGTCAATG CGGGTCGCTT CACTTACGCC AATGTCGTTA TCCAGCGGTG CACGGGTGAA
2341 CTGATCGCGC AGCGGCGTCA GCAGTTGTTT TTTATCGCCA ATCCACATCT GTGAAAGAAA
2401 GCCTGACTGG CGGTTAAATT GCCAACGCTT ATTACCCAGC TCGATGCAAA AATCCATTTC
2461 GCTGGTGGTC AGATGCGGGA TGGCGTGGGA CGCGGCGGGG AGCGTCACAC TGAGGTTTTC
2521 CGCCAGACGC CACTGCTGCC AGGCGCTGAT GTGCCCGGCT TCTGACCATG CGGTCGCGTT
2581 CGGTTGCACT ACGCGTACTG TGAGCCAGAG TTGCCCGGCG CTCTCCGGCT GCGGTAGTTC
2641 AGGCAGTTCA ATCAACTGTT TACCTTGTGG AGCGACATCC AGAGGCACTT CACCGCTTGC
2701 CAGCGGCTTA CCATCCAGCG CCACCATCCA GTGCAGGAGC TCGTTATCGC TATGACGGAA
2761 CAGGTATTCG CTGGTCACTT CGATGGTTTG CCCGGATAAA CGGAACTGGA AAAACTGCTG
2821 CTGGTGTTTT GCTTCCGTCA GCGCTGGATG CGGCGTGCGG TCGCAAAGA CCAGACCGTT
2881 CATACAGAAC TGGCGATCGT TCGGCGTATC GCCAAAATCA CCGCCGTAAG CCGACCACGG
2941 GTTGCCGTTT TCATCATATT TAATCAGCGA CTGATCCACC CAGTCCAGA CGAAGCCGCC
3001 CTGTAAACGG GGATACTGAC GAAACGCCTG CCAGTATTTA GCGAAACCGC CAAGACTGTT
3061 ACCCATCGCG TGGGCGTATT CGCAAAGGAT CAGCGGGCGC GTCTCTCCAG GTAGCGAAAG
3121 CCATTTTTTG ATGGACCATT TCGGCACAGC CGGGAAGGGC TGGTCTTCAT CCACGCGCGC
3181 GTACATCGGG CAAATAATAT CGGTGGCCGT GGTGTCGGCT CCGCCGCCTT CATACTGCAC
3241 CGGGCGGGAA GGATCGACAG ATTTGATCCA GCGATACAGC GCGTCGTGAT TAGCGCCGTG
3301 GCCTGATTCA TTCCCCAGCG ACCAGATGAT CACACTCGGG TGATTACGAT CGCGCTGCAC
3361 CATTCGCGTT ACGCGTTCGC TCATCGCCGG TAGCCAGCGC GGATCATCGG TCAGACGATT
3421 CATTGGCACC ATGCCGTGGG TTTCAATATT GGCTTCATCC ACCACATACA GGCCGTAGCG
3481 GTCGCACAGC GTGTACCACA GCGGATGGTT CGGATAATGC GAACAGCGCA CGGCGTTAAA
3541 GTTGTTCTGC TTCATCAGCA GGATATCCTG CACCATCGTC TGCTCATCCA TGACCTGACC
3601 ATGCAGAGGA TGATGCTCGT GACGGTTAAC GCCTCGAATC AGCAACGGCT TGCCGTTCAG
3661 CAGCAGCAGA CCATTTTCAA TCCGCACCTC GCGGAAACCG ACATCGCAGG CTTCTGCTTC
3721 AATCAGCGTG CCGTCGGCGG TGTGCAGTTC AACCACCGCA CGATAGAGAT TCGGGATTTC
3781 GGCGCTCCAC AGTTTCGGGT TTTCGACGTT CAGACGTAGT GTGACGCGAT CGGCATAACC
3841 ACCACGCTCA TCGATAATTT CACCGCCGAA AGGCGCGGTG CCGCTGGCGA CCTGCGTTTC
3901 ACCCTGCCAT AAAGAAACTG TTACCCGTAG GTAGTCACGC AACTCGCCGC ACATCTGAAC
3961 TTCAGCCTCC AGTACAGCGC GGCTGAAATC ATCATTAAAG CGAGTGGCAA CATGGAAATC
4021 GCTGATTTGT GTAGTCGGTT TATGCAGCAA CGAGACGTCA CGGAAAATGC CGCTCATCCG
4081 CCACATATCC TGATCTTCCA GATAACTGCC GTCACTCCAG CGCAGCACCA TCACCGCGAG
4141 GCGGTTTTCT CCGGCGCGTA AAAATGCGCT CAGGTCAAAT TCAGACGGCA AACGACTGTC
4201 CTGGCCGTAA CCGACCCAGC GCCCGTTGCA CCACAGATGA AACGCCGAGT TAACGCCATC
4261 AAAAATAATT CGCGTCTGGC CTTCCTGTAG CCAGCTTTCA TCAACATTAA ATGTGAGCGA
4321 GTAACAACCC GTCGGATTCT CCGTGGGAAC AAACGGCGGA TTGACCGTAA TGGGATAGGT
4381 CACGTTGGTG TAGATGGGCG CATCGTAACC GTGCATCTGC CAGTTTGAGG GGACGACGAC
4441 AGTATCGGCC TCAGGAAGAT CGCACTCCAG CCAGCTTTCC GGCACCGCTT CTGGTGCCGG
4501 AAACCAGGCA AAGCGCCATT CGCCATTCAG GCTGCGCAAC TGTTGGGAAG GGCGATCGGT
4561 GCGGGCCTCT TCGCTATTAC GCCAGCTGGC GAAAGGGGGA TGTGCTGCAA GGCGATTAAG
4621 TTGGGTAACG CCAGGGTTTT CCCAGTCACG ACGTTGTAAA ACGACGGCCA GTGAATCCGT
4681 AATCATGGTC ATagtaggtt tcctCAGGTT GTGACTGCAA AATAGTGACC TCGCGCAAAA
4741 TGCACTAATA AAAACAGGGC TGGCAGGCTA ATTCGGGCTT GCCAGCCTTT TTTTGTCTCG
4801 CTAAGTTAGA TGGCGGATCG GGCTTGCCCT TATTAAGGGG TGTTGTAAGG GGATGGCTGG
4861 CCTGATATAA CTGCTGCGCG TTCGTACCTT GAAGGATTCA AGTGCGATAT AAATTATAAA
4921 GAGGAAGAGA AGAGTGAATA AATCTCAATT GATCGACAAG ATTGCTGCAG GGGCTGATAT
4981 CTCTAAAGCT GCGGCTGGCC GTGCGTTAGA TGCTATTATT GCTTCCGTAA CTGAATCTCT
5041 GAAAGAAGG (SEQ ID NO: 15)
```

*E.coli* strains of the current invention

| | | | | | |
|---|---|---|---|---|---|
| E100 (GI724) | ampC::(P$_{trpB}$λcI+) | lacI$^q$lac P$_{L8}$ | | | |
| E183 | ampC::(P$_{trpB}$λcI+) | P$_{lacI}$$^q$(ΔlacI-lacZ)$_{158}$lacY+ | | | |
| E205 | ampC::(P$_{trpB}$λcI+) | P$_{lacI}$$^q$(ΔlacI-lacZ)$_{158}$lacY+ | ΔwcaJ | | |
| E214 | ampC::(P$_{trpB}$λcI+) | P$_{lacI}$$^q$(ΔlacI-lacZ)$_{158}$lacY+ | ΔwcaJ | thyA$_{748}$::Tn10 | |
| E390 | ampC::(P$_{trpB}$λcI+) | P$_{lacI}$$^q$(ΔlacI-lacZ)$_{158}$lacY+ | ΔwcaJ | thyA$_{748}$::Tn10 | Δlon::(kan,lacZ+) |
| E403 | ampC::(P$_{trpB}$λcI+) | P$_{lacI}$$^q$(ΔlacI-lacZ)$_{158}$lacY+ | ΔwcaJ | thyA$_{748}$::Tn10 | Δlon::(kan,lacZ+) ΔlacA |

FIG. 14

BIOSYNTHESIS OF HUMAN MILK OLIGOSACCHARIDES IN ENGINEERED BACTERIA

RELATED APPLICATIONS

This application is a continuation of U.S. Ser. No. 15/442,131, filed Feb. 24, 2017, which is a continuation of U.S. Ser. No. 14/033,664 filed Sep. 23, 2013, now U.S. Pat. No. 9,587,241 issued Feb. 15, 2017, which is a divisional of U.S. Ser. No. 13/398,526 filed Feb. 16, 2012, now U.S. Pat. No. 9,453,230 issued Sep. 27, 2016, and claims the benefit of priority under 35 U.S.C. § 119(e) to U.S. Provisional Application No: 61/443,470, filed Feb. 16, 2011, the entire contents of each of which are incorporated herein by reference.

INCORPORATED-BY-REFERENCE OF SEQUENCE LISTING

The contents of the text file named "037847_505C04US_Sequence_Listing.txt", which was created on May 15, 2018 and is 94 KB in size, are hereby incorporated by reference in their entirety.

FIELD OF THE INVENTION

The invention provides compositions and methods for producing purified oligosaccharides, in particular certain fucosylated and/or sialylated oligosaccharides that are typically found in human milk.

BACKGROUND OF THE INVENTION

Human milk contains a diverse and abundant set of neutral and acidic oligosaccharides (human milk oligosaccharides, HMOS). Many of these molecules are not utilized directly by infants for nutrition, but they nevertheless serve critical roles in the establishment of a healthy gut microbiome, in the prevention of disease, and in immune function. Prior to the invention described herein, the ability to produce HMOS inexpensively at large scale was problematic. For example, HMOS production through chemical synthesis was limited by stereo-specificity issues, precursor availability, product impurities, and high overall cost. As such, there is a pressing need for new strategies to inexpensively manufacture large quantities of HMOS for a variety of commercial applications.

SUMMARY OF THE INVENTION

The invention described herein features efficient and economical methods for producing fucosylated and sialylated oligosaccharides. The method for producing a fucosylated oligosaccharide in a bacterium comprises the following steps: providing a bacterium that comprises a functional β-galactosidase gene, an exogenous fucosyltransferase gene, a GDP-fucose synthesis pathway, and a functional lactose permease gene; culturing the bacterium in the presence of lactose; and retrieving a fucosylated oligosaccharide from the bacterium or from a culture supernatant of the bacterium.

To produce a fucosylated oligosaccharide by biosynthesis, the bacterium utilizes an endogenous or exogenous guanosine diphosphate (GDP)-fucose synthesis pathway. By "GDP-fucose synthesis pathway" is meant a sequence of reactions, usually controlled and catalyzed by enzymes, which results in the synthesis of GDP-fucose. An exemplary GDP-fucose synthesis pathway in Escherichia coli is set forth below. In the GDP-fucose synthesis pathway set forth below, the enzymes for GDP-fucose synthesis include: 1) manA=phosphomannose isomerase (PMI), 2) manB=phosphomannomutase (PMM), 3) manC=mannose-1-phosphate guanylyltransferase (GMP), 4) gmd=GDP-mannose-4,6-dehydratase (GMD), 5) fcl=GDP-fucose synthase (GFS), and 6) Δwcaf=mutated UDP-glucose lipid carrier transferase.

Glucose→Glc-6-P→Fru-6-P→$^1$Man-6-P→$^2$Man-1-P→$^3$GDP-Man→$^{4,5}$GDP-Fuc 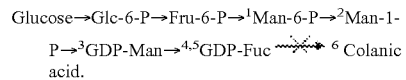 $^6$ Colanic acid.

The synthetic pathway from fructose-6-phosphate, a common metabolic intermediate of all organisms, to GDP-fucose consists of 5 enzymatic steps: 1) PMI (phosphomannose isomerase), 2) PMM (phosphomannomutase), 3) GMP (mannose-1-phosphate guanylyltransferase), 4) GMD (GDP-mannose-4,6-dehydratase), and 5) GFS (GDP-fucose synthase). Individual bacterial species possess different inherent capabilities with respect to GDP-fucose synthesis. Escherichia coli, for example, contains enzymes competent to perform all five steps, whereas Bacillus licheniformis is missing enzymes capable of performing steps 4 and 5 (i.e., GMD and GFS). Any enzymes in the GDP-synthesis pathway that are inherently missing in any particular bacterial species are provided as genes on recombinant DNA constructs, supplied either on a plasmid expression vector or as exogenous genes integrated into the host chromosome.

The invention described herein details the manipulation of genes and pathways within bacteria such as the enterobacterium Escherichia coli K12 (E. coli) or probiotic bacteria leading to high level synthesis of HMOS. A variety of bacterial species may be used in the oligosaccharide biosynthesis methods, for example Erwinia herbicola (Pantoea agglomerans), Citrobacter freundii, Pantoea citrea, Pectobacterium carotovorum, or Xanthomonas campestris. Bacteria of the genus Bacillus may also be used, including Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, and Bacillus circulans. Similarly, bacteria of the genera Lactobacillus and Lactococcus may be modified using the methods of this invention, including but not limited to Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, and Lactococcus lactis. Streptococcus thermophiles and Proprionibacterium freudenreichii are also suitable bacterial species for the invention described herein. Also included as part of this invention are strains, modified as described here, from the genera Enterococcus (e.g., Enterococcus faecium and Enterococcus thermophiles), Bifidobacterium (e.g., Bifidobacterium longum, Bifidobacterium infantis, and Bifidobacterium bifidum), Sporolactobacillus spp., Micromomospora spp., Micrococcus spp., Rhodococcus spp., and Pseudomonas (e.g., Pseudomonas fluorescens and Pseudomonas aeruginosa). Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

The bacterium also comprises a functional β-galactosidase gene. The β-galactosidase gene is an endogenous β-galactosidase gene or an exogenous β-galactosidase gene. For example, the β-galactosidase gene comprises an *E. coli* lacZ gene (e.g., GenBank Accession Number V00296 (GI: 41901), incorporated herein by reference). The bacterium accumulates an increased intracellular lactose pool, and produces a low level of β-galactosidase.

A functional lactose permease gene is also present in the bacterium. The lactose permease gene is an endogenous lactose permease gene or an exogenous lactose permease gene. For example, the lactose permease gene comprises an *E. coli* lacY gene (e.g., GenBank Accession Number V00295 (GI:41897), incorporated herein by reference). Many bacteria possess the inherent ability to transport lactose from the growth medium into the cell, by utilizing a transport protein that is either a homolog of the *E. coli* lactose permease (e.g., as found in *Bacillus licheniformis*), or a transporter that is a member of the ubiquitous PTS sugar transport family (e.g., as found in *Lactobacillus casei* and *Lactobacillus rhamnosus*). For bacteria lacking an inherent ability to transport extracellular lactose into the cell cytoplasm, this ability is conferred by an exogenous lactose transporter gene (e.g., *E. coli* lacY) provided on recombinant DNA constructs, and supplied either on a plasmid expression vector or as exogenous genes integrated into the host chromosome.

The bacterium comprises an exogenous fucosyltransferase gene. For example, the exogenous fucosyltransferase gene encodes α(1,2) fucosyltransferase and/or α(1,3) fucosyltransferase. An exemplary α(1,2) fucosyltransferase gene is the wcfW gene from *Bacteroides fragilis* NCTC 9343 (SEQ ID NO: 4). An exemplary α(1,3) fucosyltransferase gene is the *Helicobacter pylori* 26695 futA gene. One example of the *Helicobacter pylori* futA gene is presented in GenBank Accession Number HV532291 (GI:365791177), incorporated herein by reference.

Alternatively, a method for producing a fucosylated oligosaccharide by biosynthesis comprises the following steps: providing an enteric bacterium that comprises a functional β-galactosidase gene, an exogenous fucosyltransferase gene, a mutation in a colanic acid synthesis gene, and a functional lactose permease gene; culturing the bacterium in the presence of lactose; and retrieving a fucosylated oligosaccharide from the bacterium or from a culture supernatant of the bacterium.

To produce a fucosylated oligosaccharide by biosynthesis, the bacterium comprises a mutation in an endogenous colanic acid (a fucose-containing exopolysaccharide) synthesis gene. By "colanic acid synthesis gene" is meant a gene involved in a sequence of reactions, usually controlled and catalyzed by enzymes that result in the synthesis of colanic acid. Exemplary colanic acid synthesis genes include an rcsA gene (e.g., GenBank Accession Number M58003 (GI: 1103316), incorporated herein by reference), an rcsB gene, (e.g., GenBank Accession Number E04821 (GI:2173017), incorporated herein by reference), a wcaJ gene, (e.g., GenBank Accession Number (amino acid) BAA15900 (GI: 1736749), incorporated herein by reference), a wzxC gene, (e.g., GenBank Accession Number (amino acid) BAA15899 (GI:1736748), incorporated herein by reference), a wcaD gene, (e.g., GenBank Accession Number (amino acid) BAE76573 (GI:85675202), incorporated herein by reference), a wza gene, (e.g., GenBank Accession Number (amino acid) BAE76576 (GI:85675205), incorporated herein by reference), a wzb gene, and (e.g., GenBank Accession Number (amino acid) BAE76575 (GI:85675204), incorporated herein by reference), and a wzc gene (e.g., GenBank Accession Number (amino acid) BAA15913 (GI: 1736763), incorporated herein by reference).

This is achieved through a number of genetic modifications of endogenous *E. coli* genes involved either directly in colanic acid precursor biosynthesis, or in overall control of the colanic acid synthetic regulon. Specifically, the ability of the host *E. coli* strain to synthesize colanic acid, an extracellular capsular polysaccharide, is eliminated by the deletion of the wcaJ gene, encoding the UDP-glucose lipid carrier transferase. In a wcaJ null background, GDP-fucose accumulates in the *E. coli* cytoplasm. Over-expression of a positive regulator protein, RcsA, in the colanic acid synthesis pathway results in an increase in intracellular GDP-fucose levels. Over-expression of an additional positive regulator of colanic acid biosynthesis, namely RcsB, is also utilized, either instead of or in addition to over-expression of RcsA, to increase intracellular GDP-fucose levels. Alternatively, colanic acid biosynthesis is increased following the introduction of a null mutation into the *E. coli* lon gene (e.g., GenBank Accession Number L20572 (GI:304907), incorporated herein by reference). Lon is an adenosine-5'-triphosphate (ATP)-dependant intracellular protease that is responsible for degrading RcsA, mentioned above as a positive transcriptional regulator of colanic acid biosynthesis in *E. coli*. In a lon null background, RcsA is stabilized, RcsA levels increase, the genes responsible for GDP-fucose synthesis in *E. coli* are up-regulated, and intracellular GDP-fucose concentrations are enhanced.

For example, the bacterium further comprises a functional, wild-type *E. coli* lacZ$^+$ gene inserted into an endogenous gene, for example the lon gene in *E. coli*. In this manner, the bacterium may comprise a mutation in a lon gene.

The bacterium also comprises a functional β-galactosidase gene. The β-galactosidase gene is an endogenous β-galactosidase gene or an exogenous β-galactosidase gene. For example, the β-galactosidase gene comprises an *E. coli* lacZ gene. The endogenous lacZ gene of the *E. coli* is deleted or functionally inactivated, but in such a way that expression of the downstream lactose permease (lacY) gene remains intact.

The bacterium comprises an exogenous fucosyltransferase gene. For example, the exogenous fucosyltransferase gene encodes α(1,2) fucosyltransferase and/or α(1,3) fucosyltransferase. An exemplary α(1,2) fucosyltransferase gene is the wcfW gene from *Bacteroides fragilis* NCTC 9343 (SEQ ID NO: 4). An exemplary α(1,3) fucosyltransferase gene is the *Helicobacter pylori* 26695 futA gene. One example of the *Helicobacter pylori* futA gene is presented in GenBank Accession Number HV532291 (GI:365791177), incorporated herein by reference.

A functional lactose permease gene is also present in the bacterium. The lactose permease gene is an endogenous lactose permease gene or an exogenous lactose permease gene. For example, the lactose permease gene comprises an *E. coli* lacY gene.

The bacterium may further comprise an exogenous rcsA and/or rcsB gene (e.g., in an ectopic nucleic acid construct such as a plasmid), and the bacterium optionally further comprises a mutation in a lacA gene (e.g., GenBank Accession Number X51872 (GI:41891), incorporated herein by reference).

Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

The bacteria used herein to produce HMOS are genetically engineered to comprise an increased intracellular guanosine diphosphate (GDP)-fucose pool, an increased intracellular lactose pool (as compared to wild type) and to comprise fucosyl transferase activity. Accordingly, the bacterium contains a mutation in a colanic acid (a fucose-containing exopolysaccharide) synthesis pathway gene, such as a wcaJ gene, resulting in an enhanced intracellular GDP-fucose pool. The bacterium further comprises a functional, wild-type *E. coli* lacZ⁺ gene inserted into an endogenous gene, for example the lon gene in *E. coli*. In this manner, the bacterium may further comprise a mutation in a lon gene. The endogenous lacZ gene of the *E. coli* is deleted or functionally inactivated, but in such a way that expression of the downstream lactose permease (lacY) gene remains intact. The organism so manipulated maintains the ability to transport lactose from the growth medium, and to develop an intracellular lactose pool for use as an acceptor sugar in oligosaccharide synthesis, while also maintaining a low level of intracellular beta-galactosidase activity useful for a variety of additional purposes. The bacterium may further comprise an exogenous rcsA and/or rcsB gene (e.g., in an ectopic nucleic acid construct such as a plasmid), and the bacterium optionally further comprises a mutation in a lacA gene. Preferably, the bacterium accumulates an increased intracellular lactose pool, and produces a low level of beta-galactosidase.

The bacterium possesses fucosyl transferase activity. For example, the bacterium comprises one or both of an exogenous fucosyltransferase gene encoding an α(1,2) fucosyltransferase and an exogenous fucosyltransferase gene encoding an α(1,3) fucosyltransferase. An exemplary α(1,2) fucosyltransferase gene is the wcfW gene from *Bacteroides fragilis* NCTC 9343 (SEQ ID NO: 4). Prior to the present invention, this wcfW gene was not known to encode a protein with an α(1,2) fucosyltransferase activity, and further was not suspected to possess the ability to utilize lactose as an acceptor sugar. Other α(1,2) fucosyltransferase genes that use lactose as an acceptor sugar (e.g., the *Helicobacter pylori* 26695 futC gene or the *E. coli* O128:B12 wbsJ gene) may readily be substituted for *Bacteroides fragilis* wcfW. One example of the *Helicobacter pylori* futC gene is presented in GenBank Accession Number EF452503 (GI: 134142866), incorporated herein by reference.

An exemplary α(1,3) fucosyltransferase gene is the *Helicobacter pylori* 26695 futA gene, although other α(1,3) fucosyltransferase genes known in the art may be substituted (e.g., α(1,3) fucosyltransferase genes from *Helicobacter hepaticus* Hh0072, *Helicobacter bilis*, *Campylobacter jejuni*, or from *Bacteroides* species). The invention includes a nucleic acid construct comprising one, two, three or more of the genes described above. For example, the invention includes a nucleic acid construct expressing an exogenous fucosyltransferase gene (encoding α(1,2) fucosyltransferase or α(1,3) fucosyltransferase) transformed into a bacterial host strain comprising a deleted endogenous β-galactosidase (e.g., lacZ) gene, a replacement functional β-galactosidase gene of low activity, a GDP-fucose synthesis pathway, a functional lactose permease gene, and a deleted lactose acetyltransferase gene.

Also within the invention is an isolated *E. coli* bacterium as described above and characterized as comprising a defective colanic acid synthesis pathway, a reduced level of β-galactosidase (LacZ) activity, and an exogenous fucosyl transferase gene. The invention also includes: a) methods for phenotypic marking of a gene locus in a β-galactosidase negative host cell by utilizing a β-galactosidase (e.g., lacZ) gene insert engineered to produce a low but readily detectable level of β-galactosidase activity, b) methods for readily detecting lytic bacteriophage contamination in fermentation runs through release and detection of cytoplasmic β-galactosidase in the cell culture medium, and c) methods for depleting a bacterial culture of residual lactose at the end of production runs. a), b) and c) are each achieved by utilizing a functional β-galactosidase (e.g., lacZ) gene insert carefully engineered to direct the expression of a low, but detectable level of β-galactosidase activity in an otherwise β-galactosidase negative host cell.

A purified fucosylated oligosaccharide produced by the methods described above is also within the invention. A purified oligosaccharide, e.g., 2'-FL, 3FL, LDFT, is one that is at least 90%, 95%, 98%, 99%, or 100% (w/w) of the desired oligosaccharide by weight.

Purity is assessed by any known method, e.g., thin layer chromatography or other electrophoretic or chromatographic techniques known in the art. The invention includes a method of purifying a fucosylated oligosaccharide produced by the genetically engineered bacterium described above, which method comprises separating the desired fucosylated oligosaccharide (e.g., 2'-FL) from contaminants in a bacterial cell extract or lysate, or bacterial cell culture supernatant. Contaminants include bacterial DNA, protein and cell wall components, and yellow/brown sugar caramels sometimes formed in spontaneous chemical reactions in the culture medium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprising purified 2'-fucosyllactose (2'-FL), 3-fucosyllactose (3FL), lactodifucotetraose (LDFT), or 3'-sialyl-3-fucosyllactose (3'-S3FL) and an excipient is suitable for oral administration. Large quantities of 2'-FL, 3FL, LDFT, or 3'-S3FL are produced in bacterial hosts, e.g., an *E. coli* bacterium comprising a heterologous α(1,2)fucosyltransferase, a heterologous α(1,3) fucosyltransferase, or a heterologous sialyltransferase, or a combination thereof. An *E. coli* bacterium comprising an enhanced cytoplasmic pool of each of the following: lactose, GDP-fucose, and CMP-Neu5Ac, is useful in such production systems. In the case of lactose and GDP-fucose, endogenous *E. coli* metabolic pathways and genes are manipulated in ways that result in the generation of increased cytoplasmic concentrations of lactose and/or GDP-fucose, as compared to levels found in wild type *E. coli*. For example, the bacteria contain at least 10%, 20%, 50%, 2×, 5×, 10× or more of the levels in a corresponding wild type bacteria that lacks the genetic modifications described above. In the case of CMP-Neu5Ac, endogenous Neu5Ac catabolism genes are inactivated and exogenous CMP-Neu5Ac biosynthesis genes introduced into *E. coli* resulting in the generation of a cytoplasmic pool of CMP-Neu5Ac not found in the wild type bacterium. A method of producing a pharmaceutical composition comprising a purified HMOS is carried out by culturing the bacterium described above, purifying the HMOS produced by the bacterium, and combining the HMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease.

The invention therefore provides methods for increasing intracellular levels of GDP-fucose in *Escherichia coli* by manipulating the organism's endogenous colanic acid biosynthesis pathway. This is achieved through a number of genetic modifications of endogenous *E. coli* genes involved either directly in colanic acid precursor biosynthesis, or in overall control of the colanic acid synthetic regulon. The invention also provides for increasing the intracellular concentration of lactose in *E. coli*, for cells grown in the presence of lactose, by using manipulations of endogenous *E. coli* genes involved in lactose import, export, and catabolism. In particular, described herein are methods of increasing intracellular lactose levels in *E. coli* genetically engineered to produce a human milk oligosaccharide by incorporating a lacA mutation into the genetically modified *E. coli*. The lacA mutation prevents the formation of intracellular acetyl-lactose, which not only removes this molecule as a contaminant from subsequent purifications, but also eliminates *E. coli*'s ability to export excess lactose from its cytoplasm, thus greatly facilitating purposeful manipulations of the *E. coli* intracellular lactose pool.

Also described herein are bacterial host cells with the ability to accumulate a intracellular lactose pool while simultaneously possessing low, functional levels of cytoplasmic β-galactosidase activity, for example as provided by the introduction of a functional recombinant *E. coli* lacZ gene, or by a β-galactosidase gene from any of a number of other organisms (e.g., the lac4 gene of *Kluyveromyces lactis* (e.g., GenBank Accession Number M84410 (GI:173304), incorporated herein by reference). Low, functional levels of cytoplasmic β-galactosidase include β-galactosidase activity levels of between 0.05 and 200 units, e.g., between 0.05 and 5 units, between 0.05 and 4 units, between 0.05 and 3 units, or between 0.05 and 2 units (for unit definition see: Miller J H, Laboratory CSH. Experiments in molecular genetics. Cold Spring Harbor Laboratory Cold Spring Harbor, N.Y.; 1972; incorporated herein by reference). This low level of cytoplasmic β-galactosidase activity, while not high enough to significantly diminish the intracellular lactose pool, is nevertheless very useful for tasks such as phenotypic marking of desirable genetic loci during construction of host cell backgrounds, for detection of cell lysis due to undesired bacteriophage contaminations in fermentation processes, or for the facile removal of undesired residual lactose at the end of fermentations.

In one aspect, the human milk oligosaccharide produced by engineered bacteria comprising an exogenous nucleic acid molecule encoding an α(1,2) fucosyltransferase, is 2′-FL (2′-fucosyllactose). Preferably, the α(1,2)fucosyltransferase utilized is the previously completely uncharacterized wcfW gene from *Bacteroides fragilis* NCTC 9343 of the present invention, alternatively the futC gene of *Helicobacter pylori* 26695 or the wbsJ gene of *E. coli* strain O128:B12, or any other α(1,2) fucosyltransferase capable of using lactose as the sugar acceptor substrate may be utilized for 2′-FL synthesis. In another aspect the human milk oligosaccharide produced by engineered bacteria comprising an exogenous nucleic acid molecule encoding an α(1,3) fucosyltransferase, is 3FL (3-fucosyllactose), wherein the bacterial cell comprises an exogenous nucleic acid molecule encoding an exogenous α(1,3) fucosyltransferase. Preferably, the bacterial cell is *E. coli*. The exogenous α(1,3) fucosyltransferase is isolated from, e.g., *Helicobacter pylori*, *H. hepaticus*, *H. bilis*, *C. jejuni*, or a species of *Bacteroides*.

In one aspect, the exogenous α(1,3) fucosyltransferase comprises *H. hepaticus* Hh0072, *H. pylori* 11639 FucTa, or *H. pylori* UA948 FucTa (e.g., GenBank Accession Number AF194963 (GI:28436396), incorporated herein by reference). The invention also provides compositions comprising *E. coli* genetically engineered to produce the human milk tetrasaccharide lactodifucotetraose (LDFT). The *E. coli* in this instance comprise an exogenous nucleic acid molecule encoding an α(1,2) fucosyltransferase and an exogenous nucleic acid molecule encoding an α(1,3) fucosyltransferase. In one aspect, the *E. coli* is transformed with a plasmid expressing an α(1,2) fucosyltransferase and/or a plasmid expressing an α(1,3) fucosyltransferase. In another aspect, the *E. coli* is transformed with a plasmid that expresses both an α(1,2) fucosyltransferase and an α(1,3) fucosyltransferase. Alternatively, the *E. coli* is transformed with a chromosomal integrant expressing an α(1,2) fucosyltransferase and a chromosomal integrant expressing an α(1,3) fucosyltransferase. Optionally, the *E. coli* is transformed with plasmid pG177.

Also described herein are compositions comprising a bacterial cell that produces the human milk oligosaccharide 3′-S3FL (3′-sialyl-3-fucosyllactose), wherein the bacterial cell comprises an exogenous sialyl-transferase gene encoding α(2,3)sialyl-transferase and an exogenous fucosyltransferase gene encoding α(1,3) fucosyltransferase. Preferably, the bacterial cell is *E. coli*. The exogenous fucosyltransferase gene is isolated from, e.g., *Helicobacter pylori*, *H. hepaticus*, *H. bilis*, *C. jejuni*, or a species of *Bacteroides*. For example, the exogenous fucosyltransferase gene comprises *H. hepaticus* Hh0072, *H. pylori* 11639 FucTa, or *H. pylori* UA948 FucTa. The exogenous sialyltransferase gene utilized for 3′-S3FL production may be obtained from any one of a number of sources, e.g., those described from *N. meningitidis* and *N. gonorrhoeae*. Preferably, the bacterium comprises a GDP-fucose synthesis pathway.

Additionally, the bacterium contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway in *Escherichia coli* is described herein. In the sialic acid catabolic pathway described herein, sialic acid (Neu5Ac; N-acetylneuraminic acid) is degraded by the enzymes NanA (N-acetylneuraminic acid lyase) and NanK (N-acetylmannosamine kinase). For example, a deficient sialic acid catabolic pathway is engineered in *Escherichia coli* by way of a null mutation in endogenous nanA (N-acetylneuraminate lyase) (e.g., GenBank Accession Number D00067 (GI: 216588), incorporated herein by reference) and/or nanK (N-acetylmannosamine kinase) genes (e.g., GenBank Accession Number (amino acid) BAE77265 (GI:85676015), incorporated herein by reference). Other components of sialic acid metabolism include: (nanT) sialic acid transporter; (ManNAc-6-P) N-acetylmannosamine-6-phosphate; (GlcNAc-6-P) N-acetylglucosamine-6-phosphate; (GlcN-6-P) Glucosamine-6-phosphate; and (Fruc-6-P) Fructose-6-phosphate.

Moreover, the bacterium (e.g., *E. coli*) also comprises a sialic acid synthetic capability. For example, the bacterium comprises a sialic acid synthetic capability through provision of an exogenous UDP-GlcNAc 2-epimerase (e.g., neuC of *Campylobacter jejuni* or equivalent (e.g., GenBank Accession Number (amino acid) AAG29921 (GI: 11095585), incorporated herein by reference)), a Neu5Ac synthase (e.g., neuB of *C. jejuni* or equivalent, e.g., GenBank Accession Number (amino acid) AAG29920 (GI:

11095584), incorporated herein by reference)), and/or a CMP-Neu5Ac synthetase (e.g., neuA of *C. jejuni* or equivalent, e.g., GenBank Accession Number (amino acid) ADN91474 (GI:307748204), incorporated herein by reference).

Additionally, the bacterium also comprises a functional β-galactosidase gene and a functional lactose permease gene. Bacteria comprising the characteristics described herein are cultured in the presence of lactose, and a 3'-sialyl-3-fucosyllactose is retrieved, either from the bacterium itself or from a culture supernatant of the bacterium.

Also provided are methods for producing a 3'-sialyl-3-fucosyllactose (3'-S3FL) in an enteric bacterium, wherein the enteric bacterium comprises a mutation in an endogenous colanic acid synthesis gene, a functional lacZ gene, a functional lactose permease gene, an exogenous fucosyltransferase gene encoding α(1,3) fucosyltransferase, and an exogenous sialyltransferase gene encoding an α(2,3)sialyl transferase. Additionally, the bacterium contains a deficient sialic acid catabolic pathway. For example, the bacterium comprises a deficient sialic acid catabolic pathway by way of a null mutation in endogenous nanA (N-acetylneuraminate lyase) and/or nanK (N-acetylmannosamine kinase) genes. The bacterium also comprises a sialic acid synthetic capability. For example, the bacterium comprises a sialic acid synthetic capability through provision of an exogenous UDP-GlcNAc 2-epimerase (e.g., neuC of *C. jejuni* or equivalent), a Neu5Ac synthase (e.g., neuB of *C. jejuni* or equivalent), and/or a CMP-Neu5Ac synthetase (e.g., neuA of *C. jejuni* or equivalent). Bacteria comprising the characteristics described herein are cultured in the presence of lactose, and a 3'-sialyl-3-fucosyllactose is retrieved, either from the bacterium itself or from a culture supernatant of the bacterium.

Also provided is a method for phenotypic marking of a gene locus in a host cell, whose native β-galactosidase gene is deleted or inactivated, by utilizing an inserted recombinant β-galactosidase (e.g., lacZ) gene engineered to produce a low, but detectable level of β-galactosidase activity. Similarly, the invention also provides methods for depleting a bacterial culture of residual lactose in a β-galactosidase negative host cell, whose native β-galactosidase gene is deleted or inactivated, by utilizing an inserted recombinant β-galactosidase (e.g., lacZ) gene engineered to produce a low but detectable level of β-galactosidase activity. Finally, also provided is a method for detecting bacterial cell lysis in a culture of a β-galactosidase negative host cell, whose native β-galactosidase gene is deleted or inactivated, by utilizing an inserted recombinant β-galactosidase (e.g., lacZ) gene engineered to produce a low but detectable level of β-galactosidase activity.

Methods of purifying a fucosylated oligosaccharide produced by the methods described herein are carried out by binding the fucosylated oligosaccharide from a bacterial cell lysate or bacterial cell culture supernatant of the bacterium to a carbon column, and eluting the fucosylated oligosaccharide from the column. Purified fucosylated oligosaccharide are produced by the methods described herein.

Optionally, the invention features a vector, e.g., a vector containing a nucleic acid. The vector can further include one or more regulatory elements, e.g., a heterologous promoter. The regulatory elements can be operably linked to a protein gene, fusion protein gene, or a series of genes linked in an operon in order to express the fusion protein. In yet another aspect, the invention comprises an isolated recombinant cell, e.g., a bacterial cell containing an aforementioned nucleic acid molecule or vector. The nucleic acid sequence can be optionally integrated into the genome.

The term "substantially pure" in reference to a given polypeptide, polynucleotide or oligosaccharide means that the polypeptide, polynucleotide or oligosaccharide is substantially free from other biological macromolecules. The substantially pure polypeptide, polynucleotide or oligosaccharide is at least 75% (e.g., at least 80, 85, 95, or 99%) pure by dry weight. Purity can be measured by any appropriate calibrated standard method, for example, by column chromatography, polyacrylamide gel electrophoresis, thin layer chromatography (TLC) or HPLC analysis.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, Purified HMOS compositions are at least 60% by weight (dry weight) the compound of interest. Preferably, the preparation is at least 75%, more preferably at least 90%, and most preferably at least 99%, by weight the compound of interest. Purity is measured by any appropriate calibrated standard method, for example, by column chromatography, polyacrylamide gel electrophoresis, thin layer chromatography (TLC) or HPLC analysis. For example, a "purified protein" refers to a protein that has been separated from other proteins, lipids, and nucleic acids with which it is naturally associated. Preferably, the protein constitutes at least 10, 20, 50 70, 80, 90, 95, 99-100% by dry weight of the purified preparation.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

A "heterologous promoter", when operably linked to a nucleic acid sequence, refers to a promoter which is not naturally associated with the nucleic acid sequence.

The terms "express" and "over-express" are used to denote the fact that, in some cases, a cell useful in the method herein may inherently express some of the factor that it is to be genetically altered to produce, in which case the addition of the polynucleotide sequence results in over-expression of the factor. That is, more factor is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

The invention provides a method of treating, preventing, or reducing the risk of infection in a subject comprising administering to said subject a composition comprising a human milk oligosaccharide, purified from a culture of a recombinant strain of the current invention, wherein the HMOS binds to a pathogen and wherein the subject is infected with or at risk of infection with the pathogen. In one aspect, the infection is caused by a Norwalk-like virus or *Campylobacter jejuni*. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified HMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations intended to enhance the growth of beneficial microorganisms either in vitro or in vivo. For example, the purified sugar (e.g., 2'-FL) can be mixed with a *Bifidobacterium* or *Lactobacillus* in a probiotic nutritional composition. (i.e. *Bifidobacteria* are beneficial components of a normal human gut flora and are also known to utilize HMOS for growth.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Figure 12:
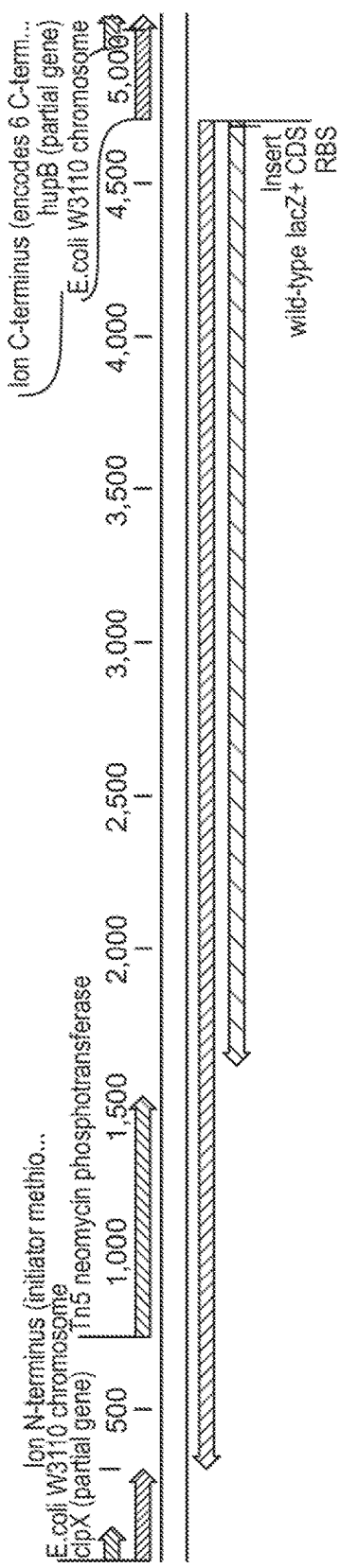

FIG. 12 is a diagram showing the replacement of the lon gene in *E. coli* strain E390 by a DNA fragment carrying both a kanamycin resistance gene (derived from transposon Tn5) and a wild-type *E. coli* lacZ+ coding sequence.

FIG. 13A-E is a DNA sequence with annotations (in GenBank format) of the DNA insertion into the lon region diagrammed in FIG. 12 (SEQ ID NOs 9-15).

FIG. 14 is a table containing the genotypes of several *E. coli* strains of the current invention.

Figure 15:
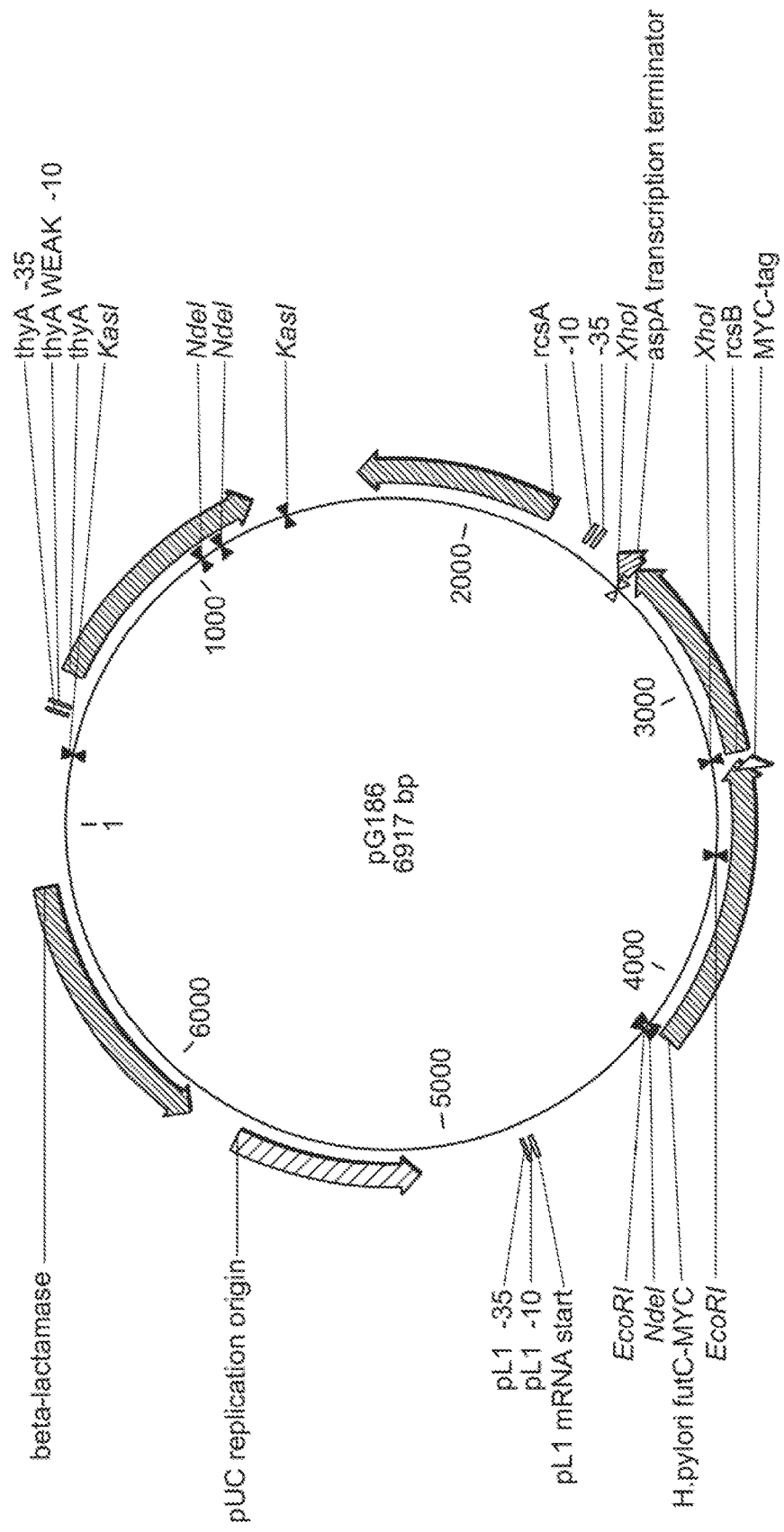

FIG. 15 is a plasmid map of pG186, which expresses the a(1,2)fucosyltransferase gene futC in an operon with the colanic acid pathway transcription activator gene rcsB.

Figure 16:
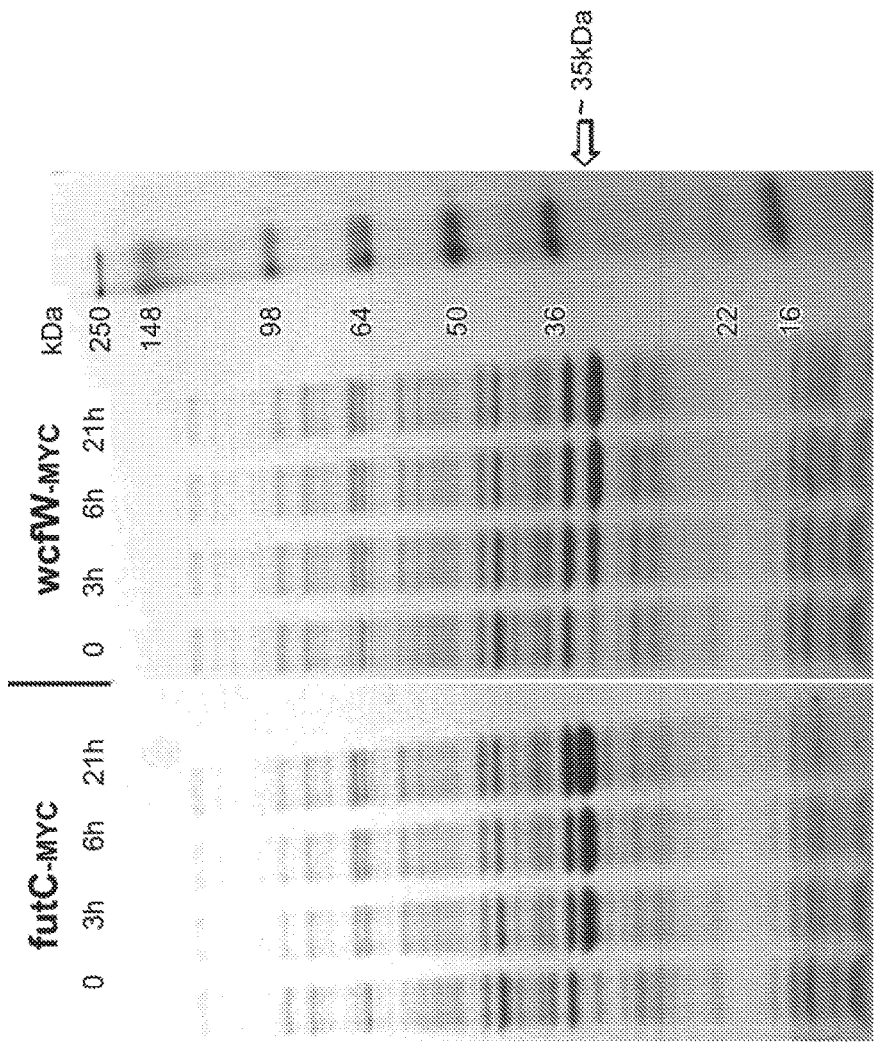

FIG. 16 is a photograph of a western blot of lysates of *E. coli* containing pG180, a pG175 derivative plasmid carrying the *B. fragilis* wcfW gene in place of wbsJ and which expresses wcfW, and of cells containing pG171, a pG175 derivative plasmid carrying the *H. pylori* 26695 futC gene in place of wbsJ and which expresses futC.

Figure 17:
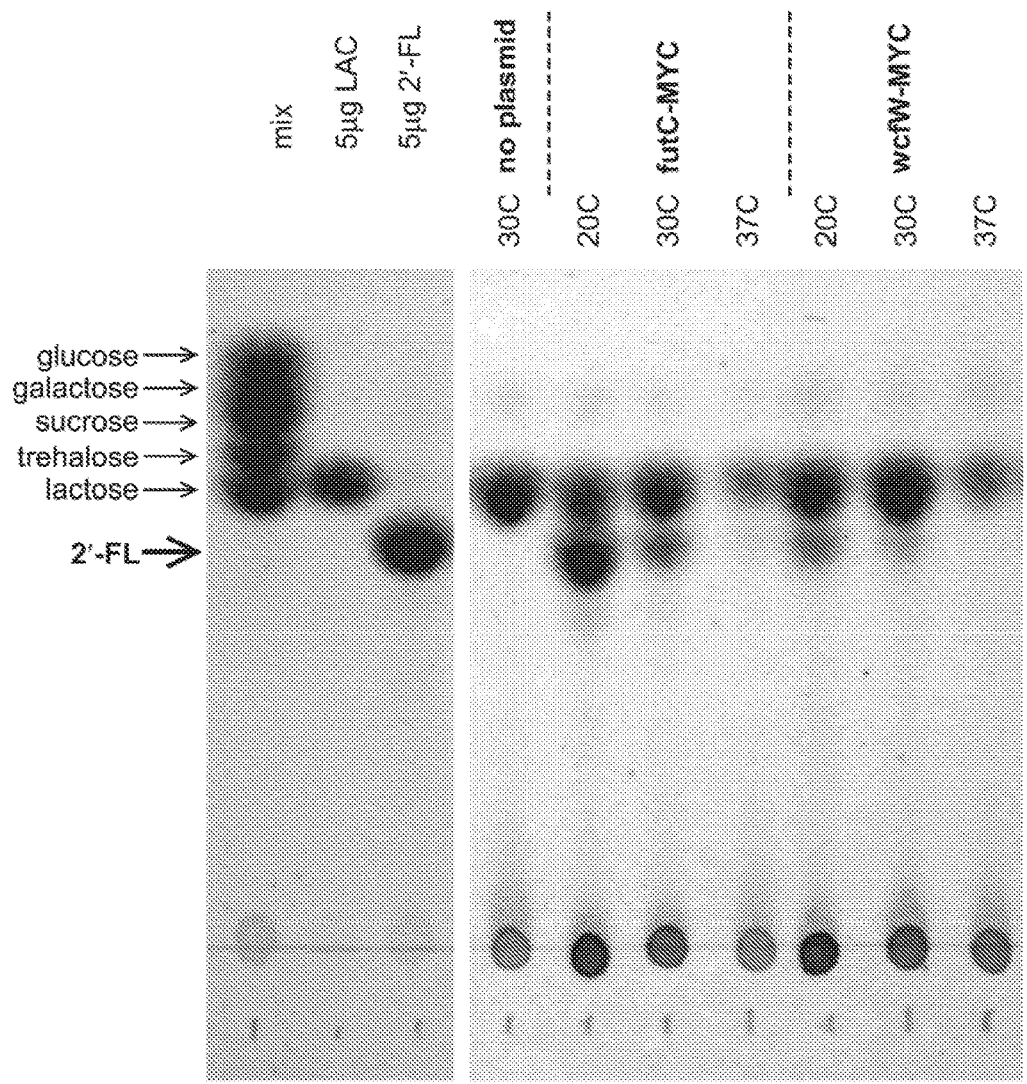

FIG. 17 is a photograph of a thin layer chromatogram of 2'-FL produced in *E. coli* by cells carrying plasmids pG180 or pG171 and induced for expression of wcfW or futC respectively.

Figure 18:
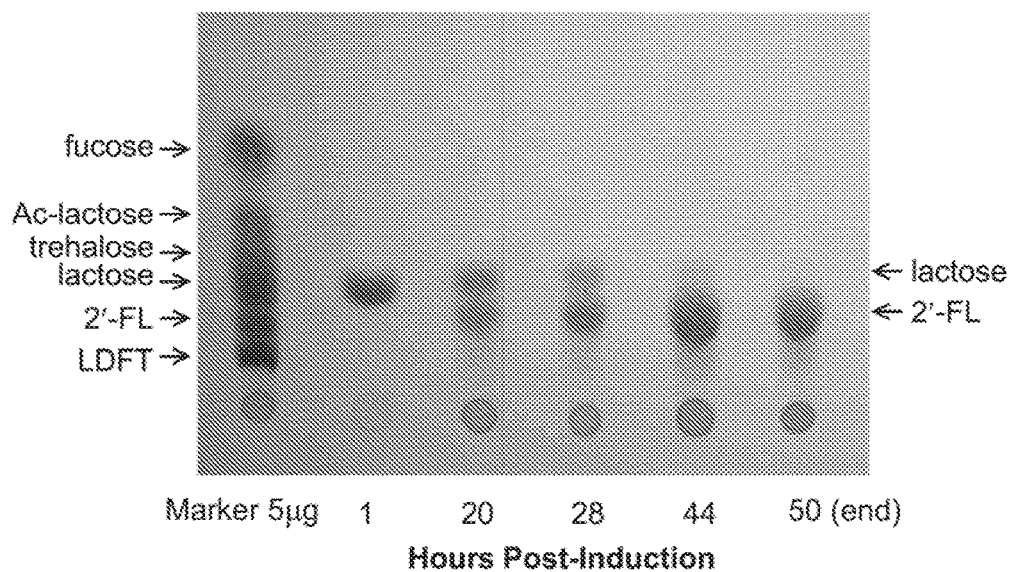

FIG. 18 is a photograph of a thin layer chromatogram showing the kinetics and extent of 2'-FL production in a 10 L bioreactor of *E. coli* host strain E403 transformed with plasmid pG171.

Figure 19:
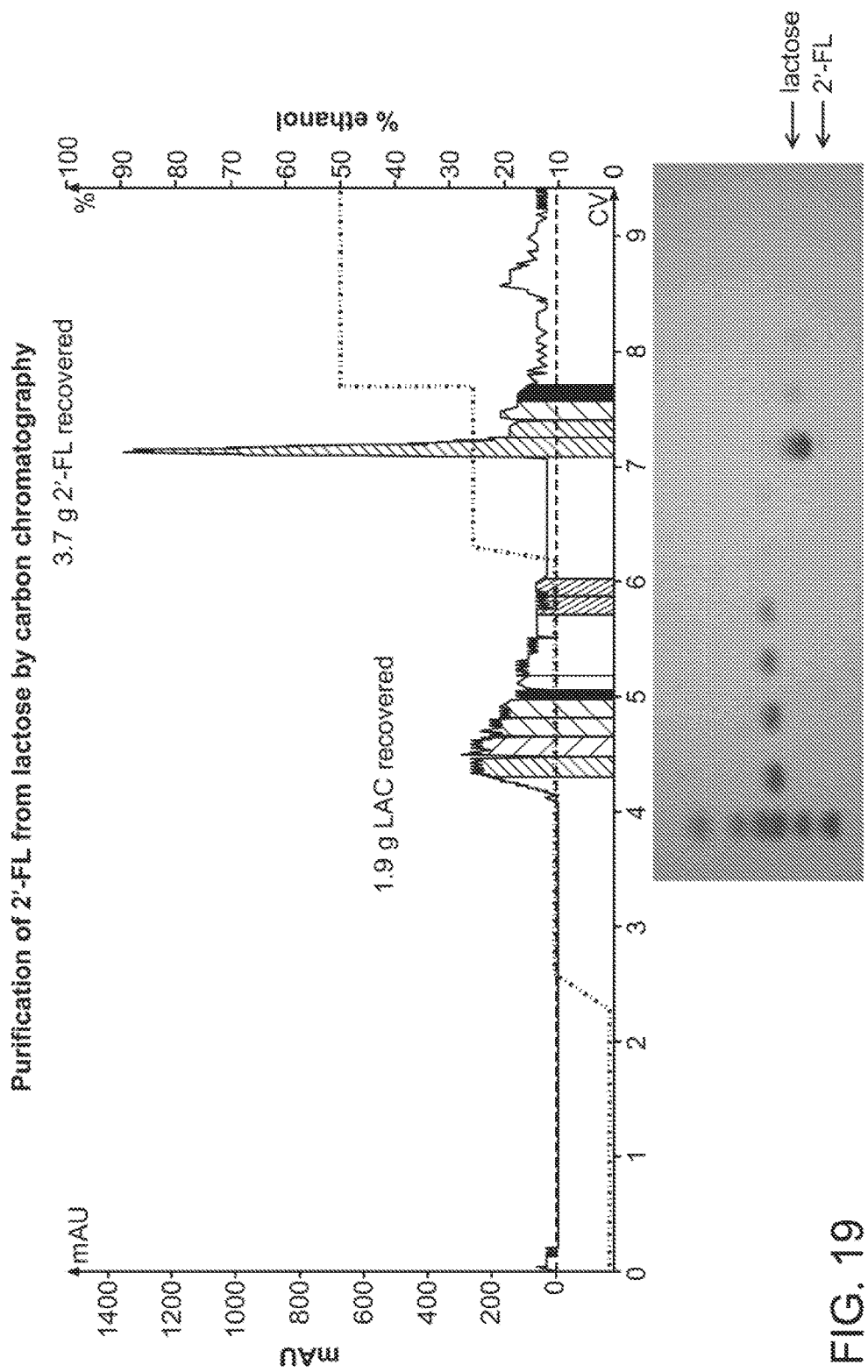

FIG. 19 is a column chromatogram and a TLC analysis of the resolution on a carbon column of a sample of 2'-FL made in *E. coli* from a lactose impurity.

Figure 20:
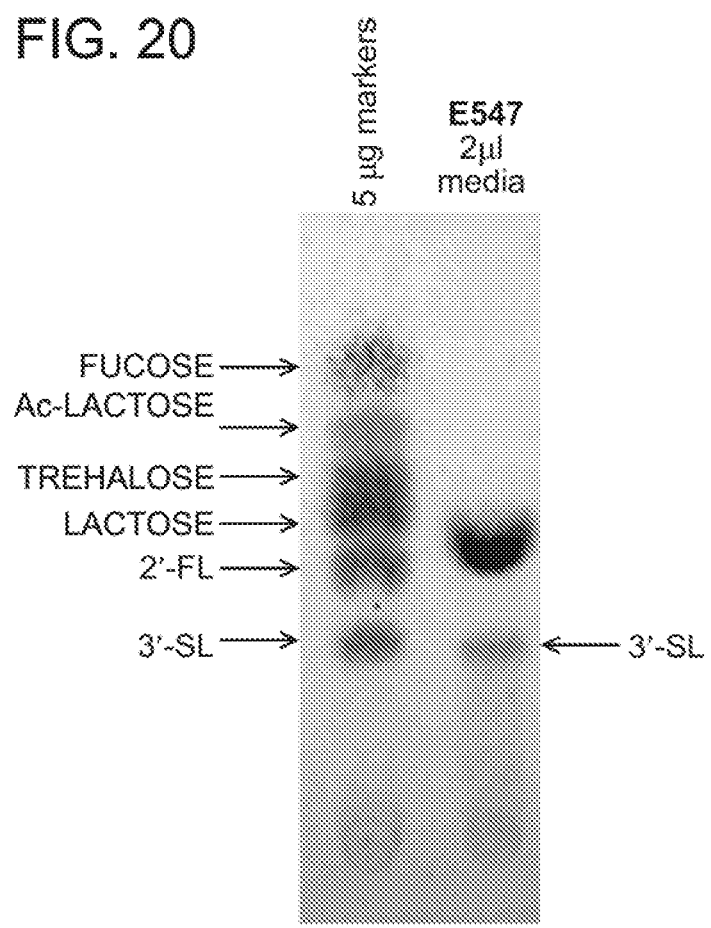

FIG. 20 is a photograph of a thin layer chromatogram showing 3'-SL in culture medium produced by *E. coli* strain E547, containing plasmids expressing a bacterial α(2,3) sialyltransferase and neuA, neuB and neuC.

DETAILED DESCRIPTION OF THE INVENTION

Figure 1:
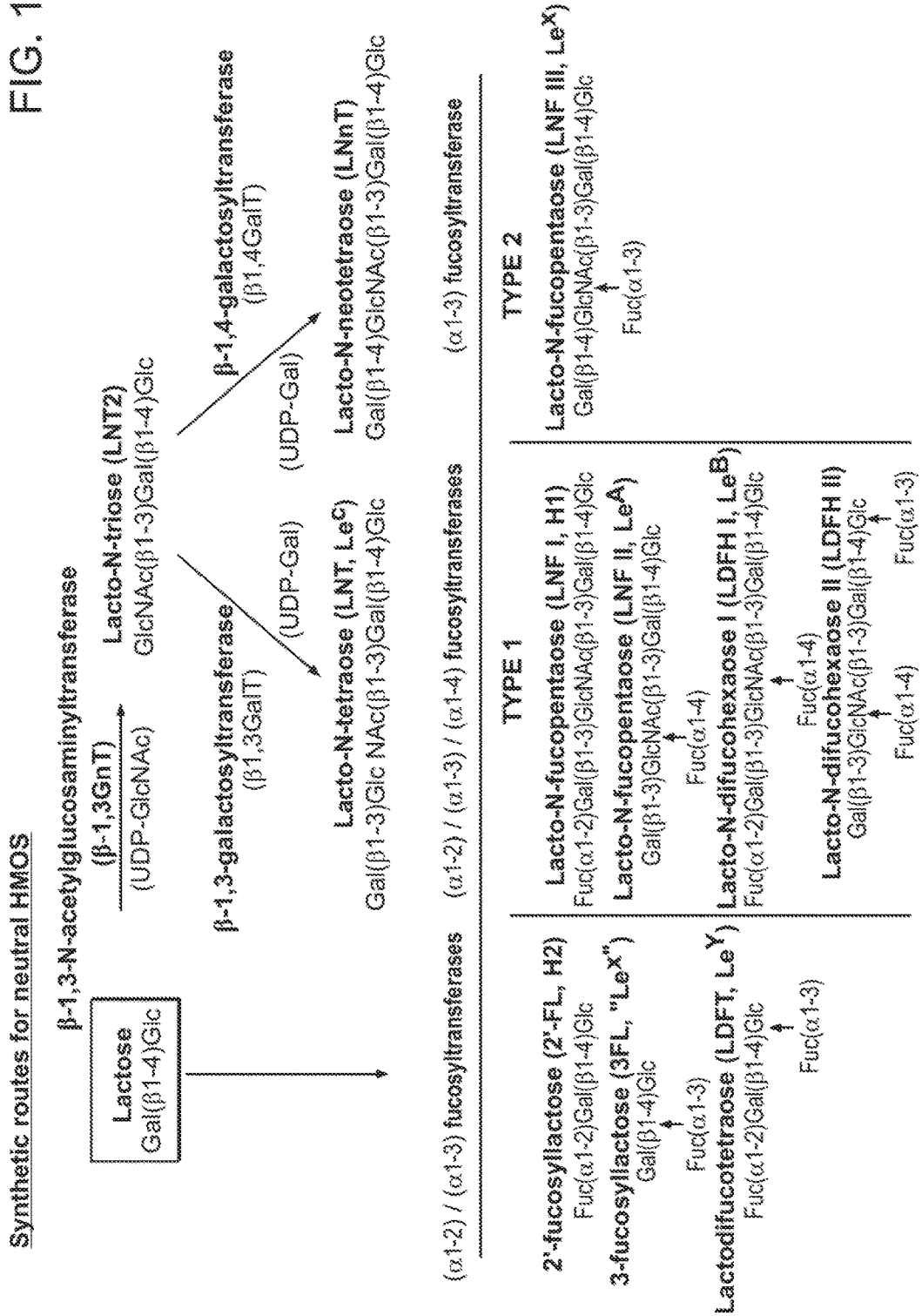
FIG. 1 is a schematic illustration showing the synthetic pathway of the major neutral fucosyl-oligosaccharides found in human milk.
Figure 2:
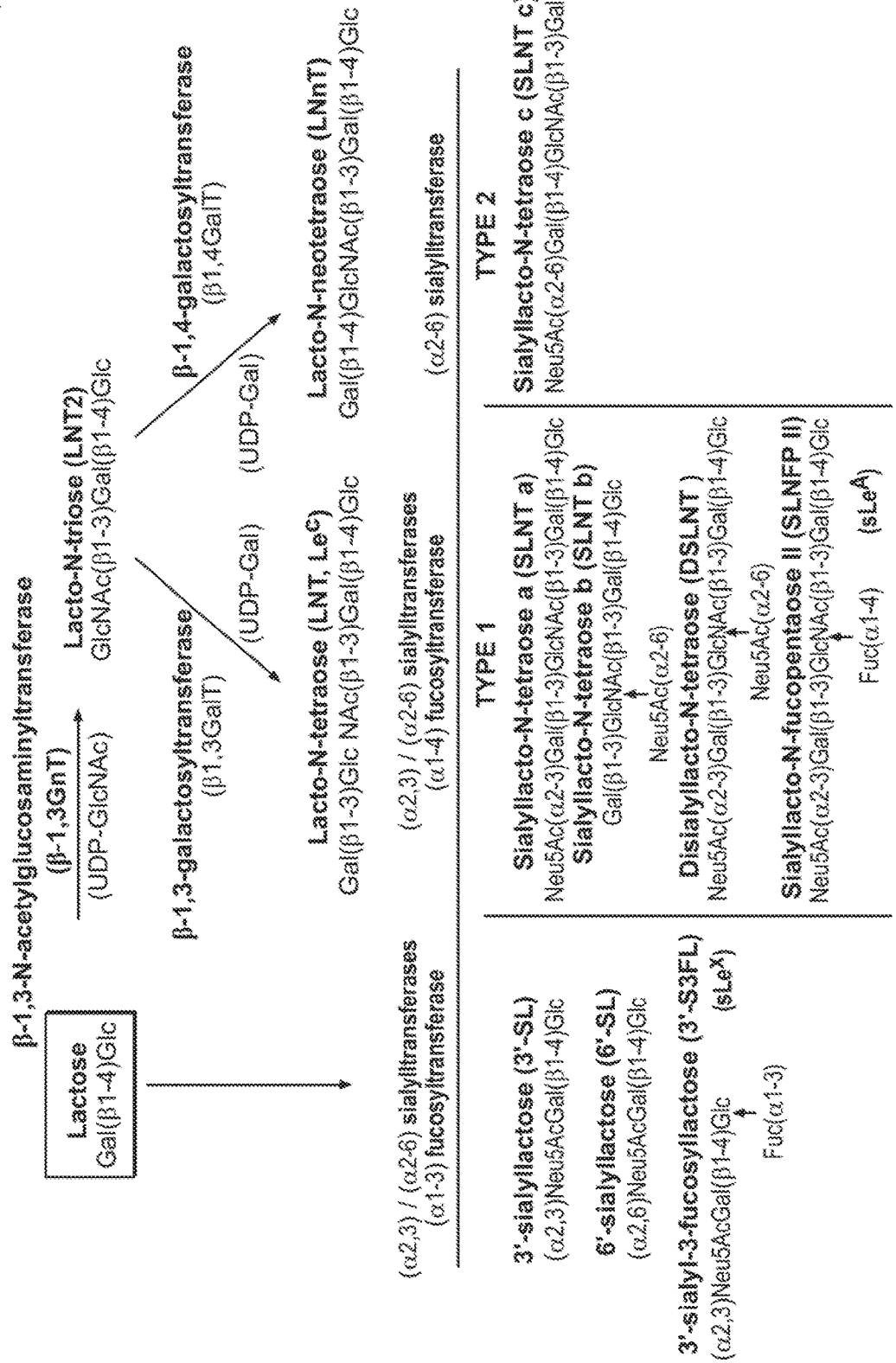
FIG. 2 is a schematic illustration showing the synthetic pathway of the major sialyl-oligosaccharides found in human milk.

Human milk glycans, which comprise both oligosaccharides (HMOS) and their glycoconjugates, play significant roles in the protection and development of human infants, and in particular the infant gastrointestinal (GI) tract. Milk oligosaccharides found in various mammals differ greatly, and their composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Previously, a full exploration of the roles of HMOS was limited by the inability to adequately characterize and measure these compounds. In recent years sensitive and reproducible quantitative methods for the analysis of both neutral and acidic HMOS have been developed (Erney, R., Hilty, M., Pickering, L., Ruiz-Palacios, G., and Prieto, P. (2001) *Adv Exp Med Biol* 501, 285-297. Bao, Y., and Newburg, D. S. (2008) *Electrophoresis* 29, 2508-2515). Approximately 200 distinct oligosaccharides have been identified in human milk, and combinations of a small number of simple epitopes are responsible for this diversity (Newburg D. S., 1999 Curr_Med Chem, 6:117-127; Ninonuevo M. et al., 2006 J Agric Food Chem, 54:7471-74801). HMOS are composed of 5 monosaccharides: D-glucose (Glc), D-galactose (Gal), N-acetylglucosamine (GlcNAc), L-fucose (Fuc), and sialic acid (N-acetyl neuraminic acid, NeuSAc, NANA). HMOS are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal_Biochem, 273:261-277; Martín-Sosa et al., 2003 J Dairy Sci, 86:52-59; Parkkinen J. and Finne J., 1987 Methods Enzymol, 138:289-300; Shen Z. et al., 2001 J Chromatogr A, 921:315-321). Approximately 70-80% of oligosaccharides in human milk are fucosylated, and their synthetic pathways are believed to proceed in a manner similar to those pathways shown in FIG. 1 (with the Type I and Type II subgroups beginning with different precursor molecules). A smaller proportion of the oligosaccharides in human milk are sialylated, or are both fucosylated and sialylated. FIG. 2 outlines possible biosynthetic routes for sialylated (acidic) HMOS, although their actual synthetic pathways in humans are not yet completely defined.

Interestingly, HMOS as a class, survive transit through the intestine of infants very efficiently, a function of their being poorly transported across the gut wall and of their resistance to digestion by human gut enzymes (Chaturvedi, P., Warren, C. D., Buescher, C. R., Pickering, L. K. & Newburg, D. S. Adv Exp Med Biol 501, 315-323 (2001)). One consequence of this survival in the gut is that HMOS are able to function as prebiotics, i.e. they are available to serve as an abundant carbon source for the growth of resident gut commensal microorganisms (Ward, R. E., Nirionuevo, M., Mills, D. A., Lebrilla, C. B., and German, J. B. (2007) *Mol Nutr Food Res* 51, 1398-1405). Recently, there is burgeoning interest in the role of diet and dietary prebiotic agents in determining the composition of the gut microflora, and in understanding the linkage between the gut microflora and human health (Roberfroid, M., Gibson, G. R., Hoyles, L., McCartney, A. L., Rastall, R., Rowland, I., Wolvers, D., Watzl, B., Szajewska, H., Stahl, B., Guarner, F., Respondek, F., Whelan, K., Coxam, V., Davicco, M. J., Léotoing, L., Wittrant, Y., Delzenne, N. M., Cani, P. D., Neyrinck, A. M., and Meheust, A. (2010) Br J Nutr 104 Suppl 2, S1-63).

A number of human milk glycans possess structural homology to cell receptors for enteropathogens, and serve roles in pathogen defense by acting as molecular receptor "decoys". For example, pathogenic strains of *Campylobacter* bind specifically to glycans in human milk containing the H-2 epitope, i.e., 2'-fucosyl-N-acetyllactosamine or 2'-fucosyllactose (2'-FL); *Campylobacter* binding and infectivity are inhibited by 2'-FL and other glycans containing this H-2 epitope (Ruiz-Palacios, G. M., Cervantes, L. E., Ramos, P., Chavez-Munguia, B., and Newburg, D. S. (2003) *J Biol Chem* 278, 14112-14120). Similarly, some diarrheagenic *E. coli* pathogens are strongly inhibited in vivo by HMOS containing 2'-linked fucose moieties. Several major strains of human caliciviruses, especially the noroviruses, also bind to 2'-linked fucosylated glycans, and this binding is inhibited by human milk 2'-linked fucosylated glycans. Consumption of human milk that has high levels of these 2'-linked fucosyloligosaccharides has been associated with lower risk of norovirus, *Campylobacter*, ST of *E. coli*-associated diarrhea, and moderate-to-severe diarrhea of all causes in a Mexican cohort of breastfeeding children (Newburg D. S. et al., 2004 Glycobiology, 14:253-263; Newburg D. S. et al., 1998 Lancet, 351:1160-1164). Several pathogens are also known to utilize sialylated glycans as their host receptors, such as influenza (Couceiro, J. N., Paulson, J. C. & Baum, L. G. Virus Res 29, 155-165 (1993)), parainfluenza (Amonsen, M., Smith, D. F., Cummings, R. D. & Air, G. M. J Virol 81, 8341-8345 (2007), and rotoviruses (Kuhlenschmidt, T. B., Hanafin, W. P., Gelberg, H. B. & Kuhlenschmidt, M. S. Adv Exp Med Biol 473, 309-317 (1999)). The sialyl-Lewis X epitope is used by *Helicobacter pylori* (Mahdavi, J., Sondén, B., Hurtig, M., Olfat, F. O., et al. Science 297, 573-578 (2002)), *Pseudomonas aeruginosa* (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoëen-Clouet, N., et al. Glycobiology 19, 309-320 (2009)).

While studies suggest that human milk glycans could be used as prebiotics and as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Novel chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)). Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)). However, low overall product yields and high process complexity have limited the commercial utility of these approaches.

Prior to the invention described herein, which enables the inexpensive production of large quantities of neutral and acidic HMOS, it had not been possible to fully investigate the ability of this class of molecule to inhibit pathogen binding, or indeed to explore their full range of potential additional functions.

Prior to the invention described herein, chemical syntheses of HMOS were possible, but were limited by stereospecificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). Also, prior to the invention described herein, in vitro enzymatic syntheses were also possible, but were limited by a requirement for expensive nucleotide-sugar precursors. The invention overcomes the shortcomings of these previous attempts by providing new strategies to inexpensively manufacture large quantities of human milk oligosaccharides for use as dietary supplements. The invention described herein makes use of an engineered bacterium *E. coli* (or other bacteria) engineered to produce 2'-FL, 3FL, LDFT, or sialylated fucosyl-oligosaccharides in commercially viable levels, for example the methods described herein enable the production of 2'-fucosylactose at >50 g/L in bioreactors.

Example 1. Engineering of *E. coli* to Generate Host Strains for the Production of Fucosylated Human Milk Oligosaccharides The *E. coli* K12 prototroph W3110 was chosen as the parent background for fucosylated HMOS biosynthesis. This strain had previously been modified at the ampC locus by the introduction of a tryptophan-inducible $P_{trpB}$-cI+ repressor construct (McCoy, J. & Lavallie, E. Current protocols in molecular biology/edited by Frederick M. Ausubel ... [et al.] (2001)), enabling economical production of recombinant proteins from the phage $\lambda P_L$ promoter (Sanger, F., Coulson, A. R., Hong, G. F., Hill, D. F. & Petersen, G. B. J Mol Biol 162, 729-773 (1982)) through induction with millimolar concentrations of tryptophan (Mieschendahl, M., Petri, T. & Hänggi, U. Nature Biotechnology 4, 802-808 (1986)). The strain GI724, an *E. coli* W3110 derivative containing the tryptophan-inducible $P_{trpB}$-cI+ repressor construct in ampC, was used at the basis for further *E. coli* strain manipulations (FIG. 14).

Figure 3:
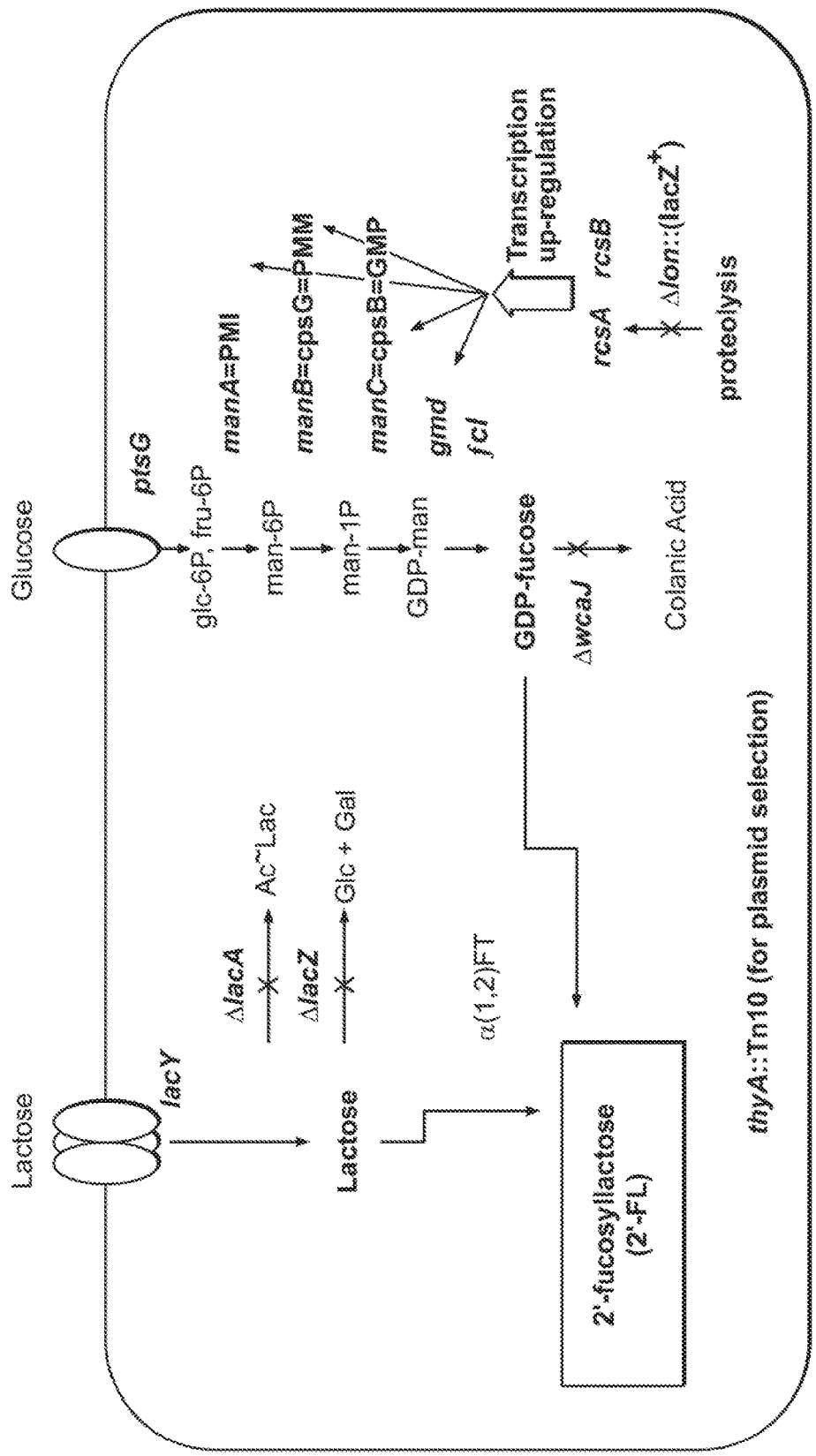
FIG. 3 is a schematic demonstrating metabolic pathways and the changes introduced into them to engineer 2'-fucosyllactose (2'-FL) synthesis in *Escherichia coli* (*E. coli*). Specifically, the lactose synthesis pathway and the GDP-fucose synthesis pathway are illustrated. In the GDP-fucose synthesis pathway: manA=phosphomannose isomerase (PMI), manB=phosphomannomutase (PMM), manC=mannose-1-phosphate guanylyltransferase (GMP), gmd=GDP-mannose-4,6-dehydratase,fcl=GDP-fucose synthase (GFS), and ΔwcaJ=mutated UDP-glucose lipid carrier transferase.
Figure 4:
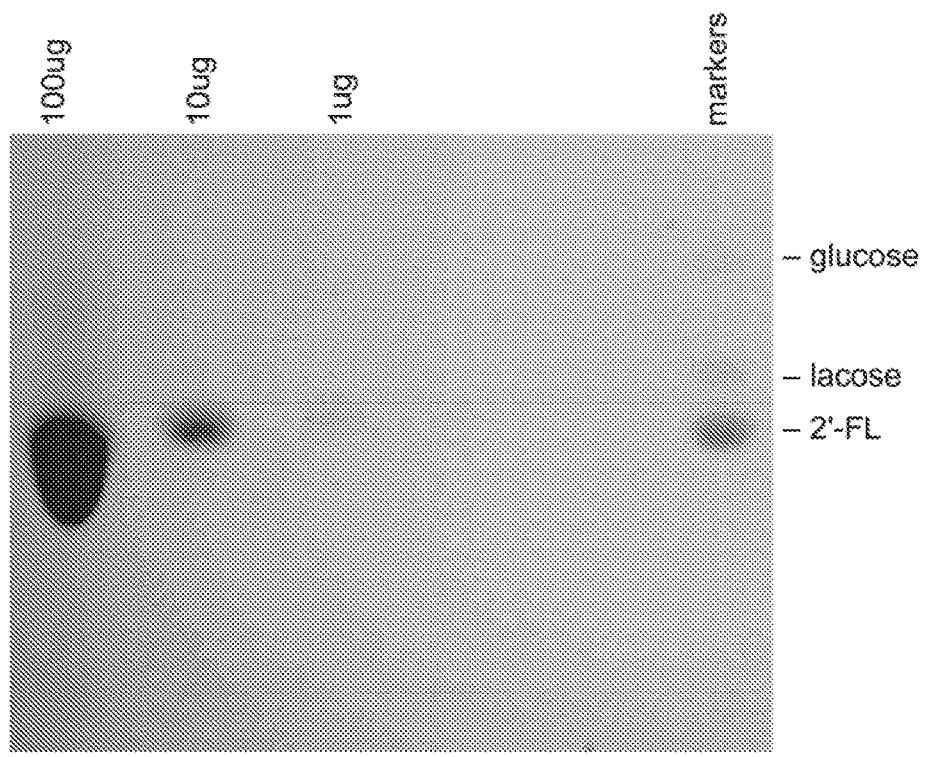
FIG. 4 is a photograph of a thin layer chromatogram of purified 2'-FL produced in *E. coli*.

Biosynthesis of fucosylated HMOS requires the generation of an enhanced cellular pool of both lactose and GDP-fucose (FIG. 3). This enhancement was achieved in strain GI724 through several manipulations of the chromosome using λ Red recombineering (Court, D. L., Sawitzke, J. A. & Thomason, L. C. Annu Rev Genet 36, 361-388 (2002)) and generalized P1 phage transduction (Thomason, L. C., Costantino, N. & Court, D. L. Mol Biol Chapter 1, Unit 1.17 (2007)). FIG. 14 is a table presenting the genotypes of several *E. coli* strains constructed for this invention. The ability of the *E. coli* host strain to accumulate intracellular lactose was first engineered in strain E183 (FIG. 14) by simultaneous deletion of the endogenous β-galactosidase gene (lacZ) and the lactose operon repressor gene (lacI). During construction of this deletion in GI724 to produce E183, the lacIq promoter was placed immediately upstream of the lactose permease gene, lacY. The modified strain thus maintains its ability to transport lactose from the culture medium (via LacY), but is deleted for the wild-type copy of the lacZ (β-galactosidase) gene responsible for lactose catabolism. An intracellular lactose pool is therefore created when the modified strain is cultured in the presence of exogenous lactose.

Subsequently, the ability of the host *E. coli* strain to synthesize colanic acid, an extracellular capsular polysaccharide, was eliminated in strain E205 (FIG. 14) by the deletion of the wcaJ gene, encoding the UDP-glucose lipid carrier transferase (Stevenson, G., Andrianopoulos, K., Hobbs, M. & Reeves, P. R. J Bacteriol 178, 4885-4893 (1996)) in strain E183. In a wcaJ null background, GDP-fucose accumulates in the *E. coli* cytoplasm (Dumon, C., Priem, B., Martin, S. L., Heyraud, A., et al. Glycoconj J 18, 465-474 (2001)).

A thyA (thymidylate synthase) mutation was introduced into strain E205 to produce strain E214 (FIG. 14) by P1 transduction. In the absence of exogenous thymidine, thyA strains are unable to make DNA, and die. The defect can be complemented in trans by supplying a wild-type thyA gene on a multicopy plasmid (Belfort, M., Maley, G. F. & Maley, F. Proceedings of the National Academy of Sciences 80, 1858 (1983)). This complementation is used herein as a means of plasmid maintenance (eliminating the need for a more conventional antibiotic selection scheme to maintain plasmid copy number).

One strategy for GDP-fucose production is to enhance the bacterial cell's natural synthesis capacity. For example, this is enhancement is accomplished by inactivating enzymes involved in GDP-fucose consumption, and/or by overexpressing a positive regulator protein, RcsA, in the colanic acid (a fucose-containing exopolysaccharide) synthesis pathway. Collectively, this metabolic engineering strategy re-directs the flux of GDP-fucose destined for colanic acid synthesis to oligosaccharide synthesis (FIG. 3). By "GDP-fucose synthesis pathway" is meant a sequence of reactions, usually controlled and catalyzed by enzymes, which results in the synthesis of GDP-fucose. An exemplary GDP-fucose synthesis pathway in *Escherichia coli* as described in FIG. 3 is set forth below. In the GDP-fucose synthesis pathway set forth below, the enzymes for GDP-fucose synthesis include: 1) manA=phosphomannose isomerase (PMI), 2) manB=phosphomannomutase (PMM), 3) manC=mannose-1-phosphate guanylyltransferase (GMP), 4) gmd=GDP-mannose-4,6-dehydratase (GMD), 5)fcl=GDP-fucose synthase (GFS), and 6) Δwcaf=mutated UDP-glucose lipid carrier transferase.

Glucose→Glc-6-P→Fru-6-P→¹Man-6-P→²Man-1-P→³GDP-Man→⁴,⁵GDP-Fuc 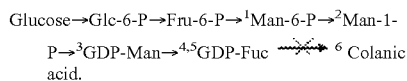 ⁶ Colanic acid.

Figure 7:
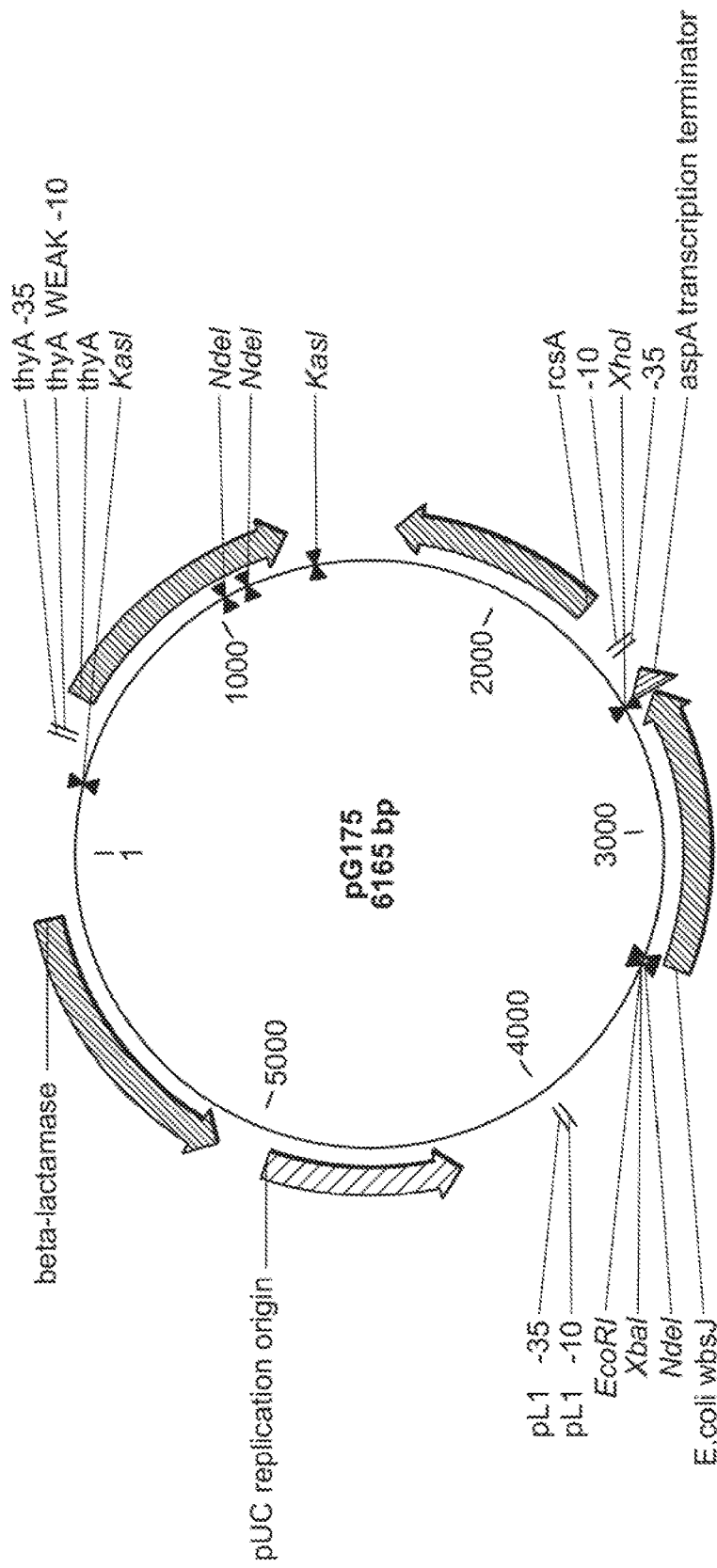
FIG. 7 is a plasmid map of pG175, which expresses the *E. coli* α(1,2)fucosyltransferase gene wbsJ.
Figure 10:
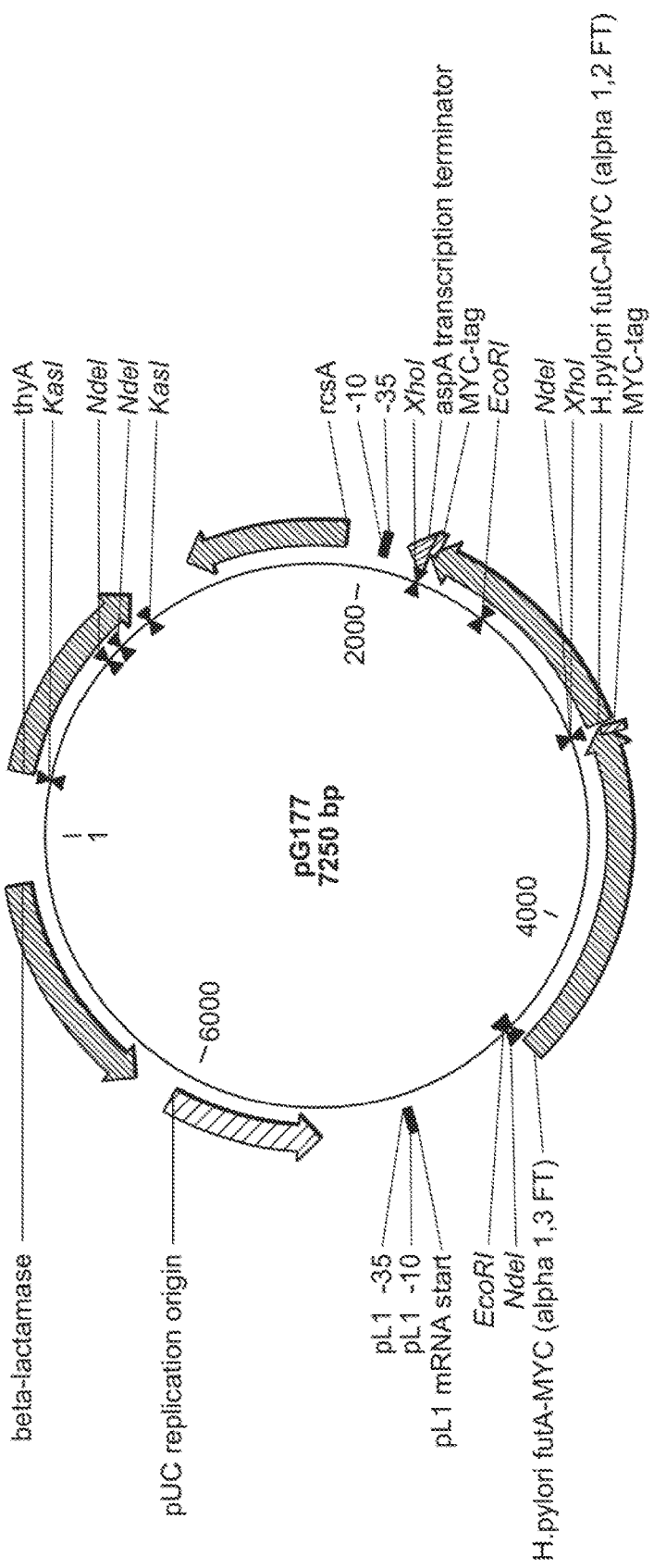
FIG. 10 is a plasmid map of pG177, which contains both the *H. pylori* 26695 α(1,2)fucosyltransferase gene futC and the *H. pylori* 26695 α(1,3)fucosyltransferase gene futA, configured as an operon.

Specifically, the magnitude of the cytoplasmic GDP-fucose pool in strain E214 is enhanced by over-expressing the *E. coli* positive transcriptional regulator of colanic acid biosynthesis, RscA (Gottesman, S. & Stout, V. Mol Microbiol 5, 1599-1606 (1991)). This over-expression of RcsA is achieved by incorporating a wild-type rcsA gene, including its promoter region, onto a multicopy plasmid vector and transforming the vector into the *E. coli* host, e.g. into E214. This vector typically also carries additional genes, in particular one or two fucosyltransferase genes under the control of the pL promoter, and thyA and beta-lactamase genes for plasmid selection and maintenance. pG175 (SEQ ID NO: 1 and FIG. 7), pG176 (SEQ ID NO: 2), pG177 (SEQ ID NO: 3 and FIG. 10), pG171 (SEQ ID NO: 5) and pG180 (SEQ ID NO: 6) are all examples of fucosyltransferase-expressing vectors that each also carry a copy of the rcsA gene, for the purpose of increasing the intracellular GDP-fucose pool of the *E. coli* hosts transformed with these plasmids. Over-expression of an additional positive regulator of colanic acid biosynthesis, namely RcsB (Gupte G, Woodward C, Stout V. Isolation and characterization of rcsb mutations that affect colanic acid capsule synthesis in *Escherichia coli* K-12. J Bacteriol 1997, July; 179(13):4328-35.), can also be utilized, either instead of or in addition to over-expression of RcsA, to increase intracellular GDP-fucose levels. Over-expression of rcsB is also achieved by including the gene on a multi-copy expression vector. pG186 is such a vector (SEQ ID NO: 8 and FIG. 15). pG186 expresses rcsB in an operon with futC under pL promoter control. The plasmid also expresses rcsA, driven off its own promoter. pG186 is a derivative of pG175 in which the α(1,2) FT (wbsJ) sequence is replaced by the *H. pylori* futC gene (FutC is MYC-tagged at its C-terminus). In addition, at the XhoI restriction site immediately 3' of the futC CDS, the *E. coli* rcsB gene is inserted, complete with a ribosome binding site at the 5' end of the rcsB CDS, and such that futC and rcsB form an operon.

A third means to increase the intracellular GDP-fucose pool may also be employed. Colanic acid biosynthesis is increased following the introduction of a null mutation into the *E. coli* lon gene. Lon is an ATP-dependant intracellular protease that is responsible for degrading RcsA, mentioned above as a positive transcriptional regulator of colanic acid biosynthesis in *E. coli* (Gottesman, S. & Stout, V. Mol Microbiol 5, 1599-1606 (1991)). In a lon null background, RcsA is stabilized, RcsA levels increase, the genes responsible for GDP-fucose synthesis in *E. coli* are up-regulated, and intracellular GDP-fucose concentrations are enhanced. The lon gene was almost entirely deleted and replaced by an inserted functional, wild-type, but promoter-less *E. coli* lacZ⁺ gene (Δlon::(kan, lacZ⁺) in strain E214 to produce strain E390. λRed recombineering was used to perform the construction. FIG. 12 illustrates the new configuration of genes engineered at the lon locus in E390. FIG. 13A-E presents the complete DNA sequence of the region, with annotations in GenBank format. Genomic DNA sequence surrounding the lacZ+ insertion into the lon region in *E. coli* strain E390 is set forth below (SEQ ID NO: 7)

The lon mutation in E390 increases intracellular levels of RcsA, and enhances the intracellular GDP-fucose pool. The inserted lacZ⁺ cassette not only knocks out lon, but also converts the lacZ⁻ host back to both a lacZ⁺ genotype and phenotype. The modified strain produces a minimal (albeit still readily detectable) level of β-galactosidase activity (1-2 units), which has very little impact on lactose consumption during production runs, but which is useful in removing residual lactose at the end of runs, is an easily scorable phenotypic marker for moving the lon mutation into other lacZ⁻ *E. coli* strains by P1 transduction, and can be used as a convenient test for cell lysis (e.g. caused by unwanted bacteriophage contamination) during production runs in the bioreactor.

The production host strain, E390 incorporates all the above genetic modifications and has the following genotype:

ampC::(P$_{trpB}$λcI⁺), P$_{lacI}$$^q$(ΔlacI-lacZ)$_{158}$lacY⁺, ΔwcaJ, thyA$_{748}$::Tn10, Δlon::(kan, lacZ⁺)

An additional modification of E390 that is useful for increasing the cytoplasmic pool of free lactose (and hence the final yield of 2'-FL) is the incorporation of a lacA mutation. LacA is a lactose acetyltransferase that is only active when high levels of lactose accumulate in the *E. coli* cytoplasm. High intracellular osmolarity (e.g., caused by a high intracellular lactose pool) can inhibit bacterial growth, and *E. coli* has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in *E. coli* engineered to produce 2'-FL or other human milk oligosaccharides is therefore undesirable: it reduces overall yield. Moreover, acetyl-lactose is a side product that complicates oligosaccharide purification schemes. The incorporation of a lacA mutation resolves these problems. Strain E403 (FIG. 14) is a derivative of E390 that carries a deletion of the lacA gene and thus is incapable of synthesizing acetyl-lactose.

The production host strain, E403 incorporates all the above genetic modifications and has the following genotype:

ampC::(P$_{trpB}$λcI⁺), P$_{lacI}$$^q$(ΔlacI-lacZ)$_{158}$lacY⁺, ΔwcaJ, thyA$_{748}$::Tn10, Δlon::(kan, lacZ⁺) ΔlacA Example 2. 2'-FL Production at Small Scale Various alternative α(1,2) fucosyltransferases are able to utilize lactose as a sugar acceptor and are available for the purpose of 2'-FL synthesis when expressed under appropriate culture conditions in *E. coli* E214, E390 or E403. For example the plasmid pG175 (ColE1, thyA+, bla+, P$_{L2}$-wbsJ, rcsA+) (SEQ ID NO: 1, FIG. 7) carries the wbsf α(1,2) fucosyltransferase gene of *E. coli* strain O128:B12 and can direct the production of 2'-FL in *E. coli* strain E403. In another example plasmid pG171 (ColE1, thyA+, bla+, P$_{L2}$-futC, rcsA+) (SEQ ID NO: 5), carries the *H. pylori* 26695 futC α(1,2)fucosyltransferase gene (Wang, G., Rasko, D. A., Sherburne, R. & Taylor, D. E. Mol Microbiol 31, 1265-1274 (1999)) and will also direct the production of 2'-FL in strain E403. In a preferred example, the plasmid pG180(ColE1, thyA+, bla+, P$_{L2}$-wcfW, rcsA+) (SEQ ID NO: 6) carries the previously uncharacterized *Bacteriodes fragilis* NCTC 9343 wq141 α(1,2)fucosyltransferase gene of the current invention and directs the production of 2'-FL in *E. coli* strain E403.

Figure 8:
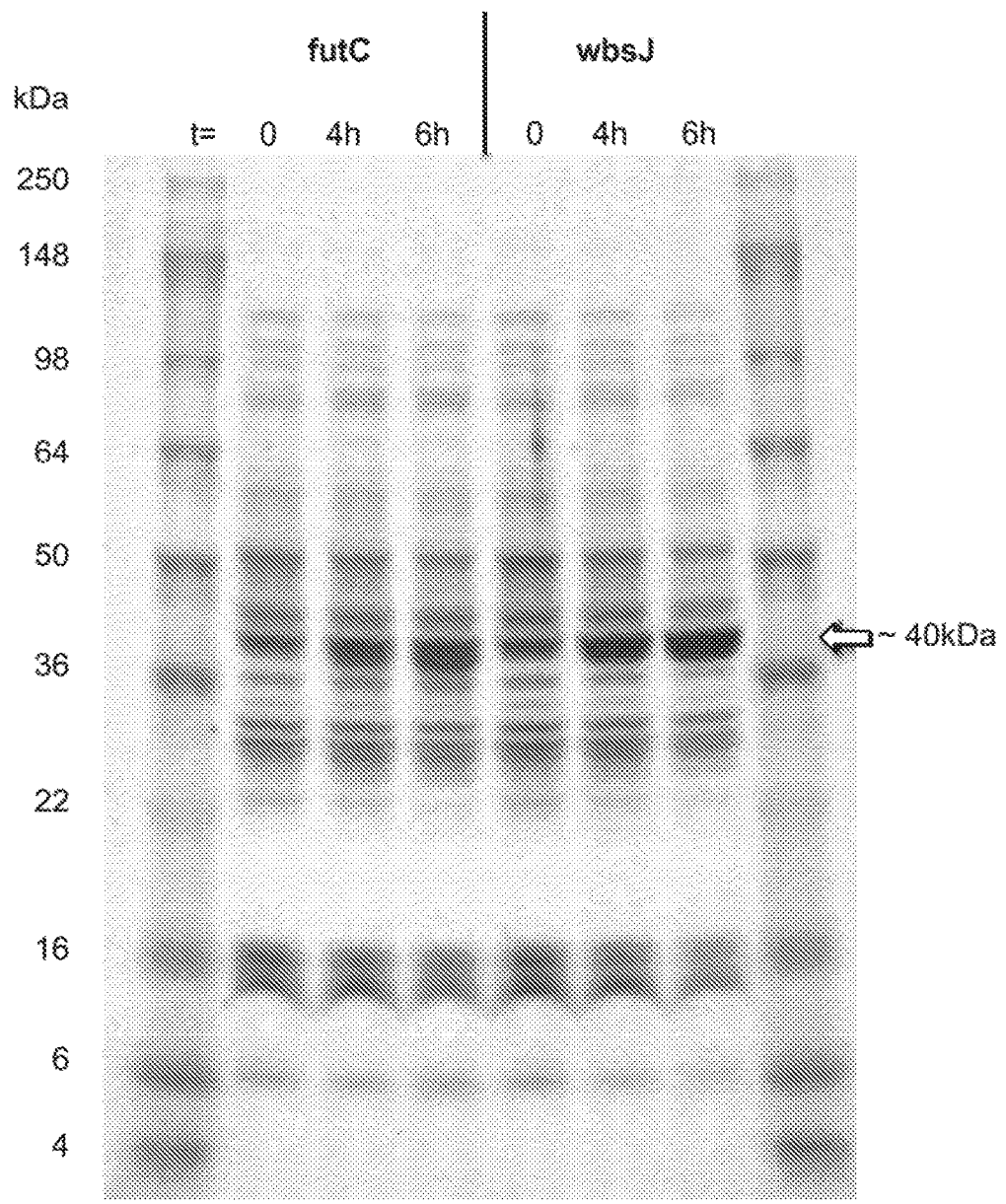
FIG. 8 is a photograph of a western blot of lysates of *E. coli* containing pG175 and expressing wbsJ, and of cells containing pG171, a pG175 derivative plasmid carrying the *H. pylori* 26695 futC gene in place of wbsJ and which expresses futC.
Figure 11:
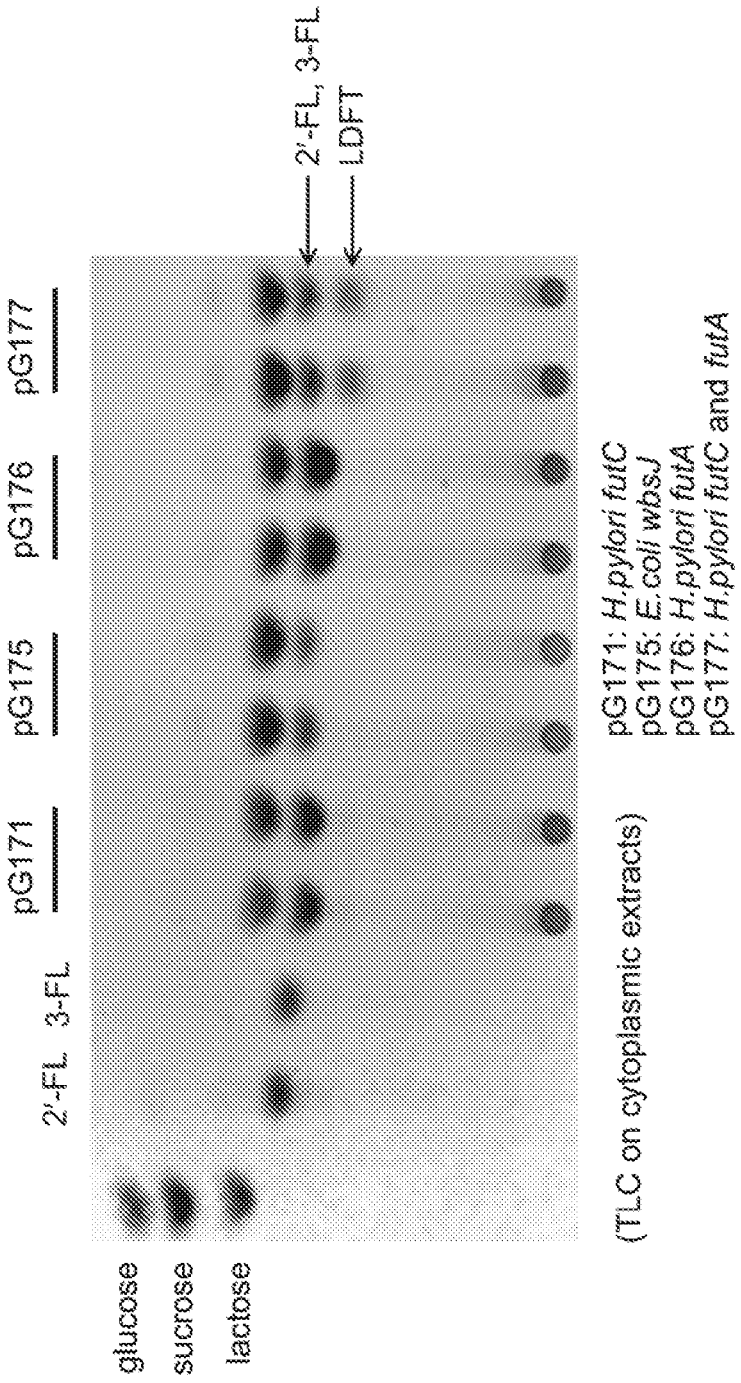
FIG. 11 is a photograph of a thin layer chromatogram of 2'-FL, 3FL, and LDFT (lactodifucotetraose) produced in *E.* coli, directed by plasmids pG171, pG175 (2'-FL), pG176 (3FL), and pG177 (LDFT, 2'-FL and 3FL).

The addition of tryptophan to the lactose-containing growth medium of cultures of any one of the strains E214. E390 or E403, when transformed with any one of the plasmids pG171, pG175 or pG180 leads, for each particular strain/plasmid combination, to activation of the host *E. coli* tryptophan utilization repressor TrpR, subsequent repression of pG$_{trpB}$, and a consequent decrease in cytoplasmic cI levels, which results in a de-repression of P$_L$, expression of futC, whsJ or wcjW, respectively, and production of 2'-FL. FIG. 8 is a coomassie blue-stained SDS PAGE gel of lysates of *E. coli* containing pG175 and expressing wbsJ, and of cells containing pG171 and expressing futC. Prominent stained protein bands running at a molecular weight of approximately 35 kDa are seen for both WbsJ and FutC at 4 and 6 h following P$_L$ induction (i.e., after addition of tryptophan). FIG. 16 is a coomassie blue-stained SDS PAGE gel of lysates of *E. coli* containing pG180 and expressing wcfW, and of cells containing pG171 and expressing *H. pylori* futC. Prominent stained bands for both WcfW and FutC are seen at a molecular weight of approximately 40 kDa at 4 and 6 h following P$_L$ induction (i.e., after addition of tryptophan to the growth medium). For 2'-FL production in small scale laboratory cultures (<100 ml) strains were grown at 30 C in a selective medium lacking both thymidine and tryptophan to early exponential phase (e.g. M9 salts, 0.5% glucose, 0.4% casaminoacids). Lactose was then added to a final concentration of 0.5 or 1%, along with tryptophan (200 µM final) to induce expression of the α(1,2) fucosyltransferase, driven from the PL promoter. At the end of the induction period (~24 h) TLC analysis was performed on aliquots of cell-free culture medium, or of heat extracts of cells (treatments at 98 C for 10 min, to release sugars contained within the cell). FIG. 11 shows a TLC analysis of cytoplasmic extracts of engineered *E. coli* cells transformed with pG175 or pG171. Cells were induced to express wbsJ or futC, respectively, and grown in the presence of lactose. The production of 2'-FL can clearly be seen in heat extracts of cells carrying either plasmid. FIG. 17 shows a TLC analysis of cytoplasmic extracts of engineered *E. coli* cells transformed with pG180 or pG171. Cells were induced to express wcfW or futC, respectively, and grown in the presence of lactose. The production of 2'-FL can clearly be seen with both plasmids. Prior to the present invention the wcfW gene had never been shown to encode a protein with demonstrated α(1,2) fucosyltransferase activity, or to utilize lactose as a sugar acceptor substrate.

The DNA sequence of the *Bacteroides fragilis* strain NCTC 9343 wcfW gene (protein coding sequence) is set forth below (SEQ ID NO: 4).

Example 3. 2'-FL Production in the Bioreactor

2'-FL can be produced in the bioreactor by any one of the host *E. coli* strains E214, E390 or E403, when transformed with any one of the plasmids pG171, pG175 or pG180. Growth of the transformed strain is performed in a minimal medium in a bioreactor, 10 L working volume, with control of dissolved oxygen, pH, lactose substrate, antifoam and nutrient levels. Minimal "FERM" medium is used in the bioreactor, which is detailed below.

Ferm (10 liters): Minimal medium comprising:
   40 g $(NH_4)_2HPO_4$
   100 g $KH_2PO_4$
   10 g $MgSO_4.7H_2O$
   40 g NaOH
   Trace elements:
   1.3 g NTA
   0.5 g $FeSO_4.7H_2O$
   0.09 g $MnCl_2.4H_2O$
   0.09 g $ZnSO_4.7H_2O$
   0.01 g $CoCl_2.6H_2O$
   0.01 g $CuCl_2.2H_2O$
   0.02 g $H_3BO_3$
   0.01 g $Na_2MoO_4.2H_2O$ (pH 6.8)
   Water to 10 liters
   DF204 antifoam (0.1 ml/L)
   150 g glycerol (initial batch growth), followed by fed batch mode with a 90% glycerol-1% $MgSO_4$-1× trace elements feed, at various rates for various times.

Production cell densities of $A_{600}$>100 are routinely achieved in these bioreactor runs. Briefly, a small bacterial culture is grown overnight in "FERM"—in the absence of either antibiotic or exogenous thymidine. The overnight culture (@~2 $A_{600}$) is used to inoculate a bioreactor (10 L working volume, containing "FERM") to an initial cell density of ~0.2 $A_{600}$. Biomass is built up in batch mode at 30° C. until the glycerol is exhausted ($A_{600}$~20), and then a fed batch phase is initiated utilizing glycerol as the limiting carbon source. At $A_{600}$~30, 0.2 g/L tryptophan is added to induce α(1,2) fucosyltransferase synthesis. An initial bolus of lactose is also added at this time. 5 hr later, a continuous slow feed of lactose is started in parallel to the glycerol feed. These conditions are continued for 48 hr (2'-FL production phase). At the end of this period, both the lactose and glycerol feeds are terminated, and the residual glycerol and lactose are consumed over a final fermentation period, prior to harvest. 2'-FL accumulates in the spent fermentation medium at concentrations as much as 30 times higher than in the cytoplasm. The specific yield in the spent medium varies between 10 and 50 g/L, depending on precise growth and induction conditions. FIG. 18 is a TLC of culture medium samples removed from a bioreactor at various times during a 2'-FL production run utilizing plasmid pG171 transformed into strain E403. All of the input lactose was converted to product by the end of the run, and product yield was approximately 25 g/L 2'-FL.

Example 4. 2'-Fucosyllactose Purification

2'-FL purification from *E. coli* fermentation broth is accomplished though five steps:
1. Clarification
   Fermentation broth is harvested and cells removed by sedimentation in a preparative centrifuge at 6000×g for 30 min. Each bioreactor run yields about 5-7 L of partially clarified supernatant. Clarified supernatants have a brown/orange coloration attributed to a fraction of caramelized sugars produced during the course of the fermentation, particularly by side-reactions promoted by the ammonium ions present in the fermentation medium.

2. Product Capture on Coarse Carbon

A column packed with coarse carbon (Calgon 12×40 TR) of ~1000 ml volume (dimension 5 cm diameter×60 cm length) is equilibrated with 1 column volume (CV) of water and loaded with clarified culture supernatant at a flow rate of 40 ml/min. This column has a total capacity of about 120 g of sugar (lactose). Following loading and sugar capture, the column is washed with 1.5 CV of water, then eluted with 2.5 CV of 50% ethanol or 25% isopropanol (lower concentrations of ethanol at this step (25-30%) may be sufficient for product elution). This solvent elution step releases about 95% of the total bound sugars on the column and a small portion of the color bodies (caramels). In this first step capture of the maximal amount of sugar is the primary objective. Resolution of contaminants is not an objective. The column can be regenerated with a 5 CV wash with water.

3. Evaporation

A volume of 2.5 L of ethanol or isopropanol eluate from the capture column is rotary-evaporated at 56 C and a sugar syrup in water is generated (this typically is a yellow-brown color). Alternative methods that could be used for this step include lyophilization or spray-drying.

4. Flash Chromatography on Fine Carbon and Ion Exchange Media

A column (GE Healthcare HiScale50/40, 5×40 cm, max pressure 20 bar) connected to a Biotage Isolera One FLASH Chromatography System is packed with 750 ml of a Darco Activated Carbon G60 (100-mesh): Celite 535 (coarse) 1:1 mixture (both column packings obtained from Sigma). The column is equilibrated with 5 CV of water and loaded with sugar from step 3 (10-50 g, depending on the ratio of 2'-FL to contaminating lactose), using either a celite loading cartridge or direct injection. The column is connected to an evaporative light scattering (ELSD) detector to detect peaks of eluting sugars during the chromatography. A four-step gradient of isopropanol, ethanol or methanol is run in order to separate 2'-FL from monosaccharides (if present), lactose and color bodies. e.g., for B=ethanol: Step 1, 2.5 CV 0% B; Step 2, 4 CV 10% B (elutes monosaccharides and lactose contaminants); step 3, 4 CV 25% B (Elutes 2'-FL); step 4, 5 CV 50% B (elutes some of the color bodies and partially regenerates the column) Additional column regeneration is achieved using methanol @50% and isopropanol @50%. Fractions corresponding to sugar peaks are collected automatically in 120-ml bottles, pooled and directed to step 5. In certain purification runs from longer-than-normal fermentations, passage of the 2'-FL-containing fraction through anion-exchange and cation exchange columns can remove excess protein/DNA/caramel body contaminants. Resins tested successfully for this purpose are Dowex 22 and Toyopearl Mono-Q, for the anion exchanger, and Dowex 88 for the cation exchanger. Mixed bed Dowex resins have proved unsuitable as they tend to adsorb sugars at high affinity via hydrophobic interactions. FIG. 19 illustrates the performance of Darco G60:celite 1:1 in separating lactose from 2'-fucoyllactose when used in Flash chromatography mode.

5. Evaporation/Lyophilization 3.0 L of 25% B solvent fractions is rotary-evaporated at 56 C until dry. Clumps of solid sugar are re-dissolved in a minimum amount of water, the solution frozen, and then lyophilized A white, crystalline, sweet powder (2'-FL) is obtained at the end of the process. 2'-FL purity obtained lies between 95 and 99%.

Sugars are routinely analyzed for purity by spotting 1 μl aliquots on aluminum-backed silica G60 Thin Layer Chromatography plates (10×20 cm; Macherey-Nagel). A mixture of LDFT (Rf=0.18), 2'-FL (Rf=0.24), lactose (Rf=0.30), trehalose (Rf=0.32), acetyl-lactose (Rf=0.39) and fucose (Rf=0.48) (5 g/L concentration for each sugar) is run alongside as standards. The plates are developed in a 50% butanol:25% acetic acid:25% water solvent until the front is within 1 cm from the top. Improved sugar resolution can be obtained by performing two sequential runs, drying the plate between runs. Sugar spots are visualized by spraying with α-naphtol in a sulfuric acid-ethanol solution (2.4 g α-naphtol in 83% (v/v) ethanol, 10.5% (v/v) sulfuric acid) and heating at 120 C for a few minutes. High molecular weight contaminants (DNA, protein, caramels) remain at the origin, or form smears with Rfs lower than LDFT.

Example 5. 3 FL Production

Figure 9:
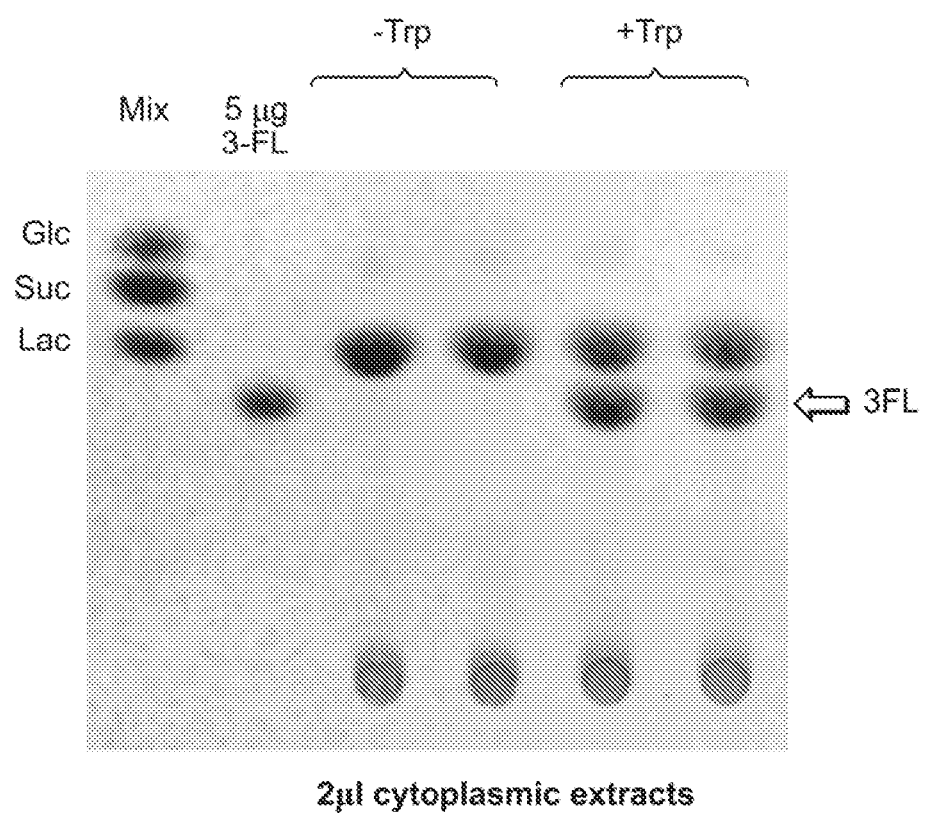
FIG. 9 is a photograph of a thin layer chromatogram of 3FL produced in *E. coli* containing the plasmid pG176 and induced for expression of the *H. pylori* 26695 α(1,3)fucosyltransferase gene futA by tryptophan addition.

Any one of *E. coli* host strains E214, E390 or E403, when transformed with a plasmid expressing an α(1,3)fucosyltransferase capable of using lactose as the sugar acceptor substrate, will produce the human milk oligosaccharide product, 3-fucosyllactose (3FL). FIG. 9 illustrates the pathways utilized in engineered strains of *E. coli* of this invention to achieve production of 3FL. For example, the plasmid pG176 (ColE1, thyA+, bla+, $P_{L2}$- futA, rcsA+) (SEQ ID NO: 2), is a derivative of pG175 in which the α(1,2) FT (wbsJ) sequence is replaced by the *Helicobacter pylori* futA gene (Dumon, C., Bosso, C., Utille, J. P., Heyraud, A. & Samain, E. Chembiochem 7, 359-365 (2006)). pG176 will direct the production of 3FL when transformed into any one of the host *E. coli* strains E214, E390 or E403. FIG. 11 shows a TLC analysis of 3FL production from E403 transformed with pG176. Additionally there are several other related bacterial-type α(1,3)-fucosyltransferases identified in *Helicobacter pylori* which could be used to direct synthesis of 3FL, e.g., "11639 FucTa" (Ge, Z., Chan, N. W., Palcic, M. M. & Taylor, D. E. J Biol Chem 272, 21357-21363 (1997); Martin, S. L., Edbrooke, M. R., Hodgman, T. C., van den Eijnden, D. H. & Bird, M. I. J Biol Chem 272, 21349-21356 (1997)) and "UA948 FucTa" (Rasko, D. A., Wang, G., Palcic, M. M. & Taylor, D. E. J Biol Chem 275, 4988-4994 (2000)). In addition to α(1,3)-fucosyltransferases from *H. pylori*, an α(1,3)fucosyltransferase (Hh0072, sequence accession AAP76669) isolated from *Helicobacter hepaticus* exhibits activity towards both non-sialylated and sialylated Type 2 oligosaccharide acceptor substrates (Zhang, L., Lau, K., Cheng, J., Yu, H., et al. Glycobiology (2010)). Furthermore, there are several additional bacterial α(1,3)-fucosyltransferases that may be used to make 3FL according to the methods of this invention. For example, close homologs of Hh0072 are found in H. *H. bilis* (HRAG_01092 gene, sequence accession EEO24035), and in *C. jejuni* (C1336_000250319 gene, sequence accession EFC31050).

3FL biosynthesis is performed as described above for 2'-FL, either at small scale in culture tubes and culture flasks, or in a bioreactor (10 L working volume) utilizing control of dissolved oxygen, pH, lactose substrate, antifoam and carbon:nitrogen balance. Cell densities of $A_{600}$~100 are reached in the bioreactor, and specific 3FL yields of up to 3 g/L have been achieved. Approximately half of the 3 FL produced is found in the culture supernatant, and half inside the cells. Purification of 3 FL from *E. coli* culture supernatants is achieved using an almost identical procedure to that described above for 2'-FL. The only substantive difference being that 3FL elutes from carbon columns at lower alcohol concentrations than does 2'-FL.

Example 6. The Simultaneous Production of Human Milk Oligosaccharides 2'-Fucosyllactose (2'-FL), 3-Fucosyllactose (3FL), and Lactodifucohexaose (LDFT) in *E. coli*

*E. coli* strains E214, E390 and E403 accumulate cytoplasmic pools of both lactose and GDP-fucose, as discussed above, and when transformed with plasmids expressing either an α(1,2) fucosyltransferase or an α(1,3) fucosyltransferase can synthesize the human milk oligosaccharides 2'-FL or 3FL respectively. The tetrasaccharide lactodifucotetrose (LDFT) is another major fucosylated oligosaccharide found in human milk, and contains both α(1,2)- and α(1,3)-linked fucose residues. pG177 (FIG. 10, SEQ ID NO: 3) is a derivative of pG175 in which the wbsJ gene is replaced by a two gene operon comprising the *Helicobacter pylori* futA gene and the *Helicobacter pylori* futC gene (i.e., an operon containing both an α(1,3)- and α(1,2)-fucosyltransferase). *E. coli* strains E214, E390 and E403 produce LDFT when transformed with plasmid pG177 and grown, either in small scale or in the bioreactor, as described above. In FIG. 11 (lanes pG177), LDFT made in *E. coli*, directed by pG177, was observed on analysis of cell extracts by thin layer chromatography.

Example 7. 3'-SL Synthesis in the *E. coli* Cytoplasm

The first step in the production of 3'-sialyllactose (3'-SL) in *E. coli* is generation of a host background strain that accumulates cytoplasmic pools of both lactose and CMP-Neu5Ac (CMP-sialic acid). Accumulation of cytoplasmic lactose is achieved through growth on lactose and inactivation of the endogenous *E. coli* β-galactosidase gene (lacZ), being careful to minimize polarity effects on lacY, the lac permease. This accumulation of a lactose pool has already been accomplished and is described above in *E. coli* hosts engineered for 2'-FL, 3FL and LDFT production.

Figure 5:
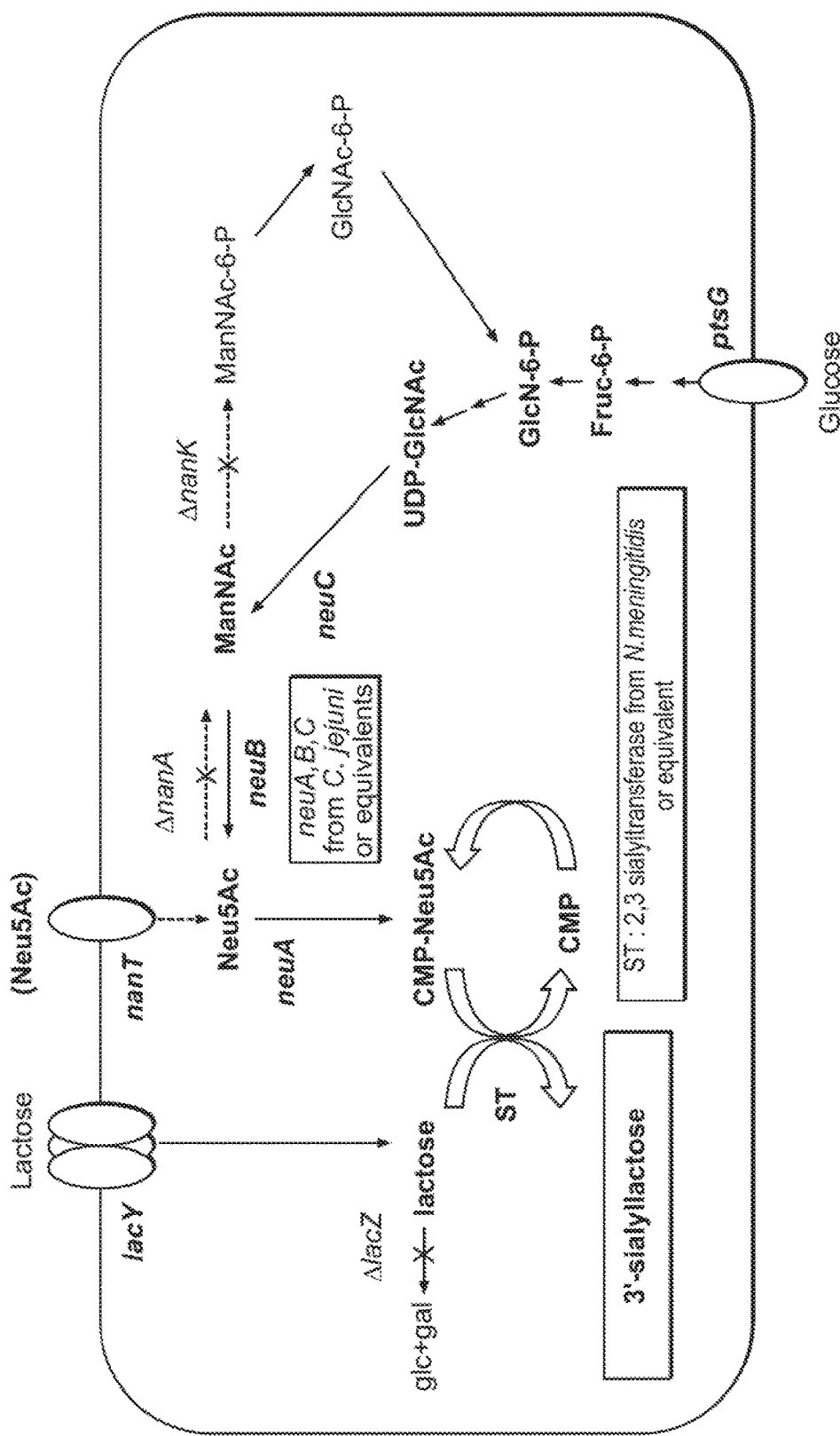
FIG. 5 is a schematic demonstrating metabolic pathways and the changes introduced into them to engineer 3'-sialyllactose (3'-SL) synthesis in *E. coli*. Abbreviations include: (Neu5Ac) N-acetylneuraminic acid, sialic acid; (nanT) sialic acid transporter; (ΔnanA) mutated N-acetylneuraminic acid lyase; (ManNAc) N-acetylmannosamine; (ΔnanK) mutated N-acetylmannosamine kinase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; and (neuB), N-acetylneuraminic acid synthase.
Figure 6:
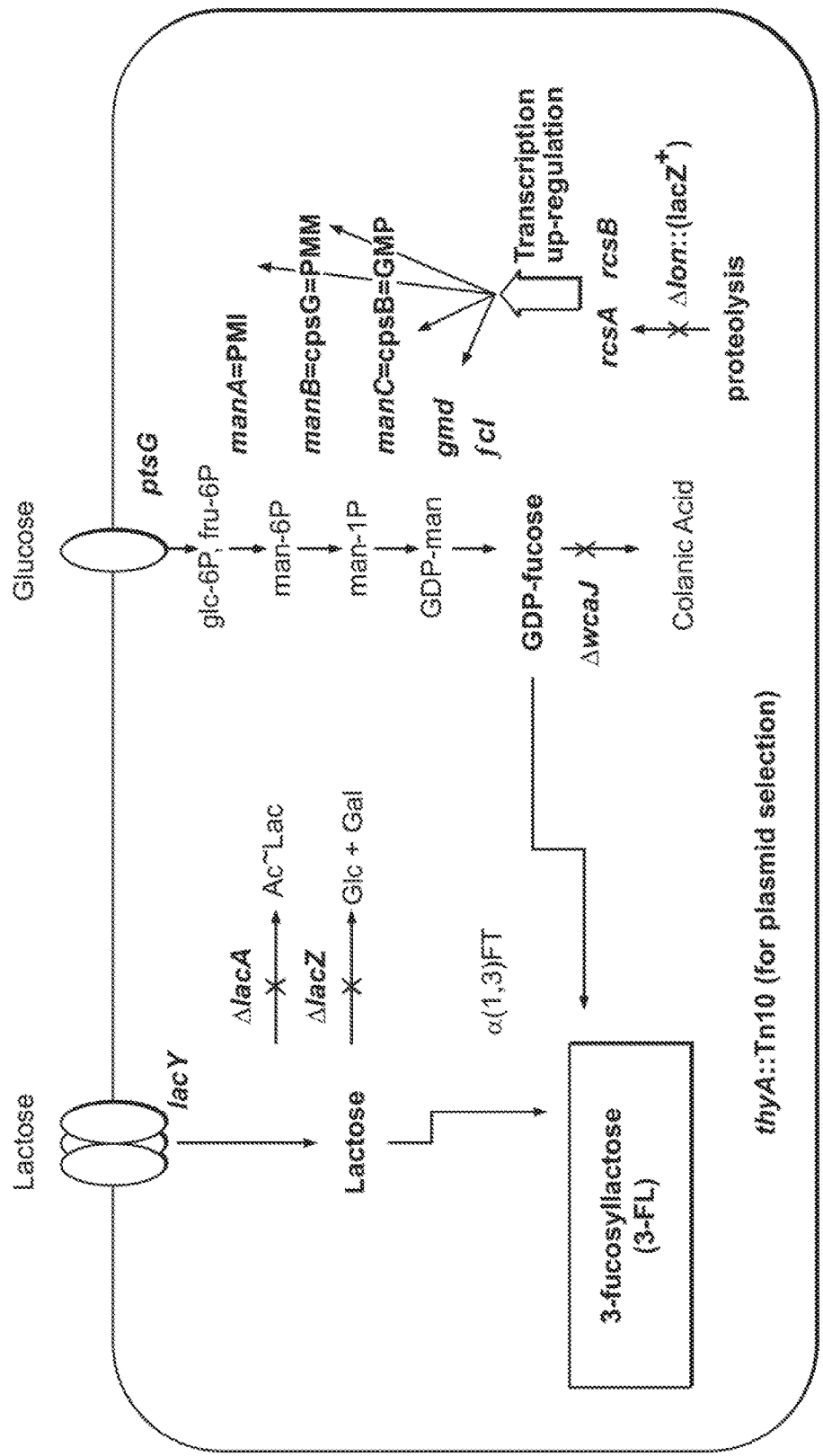
FIG. 6 is a schematic demonstrating metabolic pathways and the changes introduced into them to engineer 3-fucosyllactose (3-FL) synthesis in *E. coli*.

Specifically, a scheme to generate a cytoplasmic CMP-Neu5Ac pool, modified from methods known in the art, (e.g., Ringenberg, M., Lichtensteiger, C. & Vimr, E. Glycobiology 11, 533-539 (2001); Fierfort, N. & Samain, E. J Biotechnol 134, 261-265 (2008)), is shown in FIG. 5. Under this scheme, the *E. coli* K12 sialic acid catabolic pathway is first ablated through introduction of null mutations in endogenous nanA (N-acetylneuraminate lyase) and nanK (N-acetylmannosamine kinase) genes. By "sialic acid catabolic pathway" is meant a sequence of reactions, usually controlled and catalyzed by enzymes, which results in the degradation of sialic acid. An exemplary sialic acid catabolic pathway in *Escherichia coli* is set forth in FIG. 5. In the sialic acid catabolic pathway in FIG. 5, sialic acid (Neu5Ac; N-acetylneuraminic acid) is degraded by the enzymes NanA (N-acetylneuraminic acid lyase) and NanK (N-acetylmannosamine kinase). Other abbreviations for the sialic acid catabolic pathway in FIG. 5 include: (nanT) sialic acid transporter; (ΔnanA) mutated N-acetylneuraminic acid lyase; (ΔnanK) mutated N-acetylmannosamine kinase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; and (neuB), N-acetylneuraminic acid synthase.

Next, since *E. coli* K12 lacks a de novo sialic acid synthesis pathway, sialic acid synthetic capability is introduced through the provision of three recombinant enzymes; a UDP-GlcNAc 2-epimerase (e.g., neuC), a Neu5Ac synthase (e.g., neuB) and a CMP-Neu5Ac synthetase (e.g., neuA). Equivalent genes from *C. jejuni, E. coli* K1, *H. influenzae* or from *N. meningitides* can be utilized (interchangeably) for this purpose.

The addition of sialic acid to the 3' position of lactose to generate 3'-sialyllactose is then achieved utilizing a bacterial-type α(2,3)sialyltransferase, and numerous candidate genes have been described, including those from *N. meningitidis* and *N. gonorrhoeae* (Gilbert, M., Watson, D. C., Cunningham, A. M., Jennings, M. P., et al. J Biol Chem 271, 28271-28276 (1996); Gilbert, M., Cunningham, A. M., Watson, D. C., Martin, A., et al. Eur J Biochem 249, 187-194 (1997)). The *Neisseria* enzymes are already known to use lactose as an acceptor sugar. The recombinant *N. meningitidis* enzyme generates 3'-sialyllactose in engineered *E. coli* (Fierfort, N. & Samain, E. J Biotechnol 134, 261-265 (2008)). FIG. 20 shows a TLC analysis of culture media taken from a culture of *E. coli* strain E547 (ampC:: ($P_{trpB}$λcI$^+$),$P_{lacI}^q$(ΔlacI-lacZ)$_{158}$lacY$^+$, ΔlacA, Δnan) and carrying plasmids expressing neuA,B,C and a bacterial-type α(2,3)sialyltransferase. The presence of 3'-sialylactose (3'-SL) in the culture media is clearly seen.

Example 8. The Production of Human Milk Oligosaccharide 3'-Sialyl-3-Fucosyllactose (3'-S3FL) in *E. coli*

Prior to the invention described herein, it was unpredictable that a combination of any particular fucosyltransferase gene and any particular sialyl-transferase gene in the same bacterial strain could produce 3'-S3FL. Described below are results demonstrating that the combination of a fucosyltransferase gene and a sialyl-transferase gene in the same LacZ$^+$ *E. coli* strain resulted in the production of 3'-S3FL. These unexpected results are likely due to the surprisingly relaxed substrate specificity of the particular fucosyltransferase and sialyl-transferase enzymes utilized.

Humans synthesize the sialyl-Lewis X epitope utilizing different combinations of six α(1,3)fucosyl- and six α(2,3) sialyl-transferases encoded in the human genome (de Vries, T., Knegtel, R. M., Holmes, E. H. & Macher, B. A. Glycobiology 11, 119R-128R (2001); Taniguchi, A. Curr Drug Targets 9, 310-316 (2008)). These sugar transferases differ not only in their tissue expression patterns, but also in their acceptor specificities. For example, human myeloid-type α(1,3) fucosyltransferase (FUT IV) will fucosylate Type 2 (Galβ1→4Glc/GlcNAc) chain-based acceptors, but only if they are non-sialylated. In contrast "plasma-type" α(1,3) fucosyltansferase (FUT VI) will utilize Type 2 acceptors whether or not they are sialylated, and the promiscuous "Lewis" α(1,3/4) fucosyltransferase (FUT III), found in breast and kidney, will act on sialylated and non-sialylated Type 1 (Galβ1→3GlcNAc) and Type 2 acceptors (Easton, E. W., Schiphorst, W. E., van Drunen, E., van der Schoot, C. E. & van den Eijnden, D. H. Blood 81, 2978-2986 (1993)). A similar situation exists for the family of human☐ α(2,3) sialyl-transferases, with different enzymes exhibiting major differences in acceptor specificity (Legaigneur, P., Breton, C., El Battari, A., Guillemot, J. C., et al. J Biol Chem 276, 21608-21617 (2001); Jeanneau, C., Chazalet, V., Augé, C., Soumpasis, D. M., et al. J Biol Chem 279, 13461-13468 (2004)). This diversity in acceptor specificity highlights a key issue in the synthesis of 3'-sialyl-3-fucosyllactose (3'-S3FL) in *E. coli*, i.e., to identify a suitable combination of fucosyl- and sialyl-transferases capable of acting cooperatively to synthesize 3'-S3FL (utilizing lactose as the initial acceptor sugar). However, since human and all other eukaryotic fucosyl- and sialyl-transferases are secreted proteins located in the lumen of the golgi, they are poorly suited for the task of 3'-S3FL biosynthesis in the bacterial cytoplasm.

Several bacterial pathogens are known to incorporate fucosylated and/or sialylated sugars into their cell envelopes, typically for reasons of host mimicry and immune evasion. For example; both *Neisseria meningitides* and *Campylobacter jejuni* are able to incorporate sialic acid through 2,3-linkages to galactose moieties in their capsular lipooligosaccharide (LOS) (Tsai, C. M., Kao, G. & Zhu, P. I Infection and Immunity 70, 407 (2002); Gilbert, M., Brisson, J. R., Karwaski, M. F., Michniewicz, J., et al. J Biol Chem 275, 3896-3906 (2000)), and some strains of *E. coli* incorporate α(1,2) fucose groups into lipopolysaccharide (LPS) (Li, M., Liu, X. W., Shao, J., Shen, J., et al. Biochemistry 47, 378-387 (2008); Li, M., Shen, J., Liu, X., Shao, J., et al. Biochemistry 47, 11590-11597 (2008)). Certain strains of *Helicobacter pylori* are able not only to incorporate α(2,3)-sialyl-groups, but also α(1,2)-, α(1,3)-, and α(1,4)-fucosyl- groups into LPS, and thus can display a broad range of human Lewis-type epitopes on their cell surface (Moran, A. P. Carbohydr Res 343, 1952-1965 (2008)). Most bacterial sialyl- and fucosyl-transferases operate in the cytoplasm, i.e., they are better suited to the methods described herein than are eukaryotic golgi-localized sugar transferases.

Strains of *E. coli* engineered to express the transferases described above accumulate a cytoplasmic pool of lactose, as well as an additional pool of either the nucleotide sugar GDP-fucose, or the nucleotide sugar CMP-Neu5Ac (CMP-sialic acid). Addition of these sugars to the lactose acceptor is performed in these engineered hosts using candidate recombinant α(1,3)-fucosyl- or α(2,3)-sialyl-transferases, generating 3-fucosyllactose and 3'-sialyllactose respectively. Finally, the two synthetic capabilities are combined into a single *E. coli* strain to produce 3'-S3FL.

An *E. coli* strain that accumulates cytoplasmic pools of both lactose and GDP-fucose has been developed. This strain, when transformed with a plasmid over-expressing an α(1,2)fucosyltransferase, produces 2'-fucosyllactose (2'-FL) at levels of ~10-50 g/L of bacterial culture medium. A substitution of the α(1,2) fucosyltransferase in this host with an appropriate α(1,3) fucosyltransferase leads to the production of 3-fucosyllactose (3FL). The bacterial α(1,3) fucosyltransferase then works in conjunction with a bacterial α(2,3)sialyltransferaseto make the desired product, 3'-S3FL.

An α(1,3)fucosyltransferase (Hh0072) isolated from *Helicobacter hepaticus* exhibits activity towards both non-sialylated and sialylated Type 2 oligosaccharide acceptor substrates (Zhang, L., Lau, K., Cheng, J., Yu, H., et al. Glycobiology (2010)). This enzyme is cloned, expressed, and evaluated to measure utilization of a lactose acceptor and to evaluate production of 3FL in the context of the current GDP-fucose-producing *E. coli* host. Hh0072 is also tested in concert with various bacterial α(2,3)sialyltransferases for its competence in 3'-S3FL synthesis. As alternatives to Hh0072, there are two characterized homologous bacterial-type 3-fucosyltransferases identified in *Helicobacter pylori*, "11639 FucTa" (Ge, Z., Chan, N. W., Palcic, M. M. & Taylor, D. E. J Biol Chem 272, 21357-21363 (1997); Martin, S. L., Edbrooke, M. R., Hodgman, T. C., van den Eijnden, D. H. & Bird, M. I. J Biol Chem 272, 21349-21356 (1997)) and "UA948 FucTa" (Rasko, D. A., Wang, G., Palcic, M. M. & Taylor, D. E. J Biol Chem 275, 4988-4994 (2000)). These two paralogs exhibit differing acceptor specificities, "11639 FucTa" utilizes only Type 2 acceptors and is a strict a(1,3)-fucosyltransferase, whereas "UA948 FucTa" has relaxed acceptor specificity (utilizing both Type1 and Type 2 acceptors) and is able to generate both α(1,3)- and α(1,4)-fucosyl linkages. The precise molecular basis of this difference in specificity was determined (Ma, B., Lau, L. H., Palcic, M. M., Hazes, B. & Taylor, D. E. J Biol Chem 280, 36848-36856 (2005)), and characterization of several additional α(1,3)-fucosyltransferase paralogs from a variety of additional *H. pylori* strains revealed significant strain-to-strain acceptor specificity diversity.

In addition to the enzymes from *H. pylori* and *H. hepaticus*, other bacterial α(1,3)-fucosyltransferases are optionally used. For example, close homologs of Hh0072 are found in *H. bilis* (HRAG_01092 gene, sequence accession EEO24035), and in *C. jejuni* (C1336_000250319 gene, sequence accession EFC31050).

Described below is 3'-S3FL synthesis in *E. coli*. The first step towards this is to combine into a single *E. coli* strain the 3-fucosyllactose synthetic ability, outlined above, with the ability to make 3'-sialyllactose, also outlined above. All of the chromosomal genetic modifications discussed above are introduced into a new host strain, which will then simultaneously accumulate cytoplasmic pools of the 3 specific precursors; lactose, GDP-fucose and CMP-Neu5Ac. This "combined" strain background is then used to host simultaneous production of an α(1,3)fucosyltransferase with an α(2,3)sialyltransferase, with gene expression driven either off two compatible multicopy plasmids or with both enzyme genes positioned on the same plasmid as an artificial operon. Acceptor specificities for some of the bacterial α(1,3)fucosyltransferases and α(2,3)sialyltransferases, particularly with respect to fucosylation of 3'-sialyllactose and sialylation of 3-fucosyllactose and different combinations of α(1,3)fucosyltransferase and α(2,3)sialyltransferase enzymes are evaluated. Production levels and ratios of 3'-SL, 3FL and 3'-S3FL are monitored, e.g., by TLC, with confirmation of identity by NMR and accurate quantitation either by calibrated mass spectrometry utilizing specific ion monitoring, or by capillary electrophoresis (Bao, Y., Zhu, L. & Newburg, D. S. Simultaneous quantification of sialyloligosaccharides from human milk by capillary electrophoresis. Anal Biochem 370, 206-214 (2007)).

The sequences corresponding to the SEQ ID NOs described herein are provided below. The sequence of PG175 is set forth below (SEQ ID NO: 1):

```
TCGCGCGTTTCGGTGATGACGGTGAAAACCTCTGACACATGCAGCTCCC

GGAGACGGTCACAGCTTGTCTGTAAGCGGATGCCGGGAGCAGACAAGCC

CGTCAGGGCGCGTCAGCGGGTGTTGGCGGGTGTCGGGGCTGGCTTAACT

ATGCGGCATCAGAGCAGATTGTACTGAGAGTGCACCATATATGCGGTGT

GAAATACCGCACAGATGCGTAAGGAGAAAATACCGCATCAGGCGCCTCC

TCAACCTGTATATTCGTAAACCACGCCCAATGGGAGCTGTCTCAGGTTT

GTTCCTGATTGGTTACGGCGCGTTTCGCATCATTGTTGAGTTTTTCCGC

CAGCCCGACGCGCAGTTTACCGGTGCCTGGGTGCAGTACATCAGCATGG
```

```
GGCAAATTCTTTCCATCCCGATGATTGTCGCGGGTGTGATCATGATGGT
CTGGGCATATCGTCGCAGCCCACAGCAACACGTTTCCTGAGGAACCATG
AAACAGTATTTAGAACTGATGCAAAAAGTGCTCGACGAAGGCACACAGA
AAAACGACCGTACCGGAACCGGAACGCTTTCCATTTTTGGTCATCAGAT
GCGTTTTAACCTGCAAGATGGATTCCCGCTGGTGACAACTAAACGTTGC
CACCTGCGTTCCATCATCCATGAACTGCTGTGGTTTCTGCAGGGCGACA
CTAACATTGCTTATCTACACGAAAACAATGTCACCATCTGGGACGAATG
GGCCGATGAAAACGGCGACCTCGGGCCAGTGTATGGTAAACAGTGGCGC
GCCTGGCCAACGCCAGATGGTCGTCATATTGACCAGATCACTACGGTAC
TGAACCAGCTGAAAAACGACCCGGATTCGCGCCGCATTATTGTTTCAGC
GTGGAACGTAGGCGAACTGGATAAAATGGCGCTGGCACCGTGCCATGCA
TTCTTCCAGTTCTATGTGGCAGACGGCAAACTCTCTTGCCAGCTTTATC
AGCGCTCCTGTGACGTCTTCCTCGGCCTGCCGTTCAACATTGCCAGCTA
CGCGTTATTGGTGCATATGATGGCGCAGCAGTGCGATCTGGAAGTGGGT
GATTTTGTCTGGACCGGTGGCGACACGCATCTGTACAGCAACCATATGG
ATCAAACTCATCTGCAATTAAGCCGCGAACCGCGTCCGCTGCCGAAGTT
GATTATCAAACGTAAACCCGAATCCATCTTCGACTACCGTTTCGAAGAC
TTTGAGATTGAAGGCTACGATCCGCATCCGGGCATTAAAGCGCCGGTGG
CTATCTAATTACGAAACATCCTGCCAGAGCCGACGCCAGTGTGCGTCGG
TTTTTTTACCCTCCGTTAAATTCTTCGAGACGCCTTCCCGAAGGCGCCA
TTCGCCATTCAGGCTGCGCAACTGTTGGGAAGGGCGATCGGTGCGGGCC
TCTTCGCTATTACGCCAGCTGGCGAAAGGGGATGTGCTGCAAGGCGAT
TAAGTTGGGTAACGCCAGGGTTTTCCCAGTCACGACGTTGTAAAACGAC
GGCCAGTGCCAAGCTTTCTTTAATGAAGCAGGGCATCAGGACGGTATCT
TTGTGGAGAAAGCAGAGTAATCTTATTCAGCCTGACTGGTGGGAAACCA
CCAGTCAGAATGTGTTAGCGCATGTTGACAAAAATACCATTAGTCACAT
TATCCGTCAGTCGGACGACATGGTAGATAACCTGTTTATTATGCGTTTT
GATCTTACGTTTAATATTACCTTTATGCGATGAAACGGTCTTGGCTTTG
ATATTCATTTGGTCAGAGATTTGAATGGTTCCCTGACCTGCCATCCACA
TTCGCAACATACTCGATTCGGTTCGGCTCAATGATAACGTCGGCATATT
TAAAAACGAGGTTATCGTTGTCTCTTTTTTCAGAATATCGCCAAGGATA
TCGTCGAGAGATTCCGGTTTAATCGATTTAGAACTGATCAATAAATTTT
TTCTGACCAATAGATATTCATCAAAATGAACATTGGCAATTGCCATAAA
AACGATAAATAACGTATTGGGATGTTGATTAATGATGAGCTTGATACGC
TGACTGTTAGAAGCATCGTGGATGAAACAGTCCTCATTAATAAACACCA
CTGAAGGGCGCTGTGAATCACAAGCTATGGCAAGGTCATCAACGGTTTC
AATGTCGTTGATTTCTCTTTTTTTAACCCCTCTACTCAACAGATACCCG
GTTAAACCTAGTCGGGTGTAACTACATAAATCCATAATAATCGTTGACA
TGGCATACCCTCACTCAATGCGTAACGATAATTCCCCTTACCTGAATAT
TTCATCATGACTAAACGGAACAACATGGGTCACCTAATGCGCCACTCTC
```
```
GCGATTTTTCAGGCGGACTTACTATCCCGTAAAGTGTTGTATAATTTGC
CTGGAATTGTCTTAAAGTAAAGTAAATGTTGCGATATGTGAGTGAGCTT
AAAACAAATATTTCGCTGCAGGAGTATCCTGGAAGATGTTCGTAGAAGC
TTACTGCTCACAAGAAAAAGGCACGTCATCTGACGTGCCTTTTTTATT
TGTACTACCCTGTACGATTACTGCAGCTCGAGTTATTATAATTTTACCC
ACGATTCGGGAATAATATCATGTTTAATATCTTTCTTAAACCATTTACT
CGGAGCAATTACTGTTTTATTTTTATTTTCATTTAACCAAGCAGCCCAC
CAACTGAAAGAACTATTTGAAATTATATTATTTTTACATTTACTCATAA
GCAGCATATCTAATTCAACATGATAAGCATCACCTTGAACAAAACATAT
TTGATTATTAAAAAATATATTTTCCCTGCACCACTTTATATCATCAGAA
AAAATGAAGAGAAGGGTTTTTTTATTAATAACACCTTTATTCATCAAAT
AATCAATGGCACGTTCAAAATATTTTTCACTACATGTGCCATGAGTTTC
ATTTGCTATTTTACTGGAAACATAATCACCTCTTCTAATATGTAATGAA
CAAGTATCATTTTCTTTAATTAAATTAAGCAATTCATTTTGATAACTAT
TAAACTTGGTTTTAGGTTGAAATTCCTTTATCAACTCATGCCTAAATTC
CTTAAAATATTTTTCAGTTTGAAAATAACCGACGATTTTTTTATTTATA
CTTTTGGTATCAATATCTGGATCATACTCTAAACTTTTCTCAACGTAAT
GCTTTCTGAACATTCCTTTTTTCATGAAATGTGGGATTTTTTCGGAAAA
TAAGTATTTTTCAAATGGCCATGCTTTTTTTACAAATTCTGAACTACAA
GATAATTCAACTAATCTTAATGGATGAGTTTTATATTTTACTGCATCAG
ATATATCAACAGTCAAATTTTGATGAGTTCTTTTTGCAATAGCAAATGC
AGTTGCATACTGAAACATTTGATTACCAAGACCACCAATAATTTTAACT
TCCATATGTATATCTCCTTCTTCTAGAATTCTAAAAATTGATTGAATGT
ATGCAAATAAATGCATACACCATAGGTGTGGTTTAATTTGATGCCCTTT
TTCAGGGCTGGAATGTGTAAGAGCGGGGTTATTTATGCTGTTGTTTTTT
TGTTACTCGGGAAGGGCTTTACCTCTTCCGCATAAACGCTTCCATCAGC
GTTTATAGTTAAAAAAATCTTTCGGAACTGGTTTTGCGCTTACCCCAAC
CAACAGGGGATTTGCTGCTTTCCATTGAGCCTGTTTCTCTGCGCGACGT
TCGCGGCGGCGTGTTTGTGCATCCATCTGGATTCTCCTGTCAGTTAGCT
TTGGTGGTGTGTGGCAGTTGTAGTCCTGAACGAAAACCCCCCGCGATTG
GCACATTGGCAGCTAATCCGGAATCGCACTTACGGCCAATGCTTCGTTT
CGTATCACACACCCCAAAGCCTTCTGCTTTGAATGCTGCCCTTCTTCAG
GGCTTAATTTTTAAGAGCGTCACCTTCATGGTGGTCAGTGCGTCCTGCT
GATGTGCTCAGTATCACCGCCAGTGGTATTTATGTCAACACCGCCAGAG
ATAATTTATCACCGCAGATGGTTATCTGTATGTTTTTATATGAATTTA
TTTTTTGCAGGGGGGCATTGTTTGGTAGGTGAGAGATCAATTCTGCATT
AATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGG
CGAGCGGTATCAGCTCACTCAAAGGCGGTAATACGGTTATCCACAGAAT
```

-continued

```
CAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAA
ACCCGACAGGACTATAAAGATACCAGGCGTTTCCCCCTGGAAGCTCCCT
CGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTT
GAGTCCAACCCGGTAAGACACGACTTATCGCCACTGGCAGCAGCCACTG
GTAACAGGATTAGCAGAGCGAGGTATGTAGGCGGTGCTACAGAGTTCTT
GAAGTGGTGGCCTAACTACGGCTACACTAGAAGGACAGTATTTGGTATC
TGCGCTCTGCTGAAGCCAGTTACCTTCGGAAAAGAGTTGGTAGCTCTT
GATCCGGCAAACAAACCACCGCTGGTAGCGGTGGTTTTTTTGTTTGCAA
GCAGCAGATTACGCGCAGAAAAAAAGGATCTCAAGAAGATCCTTTGATC
TTTTCTACGGGGTCTGACGCTCAGTGGAACGAAAACTCACGTTAAGGGA
TTTTGGTCATGAGATTATCAAAAAGGATCTTCACCTAGATCCTTTTAAA
TTAAAAATGAAGTTTTAAATCAATCTAAAGTATATATGAGTAAACTTGG
TCTGACAGTTACCAATGCTTAATCAGTGAGGCACCTATCTCAGCGATCT
GTCTATTTCGTTCATCCATAGTTGCCTGACTCCCCGTCGTGTAGATAAC
TACGATACGGGAGGGCTTACCATCTGGCCCCAGTGCTGCAATGATACCG
CGAGACCCACGCTCACCGGCTCCAGATTTATCAGCAATAAACCAGCCAG
CCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTT
AATAGTTTGCGCAACGTTGTTGCCATTGCTACAGGCATCGTGGTGTCAC
GCTCGTCGTTTGGTATGGCTTCATTCAGCTCCGGTTCCCAACGATCAAG
GCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCA
TGGTTATGGCAGCACTGCATAATTCTCTTACTGTCATGCCATCCGTAAG
ATGCTTTTCTGTGACTGGTGAGTACTCAACCAAGTCATTCTGAGAATAG
TGTATGCGGCGACCGAGTTGCTCTTGCCCGGCGTCAATACGGGATAATA
CCGCGCCACATAGCAGAACTTTAAAAGTGCTCATCATTGGAAAACGTTC
TTCGGGGCGAAAACTCTCAAGGATCTTACCGCTGTTGAGATCCAGTTCG
ATGTAACCCACTCGTGCACCCAACTGATCTTCAGCATCTTTTACTTTCA
CCAGCGTTTCTGGGTGAGCAAAAACAGGAAGGCAAAATGCCGCAAAAAA
GGGAATAAGGGCGACACGGAAATGTTGAATACTCATACTCTTCCTTTTT
CAATATTATTGAAGCATTTATCAGGGTTATTGTCTCATGAGCGGATACA
TATTTGAATGTATTTAGAAAAATAAACAAATAGGGGTTCCGCGCACATT
TCCCCGAAAAGTGCCACCTGACGTCTAAGAAACCATTATTATCATGACA
TTAACCTATAAAAATAGGCGTATCACGAGGCCCTTTCGTC
```

The sequence of pG176 is set forth below (SEQ ID NO: 2):

```
TCGCGCGTTTCGGTGATGACGGTGAAAACCTCTGACACATGCAGCTCCC
GGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACT
ATGCGGCATCAGAGCAGATTGTACTGAGAGTGCACCATATATGCGGTGT
GAAATACCGCACAGATGCGTAAGGAGAAAATACCGCATCAGGCGCCATG
AAACAGTATTTAGAACTGATGCAAAAAGTGCTCGACGAAGGCACACAGA
AAAACGACCGTACCGGAACCGGAACGCTTTCCATTTTTGGTCATCAGAT
GCGTTTTAACCTGCAAGATGGATTCCCGCTGGTGACAACTAAACGTTGC
CACCTGCGTTCCATCATCCATGAACTGCTGTGGTTTCTGCAGGGCGACA
CTAACATTGCTTATCTACACGAAAACAATGTCACCATCTGGGACGAATG
GGCCGATGAAAACGGCGACCTCGGGCCAGTGTATGGTAAACAGTGGCGC
GCCTGGCCAACGCCAGATGGTCGTCATATTGACCAGATCACTACGGTAC
TGAACCAGCTGAAAAACGACCCGGATTCGCGCCGCATTATTGTTTCAGC
GTGGAACGTAGGCGAACTGGATAAAATGGCGCTGGCACCGTGCCATGCA
TTCTTCCAGTTCTATGTGGCAGACGGCAAACTCTCTTGCCAGCTTTATC
AGCGCTCCTGTGACGTCTTCCTCGGCCTGCCGTTCAACATTGCCAGCTA
CGCGTTATTGGTGCATATGATGGCGCAGCAGTGCGATCTGGAAGTGGGT
GATTTTGTCTGGACCGGTGGCGACACGCATCTGTACAGCAACCATATGG
ATCAAACTCATCTGCAATTAAGCCGCGAACCGCGTCCGCTGCCGAAGTT
GATTATCAAACGTAAACCCGAATCCATCTTCGACTACCGTTTCGAAGAC
TTTGAGATTGAAGGCTACGATCCGCATCCGGGCATTAAAGCGCCGGTGG
CTATCTAAGGCGCCATTCGCCATTCAGGCTGCGCAACTGTTGGGAAGGG
CGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACG
ACGTTGTAAAACGACGGCCAGTGCCAAGCTTTCTTTAATGAAGCAGGGC
ATCAGGACGGTATCTTTGTGGAGAAAGCAGAGTAATCTTATTCAGCCTG
ACTGGTGGGAAACCACCAGTCAGAATGTGTTAGCGCATGTTGACAAAAA
TACCATTAGTCACATTATCCGTCAGTCGGACGACATGGTAGATAACCTG
TTTATTATGCGTTTTGATCTTACGTTTAATATTACCTTTATGCGATGAA
ACGGTCTTGGCTTTGATATTCATTTGGTCAGAGATTTGAATGGTTCCCT
GACCTGCCATCCACATTCGCAACATACTGATTCGGTTCGGCTCAATGA
TAACGTCGGCATATTTAAAAACGAGGTTATCGTTGTCTCTTTTTTCAGA
ATATCGCCAAGGATATCGTCGAGAGATTCCGGTTTAATCGATTTAGAAC
TGATCAATAAATTTTTTCTGACCAATAGATATTCATCAAAATGAACATT
GGCAATTGCCATAAAAACGATAAATAACGTATTGGGATGTTGATTAATG
ATGAGCTTGATACGCTGACTGTTAGAAGCATCGTGGATGAAACAGTCCT
CATTAATAAACACCACTGAAGGGCGCTGTGAATCACAAGCTATGGCAAG
GTCATCAACGGTTTCAATGTCGTTGATTTCTCTTTTTTTAACCCCTCTA
CTCAACAGATACCCGGTTAAACCTAGTCGGGTGTAACTACATAAATCCA
```

TAATAATCGTTGACATGGCATACCCTCACTCAATGCGTAACGATAATTC
CCCTTACCTGAATATTTCATCATGACTAAACGGAACAACATGGGTCACC
TAATGCGCCACTCTCGCGATTTTTCAGGCGGACTTACTATCCCGTAAAG
TGTTGTATAATTTGCCTGGAATTGTCTTAAAGTAAAGTAAATGTTGCGA
TATGTGAGTGAGCTTAAAACAAATATTTCGCTGCAGGAGTATCCTGGAA
GATGTTCGTAGAAGCTTACTGCTCACAAGAAAAAGGCACGTCATCTGA
CGTGCCTTTTTTATTTGTACTACCCTGTACGATTACTGCAGCTCGAGTT
AATTCAAATCTTCTTCAGAAATCAATTTTTGTTCCAAACCCAATTTTTT
AACCAACTTTCTCACCGCGCGCAACAAAGGCAAGGATTTTTGATAAGCT
TTGCGATAGATTTTAAAAGTGGTGTTTTGAGAGAGTTCTAATAAAGGCG
AAGCGTTTTGTAAAAGCCGGTCATAATTAACCCTCAAATCATCATAATT
AACCCTCAAATCATCAATGGATACTAACGGCTTATGCAGATCGTACTCC
CACATGAAAGATGTTGAGAATTTGTGATAAATCGTATCGTTTTCTAAAA
TCGTTTTAAAAAAATCTAGGATTTTTTAAAACTCAAATCTTGGTAAAA
GTAAGCTTTCCCATCAAGGGTGTTTAAAGGGTTTTCATAGAGCATGTCT
AAATAAGCGTTTGGGTGCGTGTGCAGGTATTTGATATAATCAATCGCTT
CATCAAAGTTGTTGAAATCATGCACATTCACAAAACTTTTAGGGTTAAA
ATCTTTCGCCACGCTGGGACTCCCCAATAAATAGGAATGGTATGGCTA
AAATACGCATCAAGGATTTTTTCGGTTACATAGCCATAACCTTGCGAGT
TTTCAAAACAGAGATTGAACTTGTATTGGCTTAAAAACTCGCTTTTGTT
TCCAACCTTATAGCCTAAAGTGTTTCTCACACTTCCTCCCCCAGTAACT
GGCTCTATGGAATTTAGAGCGTCATAAAAAGCGTTCCTCATAGGAGCGT
TAGCGTTGCTCGCTACAAAACTGGCAAACCCTCTTTTTAAAAGATCGCT
CTCATCATTCACTACTGCGCACAAATTAGGGTGGTTTTCTTTAAAATGA
TGAGAGGGTTTTTTAAAGCATAAAGGCTGTTGTCTTTGAGTTTGTAGG
GCGCAGTGGTGTCATTAACAAGCTCGGCTTTATAGTGCAAATGGGCATA
ATACAAAGGCATTCTCAAATAACGATCATTAAAATCCAATTCATCAAAG
CCTATGGCGTAATCAAAGAGGTTGAAATTAGGTGATTCGTTTTCACCGG
TGTAAAACACTCGTTTAGTGTTTTGATAAGATAAAATCTTTCTAGCCGC
TCCAAGAGGATTGCTAAAAACTAGATCTGAAAATTCATTGGGGTTTTGG
TGGAGGGTGATTGCGTAGCGTTGGCTTAGGATAAAATAAAGAACGCTCT
TTTTAAATTCTTTAATTTCTTCATCTCCCCACCAATTCGCCACAGCGAT
TTTTAGGGGGGGGGGGAGATTTAGAGGCCATTTTTTCAATGGAAGCG
CTTTCTATAAAGGCGTCTAATAGGGGTTGGAACATATGTATATCTCCTT
CTTGAATTCTAAAAATTGATTGAATGTATGCAAATAAATGCATACACCA
TAGGTGTGGTTTAATTTGATGCCCTTTTTCAGGGCTGGAATGTGTAAGA
GCGGGGTTATTTATGCTGTTGTTTTTTGTTACTCGGGAAGGGCTTTAC
CTCCTTCCGCATAAACGCTTCCATCAGCGTTTATAGTTAAAAAAATCTTT
CGGAACTGGTTTTGCGCTTACCCCAACCAACAGGGGATTTGCTGCTTTC
CATTGAGCCTGTTTCTCTGCGCGACGTTCGCGGCGGCGTGTTTGTGCAT

CCATCTGGATTCTCCTGTCAGTTAGCTTTGGTGGTGTGTGGCAGTTGTA
GTCCTGAACGAAAACCCCCCGCGATTGGCACATTGGCAGCTAATCCGGA
ATCGCACTTACGGCCAATGCTTCGTTTCGTATCACACACCCCAAAGCCT
TCTGCTTTGAATGCTGCCCTTCTTCAGGGCTTAATTTTTAAGAGCGTCA
CCTTCATGGTGGTCAGTGCGTCCTGCTGATGTGCTCAGTATCACCGCCA
GTGGTATTTATGTCAACACCGCCAGAGATAATTTATCACCGCAGATGGT
TATCTGTATGTTTTTTATATGAATTTATTTTTTGCAGGGGGGCATTGTT
TGGTAGGTGAGAGATCAATTCTGCATTAATGAATCGGCCAACGCGCGGG
GAGAGGCGGTTTGCGTATTGGGCGCTCTTCCGCTTCCTCGCTCACTGAC
TCGCTGCGCTCGGTCGTTCGGCTGCGGCGAGCGGTATCAGCTCACTCAA
AGGCGGTAATACGGTTATCCACAGAATCAGGGGATAACGCAGGAAAGAA
CATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAA
ATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGC
TGCGCCTTATCCGGTAACTATCGTCTTGAGTCCAACCCGGTAAGACACG
ACTTATCGCCACTGGCAGCAGCCACTGGTAACAGGATTAGCAGAGCGAG
GTATGTAGGCGGTGCTACAGAGTTCTTGAAGTGGTGGCCTAACTACGGC
TACACTAGAAGGACAGTATTTGGTATCTGCGCTCTGCTGAAGCCAGTTA
CCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTC
AGTGGAACGAAAACTCACGTTAAGGGATTTTGGTCATGAGATTATCAAA
AAGGATCTTCACCTAGATCCTTTTAAATTAAAAATGAAGTTTTAAATCA
ATCTAAAGTATATATGAGTAAACTTGGTCTGACAGTTACCAATGCTTAA
TCAGTGAGGCACCTATCTCAGCGATCTGTCTATTTCGTTCATCCATAGT
TGCCTGACTCCCCGTCGTGTAGATAACTACGATACGGGAGGGCTTACCA
TCTGGCCCCAGTGCTGCAATGATACCGCGAGACCCACGCTCACCGGCTC
CAGATTTATCAGCAATAAACCAGCCAGCCGGAAGGGCCGAGCGCAGAAG
TGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTC
ATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAA
TTCTCTTACTGTCATGCCATCCGTAAGATGCTTTTCTGTGACTGGTGAG
TACTCAACCAAGTCATTCTGAGAATAGTGTATGCGGCGACCGAGTTGCT
CTTGCCCGGCGTCAATACGGGATAATACCGCGCCACATAGCAGAACTTT

-continued

AAAAGTGCTCATCATTGGAAAACGTTCTTCGGGGCGAAAACTCTCAAGG

ATCTTACCGCTGTTGAGATCCAGTTCGATGTAACCCACTCGTGCACCCA

ACTGATCTTCAGCATCTTTTACTTTCACCAGCGTTTCTGGGTGAGCAAA

AACAGGAAGGCAAAATGCCGCAAAAAAGGGAATAAGGGCGACACGGAAA

TGTTGAATACTCATACTCTTCCTTTTTCAATATTATTGAAGCATTTATC

AGGGTTATTGTCTCATGAGCGGATACATATTTGAATGTATTTAGAAAAA

TAAACAAATAGGGGTTCCGCGCACATTTCCCCGAAAAGTGCCACCTGAC

GTCTAAGAAACCATTATTATCATGACATTAACCTATAAAAATAGGCGTA

TCACGAGGCCCTTTCGTC

The sequence of pG177 is set forth below (SEQ ID NO: 3):

TCGCGCGTTTCGGTGATGACGGTGAAAACCTCTGACACATGCAGCTCCC

GGAGACGGTCACAGCTTGTCTGTAAGCGGATGCCGGGAGCAGACAAGCC

CGTCAGGGCGCGTCAGCGGGTGTTGGCGGGTGTCGGGGCTGGCTTAACT

ATGCGGCATCAGAGCAGATTGTACTGAGAGTGCACCATATATGCGGTGT

GAAATACCGCACAGATGCGTAAGGAGAAAATACCGCATCAGGCGCCATG

AAACAGTATTTAGAACTGATGCAAAAAGTGCTCGACGAAGGCACACAGA

AAAACGACCGTACCGGAACCGGAACGCTTTCCATTTTTGGTCATCAGAT

GCGTTTTAACCTGCAAGATGGATTCCCGCTGGTGACAACTAAACGTTGC

CACCTGCGTTCCATCATCCATGAACTGCTGTGGTTTCTGCAGGGCGACA

CTAACATTGCTTATCTACACGAAAACAATGTCACCATCTGGGACGAATG

GGCCGATGAAAACGGCGACCTCGGGCCAGTGTATGGTAAACAGTGGCGC

GCCTGGCCAACGCCAGATGGTCGTCATATTGACCAGATCACTACGGTAC

TGAACCAGCTGAAAAACGACCCGGATTCGCGCCGCATTATTGTTTCAGC

GTGGAACGTAGGCGAACTGGATAAAATGGCGCTGGCACCGTGCCATGCA

TTCTTCCAGTTCTATGTGGCAGACGGCAAACTCTCTTGCCAGCTTTATC

AGCGCTCCTGTGACGTCTTCCTCGGCCTGCCGTTCAACATTGCCAGCTA

CGCGTTATTGGTGCATATGATGGCGCAGCAGTGCGATCTGGAAGTGGGT

GATTTTGTCTGGACCGGTGGCGACACGCATCTGTACAGCAACCATATGG

ATCAAACTCATCTGCAATTAAGCCGCGAACCGCGTCCGCTGCCGAAGTT

GATTATCAAACGTAAACCCGAATCCATCTTCGACTACCGTTTCGAAGAC

TTTGAGATTGAAGGCTACGATCCGCATCCGGGCATTAAAGCGCCGGTGG

CTATCTAAGGCGCCATTCGCCATTCAGGCTGCGCAACTGTTGGGAAGGG

CGATCGGTGCGGGCCTCTTCGCTATTACGCCAGCTGGCGAAAGGGGGAT

GTGCTGCAAGGCGATTAAGTTGGGTAACGCCAGGGTTTTCCCAGTCACG

ACGTTGTAAAACGACGGCCAGTGCCAAGCTTTCTTTAATGAAGCAGGGC

ATCAGGACGGTATCTTTGTGGAGAAAGCAGAGTAATCTTATTCAGCCTG

ACTGGTGGGAAACCACCAGTCAGAATGTGTTAGCGCATGTTGACAAAAA

TACCATTAGTCACATTATCCGTCAGTCGGACGACATGGTAGATAACCTG

TTTATTATGCGTTTTGATCTTACGTTTAATATTACCTTTATGCGATGAA

ACGGTCTTGGCTTTGATATTCATTTGGTCAGAGATTTGAATGGTTCCCT

GACCTGCCATCCACATTCGCAACATACTCGATTCGGTTCGGCTCAATGA

TAACGTCGGCATATTTAAAAACGAGGTTATCGTTGTCTCTTTTTTCAGA

ATATCGCCAAGGATATCGTCGAGAGATTCCGGTTTAATCGATTTAGAAC

TGATCAATAAATTTTTTCTGACCAATAGATATTCATCAAAATGAACATT

GGCAATTGCCATAAAAACGATAAATAACGTATTGGGATGTTGATTAATG

ATGAGCTTGATACGCTGACTGTTAGAAGCATCGTGGATGAAACAGTCCT

CATTAATAAACACCACTGAAGGGCGCTGTGAATCACAAGCTATGGCAAG

GTCATCAACGGTTTCAATGTCGTTGATTTCTCTTTTTTTAACCCCTCTA

CTCAACAGATACCCGGTTAAACCTAGTCGGGTGTAACTACATAAATCCA

TAATAATCGTTGACATGGCATACCCTCACTCAATGCGTAACGATAATTC

CCCTTACCTGAATATTTCATCATGACTAAACGGAACAACATGGGTCACC

TAATGCGCCACTCTCGCGATTTTTCAGGCGGACTTACTATCCCGTAAAG

TGTTGTATAATTTGCCTGGAATTGTCTTAAAGTAAAGTAAATGTTGCGA

TATGTGAGTGAGCTTAAAACAAATATTTCGCTGCAGGAGTATCCTGGAA

GATGTTCGTAGAAGCTTACTGCTCACAAGAAAAAAGGCACGTCATCTGA

CGTGCCTTTTTTATTTGTACTACCCTGTACGATTACTGCAGCTCGAGTT

AATTCAAATCTTCTTCAGAAATCAATTTTTGTTCAGCGTTATACTTTTG

GGATTTTACCTCAAAATGGGATTCTATTTTCACCCACTCCTTACAAAGG

ATATTCTCATGCCCAAAAAGCCAGTGTTTGGGGCCAATAATGATTTTTT

CTGGATTTTCTATCAAATAGGCCGCCCACCAGCTATAAGTGCTATTAGC

GATAATGCCATGCTGACAAGATTGCATGAGCAGCATGTCCCAATACGCC

TCTTCTTCTTTATCCCTAGTGGTCATGTCCATAAAAGGGTAGCCAAGAT

CAAGATTTTGCGTGAATTCTAAGTCTTCGCAAAACACAAAAAGCTCCAT

GTTTGGCACGCGCTTTGCCATATACTCAAGCGCCTTTTTTTGATAGTCA

ATACCAAGCTGACAGCCAATCCCCACATAATCCCCTCTTCTTATATGCA

CAAAACACGCTGTTTTTAGCGGCTAAAATCAAAGAAAGCTTGCACTGATA

TTCTTCCTCTTTTTTATTATTATTCTTATTATTTTCGGGTGGTGGTGGT

AGAGTGAAGGTTTGCTTGATTAAAGGGGATATAGCATCAAAGTATCGTG

GATCTTGGAAATAGCCAAAAAAATAAGTCAAGCGGCTTGGCTTTAGCAA

TTTAGGCTCGTATTCAAAAACGATTTCTTGACTCACCCTATCAAATCCC

ATGCATTTGAGCGCGTCTCTTACTAGCTTGGGGAGGTGTTGCATTTTAG

CTATAGCGATTTCTTTCGCGCTCGCATAGGGCAAATCAATAGGGAAAAG

TTCTAATTGCATTTTCCTATCGCTCCAATCAAAAGAAGTGATATCTAAC

AGCACAGGCGTATTAGAGTGTTTTTGCAAACTTTTAGCGAAAGCGTATT

GAAACATTTGATTCCCAAGCCCTCCGCAAATTTGCACCACCTTAAAAGC

CATATGTATATCTCCTTCTTGCTCGAGTTAATTCAAATCTTCTTCAGAA

ATCAATTTTTGTTCCAAACCCAATTTTTTAACCAACTTTCTCACCGCGC

GCAACAAAGGCAAGGATTTTTGATAAGCTTTGCGATAGATTTTAAAAGT

GGTGTTTTGAGAGAGTTCTAATAAAGGCGAAGCGTTTTGTAAAAGCCGG

-continued

```
TCATAATTAACCCTCAAATCATCATAATTAACCCTCAAATCATCAATGG
ATACTAACGGCTTATGCAGATCGTACTCCCACATGAAAGATGTTGAGAA
TTTGTGATAAATCGTATCGTTTTCTAAAATCGTTTTAAAAAAATCTAGG
ATTTTTTTAAAACTCAAATCTTGGTAAAAGTAAGCTTTCCCATCAAGGG
TGTTTAAAGGGTTTTCATAGAGCATGTCTAAATAAGCGTTTGGGTGCGT
GTGCAGGTATTTGATATAATCAATCGCTTCATCAAAGTTGTTGAAATCA
TGCACATTCACAAAACTTTTAGGGTTAAAATCTTTCGCCACGCTGGGAC
TCCCCCAATAAATAGGAATGGTATGGCTAAAATACGCATCAAGGATTTT
TTCGGTTACATAGCCATAACCTTGCGAGTTTTCAAAACAGAGATTGAAC
TTGTATTGGCTTAAAAACTCGCTTTTGTTTCCAACCTTATAGCCTAAAG
TGTTTCTCACACTTCCTCCCCCAGTAACTGGCTCTATGGAATTTAGAGC
GTCATAAAAAGCGTTCCTCATAGGAGCGTTAGCGTTGCTCGCTACAAAA
CTGGCAAACCCTCTTTTTAAAAGATCGCTCTCATCATTCACTACTGCGC
ACAAATTAGGGTGGTTTTCTTTAAAATGATGAGAGGGTTTTTTTAAAGC
ATAAAGGCTGTTGTCTTTGAGTTTGTAGGGCGCAGTGGTGTCATTAACA
AGCTCGGCTTTATAGTGCAAATGGGCATAATACAAAGGCATTCTCAAAT
AACGATCATTAAAATCCAATTCATCAAAGCCTATGGCGTAATCAAAGAG
GTTGAAATTAGGTGATTCGTTTTCACCGGTGTAAAACACTCGTTTAGTG
TTTTGATAAGATAAAATCTTTCTAGCGCTCCAAGAGGATTGCTAAAAA
CTAGATCTGAAAATTCATTGGGGTTTTGGTGGAGGGTGATTGCGTAGCG
TTGGCTTAGGATAAAATAAAGAACGCTCTTTTTAAATTCTTTAATTTCT
TCATCTCCCCACCAATTCGCCACAGCGATTTTTAGGGGGGGGGGGAG
ATTTAGAGGCCATTTTTTCAATGGAAGCGCTTTCTATAAAGGCGTCTAA
TAGGGGTTGGAACATATGTATATCTCCTTCTTGAATTCTAAAAATTGAT
TGAATGTATGCAAATAAATGCATACACCATAGGTGTGGTTTAATTTGAT
GCCCTTTTTCAGGGCTGGAATGTGTAAGAGCGGGGTTATTTATGCTGTT
GTTTTTTTGTTACTCGGGAAGGGCTTTACCTCTTCCGCATAAACGCTTC
CATCAGCGTTTATAGTTAAAAAAATCTTTCGGAACTGGTTTTGCGCTTA
CCCCAACCAACAGGGGATTTGCTGCTTTCCATTGAGCCTGTTTCTCTGC
GCGACGTTCGCGGCGGCGTGTTTGTGCATCCATCTGGATTCTCCTGTCA
GTTAGCTTTGGTGGTGTGTGGCAGTTGTAGTCCTGAACGAAAACCCCCC
GCGATTGGCACATTGGCAGCTAATCCGGAATCGCACTTACGGCCAATGC
TTCGTTTCGTATCACACACCCCAAAGCCTTCTGCTTTGAATGCTGCCCT
TCTTCAGGGCTTAATTTTTAAGAGCGTCACCTTCATGGTGGTCAGTGCG
TCCTGCTGATGTGCTCAGTATCACCGCCAGTGGTATTTATGTCAACACC
GCCAGAGATAATTTATCACCGCAGATGGTTATCTGTATGTTTTTTATAT
GAATTTATTTTTGCAGGGGGCATTGTTTGGTAGGTGAGAGATCAATT
CTGCATTAATGAATCGGCCAACGCGCGGGAGAGGCGGTTTGCGTATTG
GGCGCTCTTCCGCTTCCTCGCTCACTGACTCGCTGCGCTCGGTCGTTCG
GCTGCGGCGAGCGGTATCAGCTCACTCAAAGGCGGTAATACGGTTATCC
ACAGAATCAGGGGATAACGCAGGAAAGAACATGTGAGCAAAAGGCCAGC
```

-continued

```
AAAAGGCCAGGAACCGTAAAAAGGCCGCGTTGCTGGCGTTTTTCCATAG
GCTCCGCCCCCTGACGAGCATCACAAAAATCGACGCTCAAGTCAGAGG
TGGCGAAACCCGACAGGACTATAAAGATACCAGGCGTTTCCCCCTGGAA
GCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTA
TCGTCTTGAGTCCAACCCGGTAAGACACGACTTATCGCCACTGGCAGCA
GCCACTGGTAACAGGATTAGCAGAGCGAGGTATGTAGGCGGTGCTACAG
AGTTCTTGAAGTGGTGGCCTAACTACGGCTACACTAGAAGGACAGTATT
TGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTG
TTTGCAAGCAGCAGATTACGCGCAGAAAAAAAGGATCTCAAGAAGATCC
TTTGATCTTTTCTACGGGGTCTGACGCTCAGTGGAACGAAAACTCACGT
TAAGGGATTTTGGTCATGAGATTATCAAAAAGGATCTTCACCTAGATCC
TTTTAAATTAAAAATGAAGTTTTAAATCAATCTAAAGTATATATGAGTA
AACTTGGTCTGACAGTTACCAATGCTTAATCAGTGAGGCACCTATCTCA
GCGATCTGTCTATTTCGTTCATCCATAGTTGCCTGACTCCCCGTCGTGT
AGATAACTACGATACGGGAGGGCTTACCATCTGGCCCCAGTGCTGCAAT
GATACCGCGAGACCCACGCTCACCGGCTCCAGATTTATCAGCAATAAAC
CAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTC
GCCAGTTAATAGTTTGCGCAACGTTGTTGCCATTGCTACAGGCATCGTG
GTGTCACGCTCGTCGTTTGGTATGGCTTCATTCAGCTCCGGTTCCCAAC
GATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTA
TCACTCATGGTTATGGCAGCACTGCATAATTCTCTTACTGTCATGCCAT
CCGTAAGATGCTTTTCTGTGACTGGTGAGTACTCAACCAAGTCATTCTG
AGAATAGTGTATGCGGCGACCGAGTTGCTCTTGCCCGGCGTCAATACGG
GATAATACCGCGCCACATAGCAGAACTTTAAAAGTGCTCATCATTGGAA
AACGTTCTTCGGGGCGAAAACTCTCAAGGATCTTACCGCTGTTGAGATC
CAGTTCGATGTAACCCACTCGTGCACCCAACTGATCTTCAGCATCTTTT
ACTTTCACCAGCGTTTCTGGGTGAGCAAAAACAGGAAGGCAAAATGCCG
CAAAAAAGGGAATAAGGGCGACACGGAAATGTTGAATACTCATACTCTT
CCTTTTTCAATATTATTGAAGCATTTATCAGGGTTATTGTCTCATGAGC
GGATACATATTTGAATGTATTTAGAAAAATAAACAAATAGGGGTTCCGC
GCACATTTCCCCGAAAAGTGCCACCTGACGTCTAAGAAACCATTATTAT
CATGACATTAACCTATAAAAATAGGCGTATCACGAGGCCCTTTCGTC
```

The sequence of *Bacteroides fragilis* NCTC 9343 wcfW CDS DNA is set for the below (SEQ ID NO: 4):

ATGATTGTATCATCTTTGCGAGGAGGATTGGGGAATCAAATGTTTATTT
ACGCTATGGTGAAGGCCATGGCATTAAGAAACAATGTACCATTCGCTTT
TAATTTGACTACTGATTTTGCAAATGATGAAGTTTATAAAAGGAAACTT
TTATTATCATATTTTGCATTAGACTTGCCTGAAAATAAAAAATTAACAT
TTGATTTTTCATATGGGAATTATTATAGAAGGCTAAGTCGTAATTTAGG
TTGTCATATACTTCATCCATCATATCGTTATATTTGCGAAGAGCGCCCT
CCCCACTTTGAATCAAGGTTAATTAGTTCTAAGATTACAAATGCTTTTC
TGGAAGGATATTGGCAGTCAGAAAAATATTTTCTTGATTATAAACAAGA
GATAAAAGAGGACTTTGTAATACAAAAAAAATTAGAATACACATCGTAT
TTGGAATTGGAAGAAATAAAATTGCTAGATAAGAATGCCATAATGATTG
GGGTTAGACGGTATCAGGAAAGTGATGTAGCTCCTGGTGGAGTGTTAGA
AGATGATTACTATAAATGTGCTATGGATATTATGGCATCAAAAGTTACT
TCTCCTGTTTTCTTTTGTTTTCACAAGATTTAGAATGGGTTGAAAAAC
ATCTAGCGGGAAAATATCCTGTTCGTTTGATAAGTAAAAAGGAGGATGA
TAGTGGTACTATAGATGATATGTTTCTAATGATGCATTTTCGTAATTAT
ATAATATCGAATAGCTCTTTTTACTGGTGGGGAGCATGGCTTTCGAAAT
ATGATGATAAGCTGGTGATTGCTCCAGGTAATTTTATAAATAAGGATTC
TGTACCAGAATCTTGGTTTAAATTGAATGTAAGATAA

The sequence of pG171 is set forth below (SEQ ID NO: 5)

TCGCGCGTTTCGGTGATGACGGTGAAAACCTCTGACACATGCAGCTCCC
GGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACT
ATGCGGCATCAGAGCAGATTGTACTGAGAGTGCACCATATATGCGGTGT
GAAATACCGCACAGATGCGTAAGGAGAAAATACCGCATCAGGCGCCTCC
TCAACCTGTATATTCGTAAACCACGCCCAATGGGAGCTGTCTCAGGTTT
GTTCCTGATTGGTTACGGCGCGTTTCGCATCATTGTTGAGTTTTTCCGC
CAGCCCGACGCGCAGTTTACCGGTGCCTGGGTGCAGTACATCAGCATGG
GGCAAATTCTTTCCATCCCGATGATTGTCGCGGGTGTGATCATGATGGT
CTGGGCATATCGTCGCAGCCCACAGCAACACGTTTCCTGAGGAACCATG
AAACAGTATTTAGAACTGATGCAAAAAGTGCTCGACGAAGGCACACAGA
AAAACGACCGTACCGGAACCGGAACGCTTTCCATTTTTGGTCATCAGAT
GCGTTTTAACCTGCAAGATGGATTCCCGCTGGTGACAACTAAACGTTGC
CACCTGCGTTCCATCATCCATGAACTGCTGTGGTTTCTGCAGGGCGACA
CTAACATTGCTTATCTACACGAAAACAATGTCACCATCTGGGACGAATG
GGCCGATGAAAACGGCGACCTCGGGCAGTGTATGGTAAACAGTGGCGC
GCCTGGCCAACGCCAGATGGTCGTCATATTGACCAGATCACTACGGTAC
TGAACCAGCTGAAAACGACCCGGATTCGCGCCGCATTATTGTTTCAGC
GTGGAACGTAGGCGAACTGGATAAAATGGCGCTGGCACCGTGCCATGCA

TTCTTCCAGTTCTATGTGGCAGACGGCAAACTCTCTTGCCAGCTTTATC
AGCGCTCCTGTGACGTCTTCCTCGGCCTGCCGTTCAACATTGCCAGCTA
CGCGTTATTGGTGCATATGATGGCGCAGCAGTGCGATCTGGAAGTGGGT
GATTTTGTCTGGACCGGTGGCGACACGCATCTGTACAGCAACCATATGG
ATCAAACTCATCTGCAATTAAGCCGCGAACCGCGTCCGCTGCCGAAGTT
GATTATCAAACGTAAACCCGAATCCATCTTCGACTACCGTTTCGAAGAC
TTTGAGATTGAAGGCTACGATCCGCATCCGGGCATTAAAGCGCCGGTGG
CTATCTAATTACGAAACATCCTGCCAGAGCCGACGCCAGTGTGCGTCGG
TTTTTTTACCCTCCGTTAAATTCTTCGAGACGCCTTCCCGAAGGCGCCA
TTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGAT
TAAGTTGGGTAACGCCAGGGTTTTCCCAGTCACGACGTTGTAAAACGAC
GGCCAGTGCCAAGCTTTCTTTAATGAAGCAGGGCATCAGGACGGTATCT
TTGTGGAGAAAGCAGAGTAATCTTATTCAGCCTGACTGGTGGGAAACCA
CCAGTCAGAATGTGTTAGCGCATGTTGACAAAAATACCATTAGTCACAT
TATCCGTCAGTCGGACGACATGGTAGATAACCTGTTTATTATGCGTTTT
GATCTTACGTTTAATATTACCTTTATGCGATGAAACGGTCTTGGCTTTG
ATATTCATTTGGTCAGAGATTTGAATGGTTCCCTGACCTGCCATCCACA
TTCGCAACATACTCGATTCGGTTCGGCTCAATGATAACGTCGGCATATT
TAAAAACGAGGTTATCGTTGTCTCTTTTTTCAGAATATCGCCAAGGATA
TCGTCGAGAGATTCCGGTTTAATCGATTTAGAACTGATCAATAAATTTT
TTCTGACCAATAGATATTCATCAAAATGAACATTGGCAATTGCCATAAA
AACGATAAATAACGTATTGGGATGTTGATTAATGATGAGCTTGATACGC
TGACTGTTAGAAGCATCGTGGATGAAACAGTCCTCATTAATAAACACCA
CTGAAGGGCGCTGTGAATCACAAGCTATGGCAAGGTCATCAACGGTTTC
AATGTCGTTGATTTCTCTTTTTTTAACCCCTCTACTCAACAGATACCCG
GTTAAACCTAGTCGGGTGTAACTACATAAATCCATAATAATCGTTGACA
TGGCATACCCTCACTCAATGCGTAACGATAATTCCCCTTACCTGAATAT
TTCATCATGACTAAACGGAACAACATGGGTCACCTAATGCGCCACTCTC
GCGATTTTCAGGCGGACTTACTATCCCGTAAAGTGTTGTATAATTTGC
CTGGAATTGTCTTAAAGTAAAGTAAATGTTGCGATATGTGAGTGAGCTT
AAAACAAATATTTCGCTGCAGGAGTATCCTGGAAGATGTTCGTAGAAGC
TTACTGCTCACAAGAAAAAGGCACGTCATCTGACGTGCCTTTTTATT
TGTACTACCCTGTACGATTACTGCAGCTCGAGTTTAATTCAAATCTTCT
TCAGAAATCAATTTTTGTTCAGCGTTATACTTTTGGGATTTTACCTCAA
AATGGGATTCTATTTTCACCCACTCCTTACAAAGGATATTCTCATGCCC
AAAAAGCCAGTGTTTGGGGCCAATAATGATTTTTTCTGGATTTTCTATC
AAATAGGCCGCCCACCAGCTATAAGTGCTATTAGCGATAATGCCATGCT
GACAAGATTGCATGAGCAGCATGTCCCAATACGCCTCTTCTTCTTTATC
CCTAGTGGTCATGTCCATAAAAGGGTAGCCAAGATCAAGATTTTGCGTG
AATTCTAAGTCTTCGCAAAACACAAAAAGCTCCATGTTTGGCACGCGCT

-continued

TTGCCATATACTCAAGCGCCTTTTTTTGATAGTCAATACCAAGCTGACA

GCCAATCCCCACATAATCCCCTCTTCTTATATGCACAAACACGCTGTTT

TTAGCGGCTAAAATCAAAGAAAGCTTGCACTGATATTCTTCCTCTTTTT

TATTATTATTCTTATTATTTTCGGTGGTGGTGGTAGAGTGAAGGTTTG

CTTGATTAAAGGGGATATAGCATCAAAGTATCGTGGATCTTGGAAATAG

CCAAAAAAATAAGTCAAGCGGCTTGGCTTTAGCAATTTAGGCTCGTATT

CAAAAACGATTTCTTGACTCACCCTATCAAATCCCATGCATTTGAGCGC

GTCTCTTACTAGCTTGGGGAGGTGTTGCATTTTAGCTATAGCGATTTCT

TTCGCGCTCGCATAGGGCAAATCAATAGGGAAAAGTTCTAATTGCATTT

TCCTATCGCTCCAATCAAAAGAAGTGATATCTAACAGCACAGGCGTATT

AGAGTGTTTTTGCAAACTTTTAGCGAAAGCGTATTGAAACATTTGATTC

CCAAGCCCTCCGCAAATTTGCACCACCTTAAAAGCCATATGTATATCTC

CTTCTTGAATTCTAAAAATTGATTGAATGTATGCAAATAAATGCATACA

CCATAGGTGTGGTTTAATTTGATGCCCTTTTTCAGGGCTGGAATGTGTA

AGAGCGGGGTTATTTATGCTGTTGTTTTTTGTTACTCGGGAAGGGCTT

TACCTCTTCCGCATAAACGCTTCCATCAGCGTTTATAGTTAAAAAAATC

TTTCGGAACTGGTTTTGCGCTTACCCCAACCAACAGGGGATTTGCTGCT

TTCCATTGAGCCTGTTTCTCTGCGCGACGTTCGCGGCGGCGTGTTTGTG

CATCCATCTGGATTCTCCTGTCAGTTAGCTTTGGTGGTGTGTGGCAGTT

GTAGTCCTGAACGAAAACCCCCGCGATTGGCACATTGGCAGCTAATCC

GGAATCGCACTTACGGCCAATGCTTCGTTTCGTATCACACACCCCAAAG

CCTTCTGCTTTGAATGCTGCCCTTCTTCAGGGCTTAATTTTTAAGAGCG

TCACCTTCATGGTGGTCAGTGCGTCCTGCTGATGTGCTCAGTATCACCG

CCAGTGGTATTTATGTCAACACCGCCAGAGATAATTTATCACCGCAGAT

GGTTATCTGTATGTTTTTTATATGAATTTATTTTTTGCAGGGGGGCATT

GTTTGGTAGGTGAGAGATCAATTCTGCATTAATGAATCGGCCAACGCGC

GGGGAGAGGCGGTTTGCGTATTGGGCGCTCTTCCGCTTCCTCGCTCACT

GACTCGCTGCGCTCGGTCGTTCGGCTGCGGCGAGCGGTATCAGCTCACT

CAAAGGCGGTAATACGGTTATCCACAGAATCAGGGGATAACGCAGGAAA

GAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACA

AAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCG

TGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGAC

ACGACTTATCGCCACTGGCAGCAGCCACTGGTAACAGGATTAGCAGAGC

GAGGTATGTAGGCGGTGCTACAGAGTTCTTGAAGTGGTGGCCTAACTAC

GGCTACACTAGAAGGACAGTATTTGGTATCTGCGCTCTGCTGAAGCCAG

TTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGA

AAAAAAGGATCTCAAGAAGATCCTTTGATCTTTTCTACGGGGTCTGACG

CTCAGTGGAACGAAAACTCACGTTAAGGGATTTTGGTCATGAGATTATC

AAAAAGGATCTTCACCTAGATCCTTTTAAATTAAAAATGAAGTTTTAAA

TCAATCTAAAGTATATATGAGTAAACTTGGTCTGACAGTTACCAATGCT

TAATCAGTGAGGCACCTATCTCAGCGATCTGTCTATTTCGTTCATCCAT

AGTTGCCTGACTCCCCGTCGTGTAGATAACTACGATACGGGAGGGCTTA

CCATCTGGCCCCAGTGCTGCAATGATACCGCGAGACCCACGCTCACCGG

CTCCAGATTTATCAGCAATAAACCAGCCAGCCGGAAGGGCCGAGCGCAG

AAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGC

TTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCA

GAAGTAAGTTGGCCGCAGTGTTATCACTCATGGTTATGGCAGCACTGCA

TAATTCTCTTACTGTCATGCCATCCGTAAGATGCTTTTCTGTGACTGGT

GAGTACTCAACCAAGTCATTCTGAGAATAGTGTATGCGGCGACCGAGTT

GCTCTTGCCCGGCGTCAATACGGGATAATACCGCGCCACATAGCAGAAC

TTTAAAAGTGCTCATCATTGGAAAACGTTCTTCGGGGCGAAAACTCTCA

AGGATCTTACCGCTGTTGAGATCCAGTTCGATGTAACCCACTCGTGCAC

CCAACTGATCTTCAGCATCTTTTACTTTCACCAGCGTTTCTGGGTGAGC

AAAAACAGGAAGGCAAAATGCCGCAAAAAAGGGAATAAGGGCGACACGG

AAATGTTGAATACTCATACTCTTCCTTTTTCAATATTATTGAAGCATTT

ATCAGGGTTATTGTCTCATGAGCGGATACATATTTGAATGTATTTAGAA

AAATAAACAAATAGGGGTTCCGCGCACATTTCCCCGAAAAGTGCCACCT

GACGTCTAAGAAACCATTATTATCATGACATTAACCTATAAAAATAGGC

GTATCACGAGGCCCTTTCGTC

The sequence of pG180 is set forth below (SEQ ID NO: 6):

TCGCGCGTTTCGGTGATGACGGTGAAAACCTCTGACACATGCAGCTCCC

GGAGACGGTCACAGCTTGTCTGTAAGCGGATGCCGGGAGCAGACAAGCC

CGTCAGGGCGCGTCAGCGGGTGTTGGCGGGTGTCGGGGCTGGCTTAACT

ATGCGGCATCAGAGCAGATTGTACTGAGAGTGCACCATATATGCGGTGT

GAAATACCGCACAGATGCGTAAGGAGAAAATACCGCATCAGGCGCCTCC

TCAACCTGTATATTCGTAAACCACGCCCAATGGGAGCTGTCTCAGGTTT

GTTCCTGATTGGTTACGGCGCGTTTCGCATCATTGTTGAGTTTTTCCGC

CAGCCCGACGCGCAGTTTACCGGTGCCTGGGTGCAGTACATCAGCATGG

GGCAAATTCTTTCCATCCCGATGATTGTCGCGGGTGTGATCATGATGGT

CTGGGCATATCGTCGCAGCCCACAGCAACACGTTTCCTGAGGAACCATG

-continued

```
AAACAGTATTTAGAACTGATGCAAAAAGTGCTCGACGAAGGCACACAGA
AAAACGACCGTACCGGAACCGGAACGCTTTCCATTTTTGGTCATCAGAT
GCGTTTTAACCTGCAAGATGGATTCCCGCTGGTGACAACTAAACGTTGC
CACCTGCGTTCCATCATCCATGAACTGCTGTGGTTTCTGCAGGGCGACA
CTAACATTGCTTATCTACACGAAAACAATGTCACCATCTGGGACGAATG
GGCCGATGAAAACGGCGACCTCGGGCCAGTGTATGGTAAACAGTGGCGC
GCCTGGCCAACGCCAGATGGTCGTCATATTGACCAGATCACTACGGTAC
TGAACCAGCTGAAAAACGACCCGGATTCGCGCCGCATTATTGTTTCAGC
GTGGAACGTAGGCGAACTGGATAAAATGGCGCTGGCACCGTGCCATGCA
TTCTTCCAGTTCTATGTGGCAGACGGCAAACTCTCTTGCCAGCTTTATC
AGCGCTCCTGTGACGTCTTCCTCGGCCTGCCGTTCAACATTGCCAGCTA
CGCGTTATTGGTGCATATGATGGCGCAGCAGTGCGATCTGGAAGTGGGT
GATTTTGTCTGGACCGGTGGCGACACGCATCTGTACAGCAACCATATGG
ATCAAACTCATCTGCAATTAAGCCGCGAACCGCGTCCGCTGCCGAAGTT
GATTATCAAACGTAAACCCGAATCCATCTTCGACTACCGTTTCGAAGAC
TTTGAGATTGAAGGCTACGATCCGCATCCGGGCATTAAAGCGCCGGTGG
CTATCTAATTACGAAACATCCTGCCAGAGCCGACGCCAGTGTGCGTCGG
TTTTTTTACCCTCCGTTAAATTCTTCGAGACGCCTTCCCGAAGGCGCCA
TTCGCCATTCAGGCTGCGCAACTGTTGGGAAGGGCGATCGGTGCGGGCC
TCTTCGCTATTACGCCAGCTGGCGAAAGGGGATGTGCTGCAAGGCGAT
TAAGTTGGGTAACGCCAGGGTTTTCCCAGTCACGACGTTGTAAAACGAC
GGCCAGTGCCAAGCTTTCTTTAATGAAGCAGGGCATCAGGACGGTATCT
TTGTGGAGAAAGCAGAGTAATCTTATTCAGCCTGACTGGTGGGAAACCA
CCAGTCAGAATGTGTTAGCGCATGTTGACAAAAATACCATTAGTCACAT
TATCCGTCAGTCGGACGACATGGTAGATAACCTGTTTATTATGCGTTTT
GATCTTACGTTTAATATTACCTTTATGCGATGAAACGGTCTTGGCTTTG
ATATTCATTTGGTCAGAGATTTGAATGGTTCCCTGACCTGCCATCCACA
TTCGCAACATACTCGATTCGGTTCGGCTCAATGATAACGTCGGCATATT
TAAAAACGAGGTTATCGTTGTCTCTTTTTTCAGAATATCGCCAAGGATA
TCGTCGAGAGATTCCGGTTTAATCGATTTAGAACTGATCAATAAATTTT
TTCTGACCAATAGATATTCATCAAAATGAACATTGGCAATTGCCATAAA
AACGATAAATAACGTATTGGGATGTTGATTAATGATGAGCTTGATACGC
TGACTGTTAGAAGCATCGTGGATGAAACAGTCCTCATTAATAAACACCA
CTGAAGGGCGCTGTGAATCACAAGCTATGGCAAGGTCATCAACGGTTTC
AATGTCGTTGATTTCTCTTTTTTTAACCCCTCTACTCAACAGATACCCG
GTTAAACCTAGTCGGGTGTAACTACATAAATCCATAATAATCGTTGACA
TGGCATACCCTCACTCAATGCGTAACGATAATTCCCCTTACCTGAATAT
TTCATCATGACTAAACGGAACAACATGGGTCACCTAATGCGCCACTCTC
GCGATTTTCAGGCGGACTTACTATCCCGTAAAGTGTTGTATAATTTGC
CTGGAATTGTCTTAAAGTAAAGTAAATGTTGCGATATGTGAGTGAGCTT
AAAACAAATATTTCGCTGCAGGAGTATCCTGGAAGATGTTCGTAGAAGC
```

-continued

```
TTACTGCTCACAAGAAAAAAGGCACGTCATCTGACGTGCCTTTTTTATT
TGTACTACCCTGTACGATTACTGCAGCTCGAGTTTAATTCAAATCTTCT
TCAGAAATCAATTTTTGTTCTCTTACATTCAATTTAAACCAAGATTCTG
GTACAGAATCCTTATTTATAAATTACCTGGAGCAATCACCAGCTTATC
ATCATATTTCGAAAGCCATGCTCCCCACCAGTAAAAAGAGCTATTCGAT
ATTATATAATTACGAAAATGCATCATTAGAAACATATCATCTATAGTAC
CACTATCATCCTCCTTTTTACTTATCAAACGAACAGGATATTTTCCCGC
TAGATGTTTTTCAACCCATTCTAAATCTTGTGAAAAACAAAAGAAAACA
GGAGAAGTAACTTTTGATGCCATAATATCCATAGCACATTTATAGTAAT
CATCTTCTAACACTCCACCAGGAGCTACATCACTTTCCTGATACCGTCT
AACCCCAATCATTATGGCATTCTTATCTAGCAATTTTATTTCTTCCAAT
TCCAAATACGATGTGTATTCTAATTTTTTTTGTATTACAAAGTCCTCTT
TTATCTCTTGTTTATAATCAAGAAATATTTTTCTGACTGCCAATATCC
TTCCAGAAAAGCATTTGTAATCTTAGAACTAATTAACCTTGATTCAAAG
TGGGGAGGGCGCTCTTCGCAAATATAACGATATGATGGATGAAGTATAT
GACAACCTAAATTACGACTTAGCCTTCTATAATAATTCCCATATGAAAA
ATCAAATGTTAATTTTTATTTTCAGGCAAGTCTAATGCAAAATATGAT
AATAAAAGTTTCCTTTTATAAACTTCATCATTTGCAAAATCAGTAGTCA
AATTAAAAGCGAATGGTACATTGTTTCTTAATGCCATGGCCTTCACCAT
AGCGTAAATAAACATTTGATTCCCCAATCCTCCTCGCAAAGATGATACA
ATCATATGTATATCTCCTTCTTGTCTAGAATTCTAAAAATTGATTGAAT
GTATGCAAATAAATGCATACACCATAGGTGTGGTTTAATTTGATGCCCT
TTTTCAGGGCTGGAATGTGTAAGAGCGGGGTTATTTATGCTGTTGTTTT
TTTGTTACTCGGGAAGGGCTTTACCTCTTCCGCATAAACGCTTCCATCA
GCGTTTATAGTTAAAAAAATCTTTCGGAACTGGTTTTGCGCTTACCCCA
ACCAACAGGGGATTTGCTGCTTTCCATTGAGCCTGTTTCTCTGCGCGAC
GTTCGCGGCGGCGTGTTTGTGCATCCATCTGGATTCTCCTGTCAGTTAG
CTTTGGTGGTGTGTGGCAGTTGTAGTCCTGAACGAAAACCCCCCGCGAT
TGGCACATTGGCAGCTAATCCGGAATCGCACTTACGGCCAATGCTTCGT
TTCGTATCACACACCCCAAAGCCTTCTGCTTTGAATGCTGCCCTTCTTC
AGGGCTTAATTTTTAAGAGCGTCACCTTCATGGTGGTCAGTGCGTCCTG
CTGATGTGCTCAGTATCACCGCCAGTGGTATTTATGTCAACACCGCCAG
AGATAATTTATCACCGCAGATGGTTATCTGTATGTTTTTATATGAATT
TATTTTTTGCAGGGGGCATTGTTTGGTAGGTGAGAGATCAATTCTGCA
TTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGC
GGCGAGCGGTATCAGCTCACTCAAAGGCGGTAATACGGTTATCCACAGA
ATCAGGGGATAACGCAGGAAAGAACATGTGAGCAAAAGGCCAGCAAAAG
GCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCG
```

AAACCCGACAGGACTATAAAGATACCAGGCGTTTCCCCCTGGAAGCTCC

CTCGTGCGCTCTCCTGTTCCGACCCTGCCGCTTACCGGATACCTGTCCG

CCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTC

TTGAGTCCAACCCGGTAAGACACGACTTATCGCCACTGGCAGCAGCCAC

TGGTAACAGGATTAGCAGAGCGAGGTATGTAGGCGGTGCTACAGAGTTC

TTGAAGTGGTGGCCTAACTACGGCTACACTAGAAGGACAGTATTTGGTA

TCTGCGCTCTGCTGAAGCCAGTTACCTTCGGAAAAGAGTTGGTAGCTC

TTGATCCGGCAAACAAACCACCGCTGGTAGCGGTGGTTTTTTTGTTTGC

AAGCAGCAGATTACGCGCAGAAAAAAAGGATCTCAAGAAGATCCTTTGA

TCTTTTCTACGGGGTCTGACGCTCAGTGGAACGAAAACTCACGTTAAGG

GATTTTGGTCATGAGATTATCAAAAAGGATCTTCACCTAGATCCTTTTA

AATTAAAAATGAAGTTTTAAATCAATCTAAAGTATATATGAGTAAACTT

GGTCTGACAGTTACCAATGCTTAATCAGTGAGGCACCTATCTCAGCGAT

CTGTCTATTTCGTTCATCCATAGTTGCCTGACTCCCCGTCGTGTAGATA

ACTACGATACGGGAGGGCTTACCATCTGGCCCCAGTGCTGCAATGATAC

CGCGAGACCCACGCTCACCGGCTCCAGATTTATCAGCAATAAACCAGCC

AGCCGGAAGGGCCGAGCGCAGAAGTGGTCCTGCAACTTTATCCGCCTCC

ATCCAGTCTATTAATTGTTGCCGGGAAGCTAGAGTAAGTAGTTCGCCAG

TTAATAGTTTGCGCAACGTTGTTGCCATTGCTACAGGCATCGTGGTGTC

ACGCTCGTCGTTTGGTATGGCTTCATTCAGCTCCGGTTCCCAACGATCA

AGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACT

CATGGTTATGGCAGCACTGCATAATTCTCTTACTGTCATGCCATCCGTA

AGATGCTTTTCTGTGACTGGTGAGTACTCAACCAAGTCATTCTGAGAAT

AGTGTATGCGGCGACCGAGTTGCTCTTGCCCGGCGTCAATACGGGATAA

TACCGCGCCACATAGCAGAACTTTAAAAGTGCTCATCATTGGAAAACGT

TCTTCGGGGCGAAAACTCTCAAGGATCTTACCGCTGTTGAGATCCAGTT

CGATGTAACCCACTCGTGCACCCAACTGATCTTCAGCATCTTTTACTTT

CACCAGCGTTTCTGGGTGAGCAAAAACAGGAAGGCAAAATGCCGCAAAA

AAGGGAATAAGGGCGACACGGAAATGTTGAATACTCATACTCTTCCTTT

TTCAATATTATTGAAGCATTTATCAGGGTTATTGTCTCATGAGCGGATA

CATATTTGAATGTATTTAGAAAAATAAACAAATAGGGGTTCCGCGCACA

TTTCCCCGAAAAGTGCCACCTGACGTCTAAGAAACCATTATTATCATGA

CATTAACCTATAAAAATAGGCGTATCACGAGGCCCTTTCGTC

The sequence of W3110 deltalon::Kan::lacZwithRBS *Escherichia coli* str. K-12 substr. W3110 is set forth below (SEQ ID NO: 7):

GTCCATGGAAGACGTCGAAAAAGTGGTTATCGACGAGTCGGTAATTGAT

GGTCAAAGCAAACCGTTGCTGATTTATGGCAAGCCGGAAGCGCAACAGG

CATCTGGTGAATAATTAACCATTCCCATACAATTAGTTAACCAAAAAGG

GGGGATTTTATCTCCCCTTTAATTTTTCCTCTATTCTCGGCGTTGAATG

TGGGGGAAACATCCCCATATACTGACGTACATGTTAATAGATGGCGTGA

AGCACAGTCGTGTCATCTGATTACCTGGCGGAAATTAAACTAAGAGAGA

GCTCTATGATTCCGGGGATCCGTCGACCTGCAGTTCGAAGTTCCTATTC

TCTAGAAAGTATAGGAACTTCAGAGCGCTTTTGAAGCTCACGCTGCCGC

AAGCACTCAGGGCGCAAGGGCTGCTAAAGGAAGCGGAACACGTAGAAAG

CCAGTCCGCAGAAACGGTGCTGACCCCGGATGAATGTCAGCTACTGGGC

TATCTGGACAAGGGAAAACGCAAGCGCAAAGAGAAAGCAGGTAGCTTGC

AGTGGGCTTACATGGCGATAGCTAGACTGGGCGGTTTTATGGACAGCAA

GCGAACCGGAATTGCCAGCTGGGGCGCCCTCTGGTAAGGTTGGGAAGCC

CTGCAAAGTAAACTGGATGGCTTTCTTGCCGCCAAGGATCTGATGGCGC

AGGGGATCAAGATCTGATCAAGAGACAGGATGAGGATCGTTTCGCATGA

TTGAACAAGATGGATTGCACGCAGGTTCTCCGGCCGCTTGGGTGGAGAG

GCTATTCGGCTATGACTGGGCACAACAGACAATCGGCTGCTCTGATGCC

GCCGTGTTCCGGCTGTCAGCGCAGGGGCGCCCGGTTCTTTTTGTCAAGA

CCGACCTGTCCGGTGCCCTGAATGAACTGCAGGACGAGGCAGCGCGGCT

ATCGTGGCTGGCCACGACGGGCGTTCCTTGCGCAGCTGTGCTCGACGTT

GTCACTGAAGCGGGAAGGGACTGGCTGCTATTGGGCGAAGTGCCGGGGC

AGGATCTCCTGTCATCTCACCTTGCTCCTGCCGAGAAAGTATCCATCAT

GGCTGATGCAATGCGGCGGCTGCATACGCTTGATCCGGCTACCTGCCCA

TTCGACCACCAAGCGAAACATCGCATCGAGCGAGCACGTACTCGGATGG

AAGCCGGTCTTGTCGATCAGGATGATCTGGACGAAGAGCATCAGGGGCT

CGCGCCAGCCGAACTGTTCGCCAGGCTCAAGGCGCGCATGCCCGACGGC

GAGGATCTCGTCGTGACCCATGGCGATGCCTGCTTGCCGAATATCATGG

TGGAAAATGGCCGCTTTTCTGGATTCATCGACTGTGGCCGGCTGGGTGT

GGCGGACCGCTATCAGGACATAGCGTTGGCTACCCGTGATATTGCTGAA

GAGCTTGGCGGCGAATGGGCTGACCGCTTCCTCGTGCTTTACGGTATCG

CCGCTCCCGATTCGCAGCGCATCGCCTTCTATCGCCTTCTTGACGAGTT

CTTCTAATAAGGGGATCTTGAAGTTCCTATTCCGAAGTTCCTATTCTCT

AGAAAGTATAGGAACTTCGAAGCAGCTCCAGCCTACATAAAGCGGCCGC

TTATTTTTGACACCAGACCAACTGGTAATGGTAGCGACCGGCGCTCAGC

TGGAATTCCGCCGATACTGACGGGCTCCAGGAGTCGTCGCCACCAATCC

CCATATGGAAACCGTCGATATTCAGCCATGTGCCTTCTTCCGCGTGCAG

CAGATGGCGATGGCTGGTTTCCATCAGTTGCTGTTGACTGTAGCGGCTG

ATGTTGAACTGGAAGTCGCCGCGCCACTGGTGTGGGCCATAATTCAATT

CGCGCGTCCCGCAGCGCAGACCGTTTTCGCTCGGGAAGACGTACGGGGT

ATACATGTCTGACAATGGCAGATCCCAGCGGTCAAAACAGGCGGCAGTA

AGGCGGTCGGGATAGTTTTCTTGCGGCCCTAATCCGAGCCAGTTTACCC

GCTCTGCTACCTGCGCCAGCTGGCAGTTCAGGCCAATCCGCGCCGGATG

-continued
```
CGGTGTATCGCTCGCCACTTCAACATCAACGGTAATCGCCATTTGACCA
CTACCATCAATCCGGTAGGTTTTCCGGCTGATAAATAAGGTTTTCCCCT
GATGCTGCCACGCGTGAGCGGTCGTAATCAGCACCGCATCAGCAAGTGT
ATCTGCCGTGCACTGCAACAACGCTGCTTCGGCCTGGTAATGGCCCGCC
GCCTTCCAGCGTTCGACCCAGGCGTTAGGGTCAATGCGGGTCGCTTCAC
TTACGCCAATGTCGTTATCCAGCGGTGCACGGGTGAACTGATCGCGCAG
CGGCGTCAGCAGTTGTTTTTTATCGCCAATCCACATCTGTGAAAGAAAG
CCTGACTGGCGGTTAAATTGCCAACGCTTATTACCCAGCTCGATGCAAA
AATCCATTTCGCTGGTGGTCAGATGCGGGATGGCGTGGGACGCGGCGGG
GAGCGTCACACTGAGGTTTTCCGCCAGACGCCACTGCTGCCAGGCGCTG
ATGTGCCCGGCTTCTGACCATGCGGTCGCGTTCGGTTGCACTACGCGTA
CTGTGAGCCAGAGTTGCCCGGCGCTCTCCGGCTGCGGTAGTTCAGGCAG
TTCAATCAACTGTTTACCTTGTGGAGCGACATCCAGAGGCACTTCACCG
CTTGCCAGCGGCTTACCATCCAGCGCCACCATCCAGTGCAGGAGCTCGT
TATCGCTATGACGGAACAGGTATTCGCTGGTCACTTCGATGGTTTGCCC
GGATAAACGGAACTGGAAAAACTGCTGCTGGTGTTTTGCTTCCGTCAGC
GCTGGATGCGGCGTGCGGTCGGCAAAGACCAGACCGTTCATACAGAACT
GGCGATCGTTCGGCGTATCGCCAAAATCACCGCCGTAAGCCGACCACGG
GTTGCCGTTTTCATCATATTTAATCAGCGACTGATCCACCCAGTCCCAG
ACGAAGCCGCCCTGTAAACGGGGATACTGACGAAACGCCTGCCAGTATT
TAGCGAAACCGCCAAGACTGTTACCCATCGCGTGGGCGTATTCGCAAAG
GATCAGCGGGCGCGTCTCTCCAGGTAGCGAAAGCCATTTTTTGATGGAC
CATTTCGGCACAGCCGGGAAGGGCTGGTCTTCATCCACGCGCGCGTACA
TCGGGCAAATAATATCGGTGGCCGTGGTGTCGGCTCCGCCGCCTTCATA
CTGCACCGGGCGGGAAGGATCGACAGATTTGATCCAGCGATACAGCGCG
TCGTGATTAGCGCCGTGGCCTGATTCATTCCCCAGCGACCAGATGATCA
CACTCGGGTGATTACGATCGCGCTGCACCATTCGCGTTACGCGTTCGCT
CATCGCCGGTAGCCAGCGCGGATCATCGGTCAGACGATTCATTGGCACC
ATGCCGTGGGTTTCAATATTGGCTTCATCCACCACATACAGGCCGTAGC
GGTCGCACAGCGTGTACCACAGCGGATGGTTCGGATAATGCGAACAGCG
CACGGCGTTAAAGTTGTTCTGCTTCATCAGCAGGATATCCTGCACCATC
GTCTGCTCATCCATGACCTGACCATGCAGAGGATGATGCTCGTGACGGT
TAACGCCTCGAATCAGCAACGGCTTGCCGTTCAGCAGCAGCAGACCATT
TTCAATCCGCACCTCGCGGAAACCGACATCGCAGGCTTCTGCTTCAATC
AGCGTGCCGTCGGCGGTGTGCAGTTCAACCACCGCACGATAGAGATTCG
GGATTTCGGCGCTCCACAGTTTCGGGTTTTCGACGTTCAGACGTAGTGT
GACGCGATCGGCATAACCACCACGCTCATCGATAATTTCACCGCCGAAA
GGCGCGGTGCCGCTGGCGACCTGCGTTTCACCCTGCCATAAAGAAACTG
TTACCCGTAGGTAGTCACGCAACTCGCCGCACATCTGAACTTCAGCCTC
CAGTACAGCGCGGCTGAAATCATCATTAAAGCGAGTGGCAACATGGAAA
TCGCTGATTTGTGTAGTCGGTTTATGCAGCAACGAGACGTCACGGAAAA
TGCCGCTCATCCGCCACATATCCTGATCTTCCAGATAACTGCCGTCACT
CCAGCGCAGCACCATCACCGCGAGGCGGTTTTCTCCGGCGCGTAAAAAT
GCGCTCAGGTCAAATTCAGACGGCAAACGACTGTCCTGGCCGTAACCGA
CCCAGCGCCCGTTGCACCACAGATGAAACGCCGAGTTAACGCCATCAAA
AATAATTCGCGTCTGGCCTTCCTGTAGCCAGCTTTCATCAACATTAAAT
GTGAGCGAGTAACAACCCGTCGGATTCTCCGTGGGAACAAACGGCGGAT
TGACCGTAATGGGATAGGTCACGTTGGTGTAGATGGGCGCATCGTAACC
GTGCATCTGCCAGTTTGAGGGGACGACGACAGTATCGGCCTCAGGAAGA
TCGCACTCCAGCCAGCTTTCCGGCACCGCTTCTGGTGCCGGAAACCAGG
CAAAGCGCCATTCGCCATTCAGGCTGCGCAACTGTTGGGAAGGGCGATC
GGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTT
GTAAAACGACGGCCAGTGAATCCGTAATCATGGTCATAGTAGGTTTCCT
CAGGTTGTGACTGCAAAATAGTGACCTCGCGCAAAATGCACTAATAAAA
ACAGGGCTGGCAGGCTAATTCGGGCTTGCCAGCCTTTTTTTGTCTCGCT
AAGTTAGATGGCGGATCGGGCTTGCCCTTATTAAGGGGTGTTGTAAGGG
GATGGCTGGCCTGATATAACTGCTGCGCGTTCGTACCTTGAAGGATTCA
AGTGCGATATAAATTATAAAGAGGAAGAGAAGAGTGAATAAATCTCAAT
TGATCGACAAGATTGCTGCAGGGGCTGATATCTCTAAAGCTGCGGCTGG
CCGTGCGTTAGATGCTATTATTGCTTCCGTAACTGAATCTCTGAAAGAA
GG
```
The sequence of pG186 is set forth below (SEQ ID NO: 8):
```
TCGCGCGTTTCGGTGATGACGGTGAAAACCTCTGACACATGCAGCTCCC
GGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACT
ATGCGGCATCAGAGCAGATTGTACTGAGAGTGCACCATATATGCGGTGT
GAAATACCGCACAGATGCGTAAGGAGAAAATACCGCATCAGGCGCCTCC
TCAACCTGTATATTCGTAAACCACGCCCAATGGGAGCTGTCTCAGGTTT
GTTCCTGATTGGTTACGGCGCGTTTCGCATCATTGTTGAGTTTTTCCGC
CAGCCCGACGCGCAGTTTACCGGTGCCTGGGTGCAGTACATCAGCATGG
GGCAAATTCTTTCCATCCCGATGATTGTCGCGGGTGTGATCATGATGGT
CTGGGCATATCGTCGCAGCCCACAGCAACACGTTTCCTGAGGAACCATG
AAACAGTATTTAGAACTGATGCAAAAAGTGCTCGACGAAGGCACACAGA
AAAACGACCGTACCGGAACCGGAACGCTTTCCATTTTTGGTCATCGATT
GCGTTTTAACCTGCAAGATGGATTCCCGCTGGTGACAACTAAACGTTGC
CACCTGCGTTCCATCATCCATGAACTGCTGTGGTTTCTGCAGGGCGACA
CTAACATTGCTTATCTACACGAAAACAATGTCACCATCTGGGACGAATG
GGCCGATGAAAACGGCGACCTCGGGCCAGTGTATGGTAAACAGTGGCGC
GCCTGGCCAACGCCAGATGGTCGTCATATTGACCAGATCACTACGGTAC
```

-continued

```
TGAACCAGCTGAAAAACGACCCGGATTCGCGCCGCATTATTGTTTCAGC
GTGGAACGTAGGCGAACTGGATAAAATGGCGCTGGCACCGTGCCATGCA
TTCTTCCAGTTCTATGTGGCAGACGGCAAACTCTCTTGCCAGCTTTATC
AGCGCTCCTGTGACGTCTTCCTCGGCCTGCCGTTCAACATTGCCAGCTA
CGCGTTATTGGTGCATATGATGGCGCAGCAGTGCGATCTGGAAGTGGGT
GATTTTGTCTGGACCGGTGGCGACACGCATCGTACAGCAACCATATGG
ATCAAACTCATCTGCAATTAAGCCGCGAACCGCGTCCGCTGCCGAAGTT
GATTATCAAACGTAAACCCGAATCCATCTTCGACTACCGTTTCGAAGAC
TTTGAGATTGAAGGCTACGATCCGCATCCGGGCATTAAAGCGCCGGTGG
CTATCTAATTACGAAACATCCTGCCAGAGCCGACGCCAGTGTGCGTCGG
TTTTTTTACCCTCCGTTAAATTCTTCGAGACGCCTTCCCGAAGGCGCCA
TTCGCCATTCAGGCTGCGCAACTGTTGGGAAGGGCGATCGGTGCGGGCC
TCTTCGCTATTACGCCAGCTGGCGAAAGGGGATGTGCTGCAAGGCGAT
TAAGTTGGGTAACGCCAGGGTTTTCCCAGTCACGACGTTGTAAAACGAC
GGCCAGTGCCAAGCTTTCTTTAATGAAGCAGGGCATCAGGACGGTATCT
TTGTGGAGAAAGCAGAGTAATCTTATTCAGCCTGACTGGTGGGAAACCA
CCAGTCAGAATGTGTTAGCGCATGTTGACAAAAATACCATTAGTCACAT
TATCCGTCAGTCGGACGACATGGTAGATAACCTGTTTATTATGCGTTTT
GATCTTACGTTTAATATTACCTTTATGCGATGAAACGGTCTTGGCTTTG
ATATTCATTTGGTCAGAGATTTGAATGGTTCCCTGACCTGCCATCCACA
TTCGCAACATACTCGATTCGGTTCGGCTCAATGATAACGTCGGCATATT
TAAAAACGAGGTTATCGTTGTCTCTTTTTTCAGAATATCGCCAAGGATA
TCGTCGAGAGATTCCGGTTTAATCGATTTAGAACTGATCAATAAATTTT
TTCTGACCAATAGATATTCATCAAAATGAACATTGGCAATTGCCATAAA
AACGATAAATAACGTATTGGGATGTTGATTAATGATGAGCTTGATACGC
TGACTGTTAGAAGCATCGTGGATGAAACAGTCCTCATTAATAAACACCA
CTGAAGGGCGCTGTGAATCACAAGCTATGGCAAGGTCATCAACGGTTTC
AATGTCGTTGATTTCTCTTTTTTTAACCCCTCTACTCAACAGATACCCG
GTTAAACCTAGTCGGGTGTAACTACATAAATCCATAATAATCGTTGACA
TGGCATACCCTCACTCAATGCGTAACGATAATTCCCCTTACCTGAATAT
TTCATCATGACTAAACGGAACAACATGGGTCACCTAATGCGCCACTCTC
GCGATTTTTCAGGCGGACTTACTATCCCGTAAAGTGTTGTATAATTTGC
CTGGAATTGTCTTAAAGTAAAGTAAATGTTGCGATATGTGAGTGAGCTT
AAAACAAATATTTCGCTGCAGGAGTATCCTGGAAGATGTTCGTAGAAGC
TTACTGCTCACAAGAAAAAGGCACGTCATCTGACGTGCCTTTTTTATT
TGTACTACCCTGTACGATTACTGCAGCTCGAGTTAGTCTTTATCTGCCG
GACTTAAGGTCACTGAAGAGAGATAATTCAGCAGGGCGATATCGTTCTC
GACACCCAGCTTCATCATCGCAGATTTCTTCTGGCTACTGATGGTTTTA
ATACTGCGGTTCAGCTTTTTAGCGATCTCGGTCACCAGGAAGCCTTCCG
CAAACAGGCGCAGAACTTCACTCTCTTTTGGCGAGAGACGCTTGTCACC
```

-continued

```
GTAACCACCAGCACTGATTTTTTCCAACAGGCGAGAAACGCTTTCCGGG
GTAAATTTCTTCCCTTTCTGCAGCGCGGCGAGAGCTTTCGGCAGATCGG
TCGGTGCACCTTGTTTCAGCACGATCCCTTCGATATCCAGATCCAATAC
CGCACTAAGAATCGCCGGGTTGTTGTTCATAGTCAGAACAATGATCGAC
AGGCTTGGGAAATGGCGCTTGATGTACTTGATTAAGGTAATGCCATCGC
CGTACTTATCGCCAGGCATGGAGAGATCGGTAATCAACACATGCGCATC
CAGTTTCGGCAGGTTGTTGATCAGTGCTGTAGAGTCTTCAAATTCGCCG
ACAACATTCACCCACTCAATTTGCTCAAGTGATTTGCGAATACCGAACA
AGACTATCGGATGGTCATCGGCAATAATTACGTTCATATTGTTCATTGT
ATATCTCCTTCTTCTCGAGTTTAATTCAAATCTTCTTCAGAAATCAATT
TTTGTTCAGCGTTATACTTTTGGGATTTTACCTCAAAATGGGATTCTAT
TTTCACCCACTCCTTACAAAGGATATTCTCATGCCCAAAAAGCCAGTGT
TTGGGGCCAATAATGATTTTTTCTGGATTTTCTATCAAATAGGCCGCCC
ACCAGCTATAAGTGCTATTAGCGATAATGCCATGCTGACAAGATTGCAT
GAGCAGCATGTCCCAATACGCCTCTTCTTCTTTATCCCTAGTGGTCATG
TCCATAAAAGGGTAGCCAAGATCAAGATTTTGCGTGAATTCTAAGTCTT
CGCAAAACACAAAAAGCTCCATGTTTGGCACGCGCTTTGCCATATACTC
AAGCGCCTTTTTTGATAGTCAATACCAAGCTGACAGCCAATCCCCACA
TAATCCCCTCTTCTTATATGCACAAACACGCTGTTTTTAGCGGCTAAAA
TCAAAGAAAGCTTGCACTGATATTCTTCCTCTTTTTTATTATTATTCTT
ATTATTTTCGGGTGGTGGTGGTAGAGTGAAGGTTTGCTTGATTAAAGGG
GATATAGCATCAAAGTATCGTGGATCTTGGAAATAGCCAAAAAAATAAG
TCAAGCGGCTTGGCTTTAGCAATTTAGGCTCGTATTCAAAAACGATTTC
TTGACTCACCCTATCAAATCCCATGCATTTGAGCGCGTCTCTTACTAGC
TTGGGGAGGTGTTGCATTTTAGCTATAGCGATTTCTTTCGCGCTCGCAT
AGGGCAAATCAATAGGGAAAAGTTCTAATTGCATTTTCCTATCGCTCCA
ATCAAAAGAAGTGATATCTAACAGCACAGGCGTATTAGAGTGTTTTGC
AAACTTTTAGCGAAAGCGTATTGAAACATTTGATTCCCAAGCCCTCCGC
AAATTTGCACCACCTTAAAAGCCATATGTATATCTCCTTCTTGAATTCT
AAAAATTGATTGAATGTATGCAAATAAATGCATACACCATAGGTGTGGT
TTAATTTGATGCCCTTTTTCAGGGCTGGAATGTGTAAGAGCGGGGTTAT
TTATGCTGTTGTTTTTTGTTACTCGGGAAGGGCTTTACCTCTTCCGCA
TAAACGCTTCCATCAGCGTTTATAGTTAAAAAAATCTTTCGGAACTGGT
TTTGCGCTTACCCCAACCAACAGGGGATTTGCTGCTTTCCATTGAGCCT
GTTTCTCTGCGCGACGTTCGCGGCGGCGTGTTTGTGCATCCATCTGGAT
TCTCCTGTCAGTTAGCTTTGGTGGTGTGTGGCAGTTGTAGTCCTGAACG
AAAACCCCCGCGATTGGCACATTGGCAGCTAATCCGGAATCGCACTTA
CGGCCAATGCTTCGTTTCGTATCACACACCCCAAAGCTTCTGCTTTGA
ATGCTGCCCTTCTTCAGGGCTTAATTTTTAAGAGCGTCACCTTCATGGT
GGTCAGTGCGTCCTGCTGATGTGCTCAGTATCACCGCCAGTGGTATTTA
TGTCAACACCGCCAGAGATAATTTATCACCGCAGATGGTTATCTGTATG
```

TTTTTTATATGAATTTATTTTTTGCAGGGGGGCATTGTTTGGTAGGTGA

GAGATCAATTCTGCATTAATGAATCGGCCAACGCGCGGGGAGAGGCGGT

TTGCGTATTGGGCGCTCTTCCGCTTCCTCGCTCACTGACTCGCTGCGCT

CGGTCGTTCGGCTGCGGCGAGCGGTATCAGCTCACTCAAAGGCGGTAAT

ACGGTTATCCACAGAATCAGGGGATAACGCAGGAAAGAACATGTGAGCA

AAAGGCCAGCAAAAGGCCAGGAACCGTAAAAAGGCCGCGTTGCTGGCGT

TTTTCCATAGGCTCCGCCCCCCTGACGAGCATCACAAAAATCGACGCTC

AAGTCAGAGGTGGCGAAACCCGACAGGACTATAAAGATACCAGGCGTTT

CCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAG

CTGGGCTGTGTGCACGAACCCCCCGTTCAGCCCGACCGCTGCGCCTTAT

CCGGTAACTATCGTCTTGAGTCCAACCCGGTAAGACACGACTTATCGCC

ACTGGCAGCAGCCACTGGTAACAGGATTAGCAGAGCGAGGTATGTAGGC

GGTGCTACAGAGTTCTTGAAGTGGTGGCCTAACTACGGCTACACTAGAA

GGACAGTATTTGGTATCTGCGCTCTGCTGAAGCCAGTTACCTTCGGAAA

AAGAGTTGGTAGCTCTTGATCCGGCAAACAAACCACCGCTGGTAGCGGT

GGTTTTTTTGTTTGCAAGCAGCAGATTACGCGCAGAAAAAAAGGATCTC

AAGAAGATCCTTTGATCTTTTCTACGGGGTCTGACGCTCAGTGGAACGA

AAACTCACGTTAAGGGATTTTGGTCATGAGATTATCAAAAGGATCTTC

ACCTAGATCCTTTTAAATTAAAAATGAAGTTTTAAATCAATCTAAAGTA

TATATGAGTAAACTTGGTCTGACAGTTACCAATGCTTAATCAGTGAGGC

ACCTATCTCAGCGATCTGTCTATTTCGTTCATCCATAGTTGCCTGACTC

CCCGTCGTGTAGATAACTACGATACGGGAGGGCTTACCATCTGGCCCCA

GTGCTGCAATGATACCGCGAGACCCACGCTCACCGGCTCCAGATTTATC

AGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAG

TAAGTAGTTCGCCAGTTAATAGTTTGCGCAACGTTGTTGCCATTGCTAC

AGGCATCGTGGTGTCACGCTCGTCGTTTGGTATGGCTTCATTCAGCTCC

GGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGC

CGCAGTGTTATCACTCATGGTTATGGCAGCACTGCATAATTCTCTTACT

GTCATGCCATCCGTAAGATGCTTTTCTGTGACTGGTGAGTACTCAACCA

AGTCATTCTGAGAATAGTGTATGCGGCGACCGAGTTGCTCTTGCCCGGC

GTCAATACGGGATAATACCGCGCCACATAGCAGAACTTTAAAAGTGCTC

ATCATTGGAAAACGTTCTTCGGGGCGAAAACTCTCAAGGATCTTACCGC

TGTTGAGATCCAGTTCGATGTAACCCACTCGTGCACCCAACTGATCTTC

AGCATCTTTTACTTTCACCAGCGTTTCTGGGTGAGCAAAAACAGGAAGG

CAAAATGCCGCAAAAAAGGGAATAAGGGCGACACGGAAATGTTGAATAC

TCATACTCTTCCTTTTTCAATATTATTGAAGCATTTATCAGGGTTATTG

TCTCATGAGCGGATACATATTTGAATGTATTTAGAAAAATAAACAAATA

GGGGTTCCGCGCACATTTCCCCGAAAAGTGCCACCTGACGTCTAAGAAA

CCATTATTATCATGACATTAACCTATAAAAATAGGCGTATCACGAGGCC

CTTTCGTC

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing a fucosylated oligosaccharide in a bacterium, comprising providing an isolated *Escherichia coli* (*E. coli*) bacterium comprising:
   (i) an exogenous β-galactosidase having a detectable level of β-galactosidase activity that is reduced compared to that of a wild-type *E. coli* bacterium, wherein the level of β-galactosidase activity is between 0.05 and 200 units;
   (ii) an inactivating mutation in a colanic acid synthesis gene; and
   (iii) an exogenous fucosyltransferase gene,
   culturing said bacterium in the presence of lactose; and retrieving a fucosylated oligosaccharide from said bacterium or from a culture supernatant of said bacterium.

2. The method of claim 1, wherein said colanic acid synthesis gene comprises an *E. coli* wcaJ, wzxC, wcaD, wza, wzb, or wzc gene.

3. The method of claim 2, wherein said colanic acid synthesis gene comprises a wcaJ gene.

4. The method of claim 1, comprising an increased intracellular guanosine diphosphate (GDP)-fucose level, wherein the increased intracellular GDP-fucose level is at least 10% more than the level of GDP-fucose in a wild-type bacterium.

5. The method of claim 1, wherein said exogenous fucosyltransferase gene encodes an α(1,2) fucosyltransferase and/or an α(1,3) fucosyltransferase.

6. The method of claim 5, wherein said α(1,2) fucosyltransferase gene comprises a *Bacteroides fragilis* wcfW gene.

7. The method of claim 5, wherein said α(1,2) fucosyltransferase gene comprises a *Helicobacter pylori* 26695 futC gene.

8. The method of claim 1, wherein said α(1,3) fucosyltransferase gene comprises a *Helicobacter pylori* 26695 futA gene.

9. The method of claim 1, wherein said bacterium further comprises a functional lactose permease gene.

10. The method of claim 9, wherein said lactose permease gene is an endogenous lactose permease gene.

11. The method of claim 9, wherein said lactose permease gene comprises an *E. coli* lacY gene.

12. The method of claim 9, wherein said lactose permease gene is an exogenous lactose permease gene.

13. The method of claim 1, wherein said bacterium further comprises an exogenous *E. coli* rcsA or *E. coli* rcsB gene.

14. The method of claim 1, wherein said bacterium further comprises an inactivating mutation in a lacA gene.

15. The method of claim 1, wherein said bacterium further comprises an exogenous sialyltransferase gene.

16. The method of claim 15 wherein said exogenous sialyltransferase gene encodes an α(2,3) sialyltransferase.

17. The method of claim 1, wherein said bacterium further comprises a deficient sialic acid catabolic pathway comprising a null mutation in an endogenous N-acetylneuraminate lyase gene or a null mutation in an endogenous N-acetylmannosamine kinase gene.

18. The method of claim 1, wherein said bacterium further comprises an inactivating mutation in a lon gene.

19. The method of claim 1, wherein said bacterium further comprises an increased intracellular lactose level, wherein the increased intracellular lactose level is at least 10% more than the level in a wild-type bacterium.

20. The method of claim 1, wherein said bacterium further comprises an exogenous functional β-galactosidase gene that is inserted into an endogenous gene.

21. The method of claim 1, wherein the level of β-galactosidase activity is between 0.05 and 5 units.

22. The method of claim 1, wherein the level of β-galactosidase activity is between 0.05 and 4 units.

23. The method of claim 1, wherein the level of β-galactosidase activity is between 0.05 and 3 units.

24. The method of claim 1, wherein the level of β-galactosidase activity is between 0.05 and 2 units.

* * * * *

SEQUENCE LISTING

```
<160> NUMBER OF SEQ ID NOS: 15

<210> SEQ ID NO 1
<211> LENGTH: 6165
<212> TYPE: DNA
<213> ORGANISM: Artificial Sequence
<220> FEATURE:
<223> OTHER INFORMATION: Sequence of PG175.

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
```

-continued

```
ttggcgggtg tcggggctgg cttaactatg cggcatcaga gcagattgta ctgagagtgc      180
accatatatg cggtgtgaaa taccgcacag atgcgtaagg agaaaatacc gcatcaggcg      240
cctcctcaac ctgtatattc gtaaaccacg cccaatggga gctgtctcag gtttgttcct      300
gattggttac ggcgcgtttc gcatcattgt tgagttttc cgccagcccg acgcgcagtt       360
taccggtgcc tgggtgcagt acatcagcat ggggcaaatt ctttccatcc cgatgattgt     420
cgcgggtgtg atcatgatgg tctgggcata tcgtcgcagc ccacagcaac acgtttcctg      480
aggaaccatg aaacagtatt tagaactgat gcaaaaagtg ctcgacgaag gcacacagaa      540
aaacgaccgt accggaaccg gaacgctttc catttttggt catcagatgc gttttaacct      600
gcaagatgga ttcccgctgg tgacaactaa acgttgccac ctgcgttcca tcatccatga     660
actgctgtgg tttctgcagg gcgacactaa cattgcttat ctacacgaaa caatgtcac      720 catctgggac gaatgggccg atgaaaacgg cgacctcggg ccagtgtatg gtaaacagtg      780
gcgcgcctgg ccaacgccag atggtcgtca tattgaccag atcactacgg tactgaacca    840
gctgaaaaac gacccggatt cgcgccgcat tattgtttca gcgtggaacg taggcgaact      900
ggataaaatg cgctggcac cgtgccatgc attcttccag ttctatgtgg cagacggcaa      960
actctcttgc cagctttatc agcgctcctg tgacgtcttc ctcggcctgc cgttcaacat    1020
tgccagctac gcgttattgg tgcatatgat ggcgcagcag tgcgatctgg aagtgggtga    1080
ttttgtctgg accggtggcg acacgcatct gtacagcaac catatggatc aaactcatct    1140
gcaattaagc cgcgaaccgc gtccgctgcc gaagttgatt atcaaacgta acccgaatc     1200 catcttcgac taccgtttcg aagactttga gattgaaggc tacgatccgc atccgggcat    1260
taaagcgccg gtggctatct aattacgaaa catcctgcca gagccgacgc cagtgtgcgt    1320
cggttttttt accctccgtt aaattcttcg agacgccttc ccgaaggcgc cattcgccat    1380
tcaggctgcg caactgttgg gaagggcgat cggtgcgggc ctcttcgcta ttacgccagc   1440
tggcgaaagg gggatgtgct gcaaggcgat taagttgggt aacgccaggg ttttcccagt    1500
cacgacgttg taaaacgacg gccagtgcca gctttctttt aatgaagcag ggcatcagga   1560
cggtatcttt gtggagaaag cagagtaatc ttattcagcc tgactggtgg gaaaccacca   1620
gtcagaatgt gttagcgcat gttgacaaaa ataccattag tcacattatc cgtcagtcgg   1680
acgacatggt agataacctg tttattatgc gttttgatct tacgtttaat attacctta     1740 tgcgatgaaa cggtcttggc tttgatattc atttggtcag agatttgaat ggttccctga   1800
cctgccatcc acattcgcaa catactcgat tcggttcggc tcaatgataa cgtcggcata   1860
tttaaaaacg aggttatcgt tgtctctttt ttcagaatat cgccaaggat atcgtcgaga   1920
gattccggtt taatcgattt agaactgatc aataaatttt ttctgaccaa tagatattca   1980
tcaaaatgaa cattggcaat tgccataaaa acgataaata acgtattggg atgttgatta    2040
atgatgagct tgatacgctg actgttagaa gcatcgtgga tgaaacagtc ctcattaata   2100
aacaccactg aagggcgctg tgaatcacaa gctatggcaa ggtcatcaac ggtttcaatg   2160
tcgttgattt ctcttttttt aacccctcta ctcaacagat accggttaa acctagtcgg    2220 gtgtaactac ataaatccat aataatcgtt gacatggcat accctcactc aatgcgtaac   2280
gataattccc cttacctgaa tatttcatca tgactaaacg gaacaacatg ggtcacctaa    2340
tgcgccactc tcgcgatttt tcaggcggac ttactatccc gtaaagtgtt gtataatttg   2400
cctggaattg tcttaaagta aagtaaatgt tgcgatatgt gagtgagctt aaaacaaata   2460
```

```
tttcgctgca ggagtatcct ggaagatgtt cgtagaagct tactgctcac aagaaaaaag    2520
gcacgtcatc tgacgtgcct tttttatttg tactaccctg tacgattact gcagctcgag    2580
ttattataat tttacccacg attcgggaat aatatcatgt ttaatatctt tcttaaacca    2640
tttactcgga gcaattactg tttttatttt attttcattt aaccaagcag cccaccaact    2700
gaaagaacta tttgaaatta tattattttt acatttactc ataagcagca tatctaattc    2760
aacatgataa gcatcacctt gaacaaaaca tatttgatta ttaaaaaata tattttccct    2820
gcaccacttt atatcatcag aaaaaatgaa gagaagggtt tttttattaa taacacctttt    2880 attcatcaaa taatcaatgg cacgttcaaa atattttttca ctacatgtgc catgagtttc    2940
atttgctatt ttactggaaa cataatcacc tcttctaata tgtaatgaac aagtatcatt    3000
ttctttaatt aaattaagca attcattttg ataactatta aacttggttt taggttgaaa    3060
ttcctttatc aactcatgcc taaattcctt aaaatatttt tcagtttgaa ataaccgac     3120 gattttttta tttatacttt tggtatcaat atctggatca tactctaaac ttttctcaac    3180
gtaatgcttt ctgaacattc cttttttcat gaaatgtggg atttttttcgg aaaataagta   3240 tttttcaaat ggccatgctt tttttacaaa ttctgaacta caagataatt caactaatct    3300
taatggatga gttttatatt ttactgcatc agatatatca acagtcaaat tttgatgagt    3360 tcttttttgca atagcaaatg cagttgcata ctgaaacatt tgattaccaa gaccaccaat    3420
aattttaact tccatatgta tatctccttc ttctagaatt ctaaaaattg attgaatgta    3480
tgcaaataaa tgcatacacc ataggtgtgg tttaatttga tgcccttttt cagggctgga    3540
atgtgtaaga gcggggttat ttatgctgtt gttttttttgt tactcgggaa gggctttacc    3600
tcttccgcat aaacgcttcc atcagcgttt atagttaaaa aaatctttcg gaactggttt    3660
tgcgcttacc ccaaccaaca ggggatttgc tgctttccat tgagcctgtt tctctgcgcg    3720
acgttcgcgg cggcgtgttt gtgcatccat ctggattctc ctgtcagtta gctttggtgg    3780
tgtgtggcag ttgtagtcct gaacgaaaac ccccgcgat tggcacattg gcagctaatc     3840
cggaatcgca cttacggcca atgcttcgtt tcgtatcaca cacccccaaag ccttctgctt    3900 tgaatgctgc ccttcttcag ggcttaattt ttaagagcgt caccttcatg gtggtcagtg    3960
cgtcctgctg atgtgctcag tatcaccgcc agtggtattt atgtcaacac cgccagagat    4020
aatttatcac cgcagatggt tatctgtatg ttttttatat gaatttattt tttgcagggg    4080
ggcattgttt ggtaggtgag agatcaattc tgcattaatg aatcggccaa cgcgcgggga    4140
gaggcggttt gcgtattggg cgctcttccg cttcctcgct cactgactcg ctgcgctcgg    4200
tcgttcggct gcggcgagcg gtatcagctc actcaaaggc ggtaatacgg ttatccacag    4260
aatcagggga taacgcagga agaacatgt gagcaaaagg ccagcaaaag gccaggaacc    4320
gtaaaaaggc cgcgttgctg gcgttttttcc ataggctccg cccccctgac gagcatcaca    4380
aaaatcgacg ctcaagtcag aggtggcgaa acccgacagg actataaaga taccaggcgt    4440 ttcccctgg aagctccctc gtgcgctctc ctgttccgac cctgccgctt accggatacc     4500
tgtccgcctt tctcccttcg ggaagcgtgg cgctttctca gctcacgc tgtaggtatc      4560 tcagttcggt gtaggtcgtt cgctccaagc tgggctgtgt gcacgaaccc cccgttcagc    4620
ccgaccgctg cgccttatcc ggtaactatc gtcttgagtc aacccggta agacacgact     4680 tatcgccact ggcagcagcc actggtaaca ggattagcag agcgaggtat gtaggcggtg    4740
ctacagagtt cttgaagtgg tggcctaact acggctacac tagaaggaca gtatttggta    4800
tctgcgctct gctgaagcca gttaccttcg gaaaaagagt tggtagctct tgatccggca    4860
```

-continued

```
aacaaaccac cgctggtagc ggtggttttt ttgtttgcaa gcagcagatt acgcgcagaa    4920
aaaaaggatc tcaagaagat cctttgatct tttctacggg gtctgacgct cagtggaacg    4980
aaaactcacg ttaagggatt ttggtcatga gattatcaaa aaggatcttc acctagatcc    5040 tttaaatta aaaatgaagt tttaaatcaa tctaaagtat atatgagtaa acttggtctg     5100
acagttacca atgcttaatc agtgaggcac ctatctcagc gatctgtcta tttcgttcat    5160
ccatagttgc ctgactcccc gtcgtgtaga taactacgat acgggagggc ttaccatctg    5220
gccccagtgc tgcaatgata ccgcgagacc cacgctcacc ggctccagat ttatcagcaa    5280
taaaccagcc agccggaagg gccgagcgca gaagtggtcc tgcaacttta tccgcctcca    5340
tccagtctat taattgttgc cgggaagcta gagtaagtag ttcgccagtt aatagtttgc    5400
gcaacgttgt tgccattgct acaggcatcg tggtgtcacg ctcgtcgttt ggtatggctt    5460
cattcagctc cggttcccaa cgatcaaggc gagttacatg atcccccatg ttgtgcaaaa    5520
aagcggttag ctccttcggt cctccgatcg ttgtcagaag taagttggcc gcagtgttat    5580
cactcatggt tatggcagca ctgcataatt ctcttactgt catgccatcc gtaagatgct    5640
tttctgtgac tggtgagtac tcaaccaagt cattctgaga atagtgtatg cggcgaccga    5700
gttgctcttg cccggcgtca atacgggata ataccgcgcc acatagcaga actttaaaag    5760
tgctcatcat tggaaaacgt tcttcggggc gaaaactctc aaggatctta ccgctgttga    5820
gatccagttc gatgtaaccc actcgtgcac ccaactgatc ttcagcatct tttactttca    5880
ccagcgtttc tgggtgagca aaaacaggaa ggcaaaatgc cgcaaaaaag gaataagggc    5940 gacacggaa atgttgaata ctcatactct tcctttttca atattattga agcatttatc     6000
agggttattg tctcatgagc ggatacatat ttgaatgtat ttagaaaaat aaacaaatag    6060
gggttccgcg cacatttccc cgaaaagtgc cacctgacgt ctaagaaacc attattatca    6120
tgacattaac ctataaaaat aggcgtatca cgaggccctt cgtc                     6165
```

<210> SEQ ID NO 2
<211> LENGTH: 6290
<212> TYPE: DNA
<213> ORGANISM: Artificial Sequence
<220> FEATURE:
<223> OTHER INFORMATION: Sequence of pG176.

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatatg cggtgtgaaa taccgcacag atgcgtaagg agaaaatacc gcatcaggcg    240
ccatgaaaca gtatttagaa ctgatgcaaa aagtgctcga cgaaggcaca cagaaaaacg    300
accgtaccgg aaccggaacg cttttccattt ttggtcatca gatgcgtttt aacctgcaag    360
atggattccc gctggtgaca actaaacgtt gccacctgcg ttccatcatc catgaactgc    420
tgtggtttct gcagggcgac actaacattg cttatctaca cgaaaacaat gtcaccatct    480
gggacgaatg ggccgatgaa aacggcgacc tcggccagt gtatggtaaa cagtggcgcg    540
cctggccaac gccagatggt cgtcatattg accagatcac tacggtactg aaccagctga    600 aaacgaccc ggattcgcgc cgcattattg tttcagcgtg gaacgtaggc gaactggata    660
aaatggcgct ggcaccgtgc catgcattct tccagttcta tgtggcagac ggcaaactct    720
```

```
cttgccagct ttatcagcgc tcctgtgacg tcttcctcgg cctgccgttc aacattgcca    780
gctacgcgtt attggtgcat atgatggcgc agcagtgcga tctggaagtg ggtgattttg    840
tctggaccgg tggcgacacg catctgtaca gcaaccatat ggatcaaact catctgcaat    900
taagccgcga accgcgtccg ctgccgaagt tgattatcaa acgtaaaccc gaatccatct    960
tcgactaccg tttcgaagac tttgagattg aaggctacga tccgcatccg ggcattaaag   1020
cgccggtggc tatctaaggc gccattcgcc attcaggctg cgcaactgtt gggaagggcg   1080
atcggtgcgg gcctcttcgc tattacgcca gctggcgaaa ggggatgtg ctgcaaggcg    1140 attaagttgg gtaacgccag ggttttccca gtcacgacgt tgtaaaacga cggccagtgc   1200
caagctttct ttaatgaagc agggcatcag gacggtatct ttgtggagaa agcagagtaa   1260
tcttattcag cctgactggt gggaaaccac cagtcagaat gtgttagcgc atgttgacaa   1320
aaataccatt agtcacatta tccgtcagtc ggacgacatg gtagataacc tgtttattat   1380
gcgttttgat cttacgttta atattacctt tatgcgatga aacggtcttg gctttgatat   1440
tcatttggtc agagatttga atggttccct gacctgccat ccacattcgc aacatactcg   1500
attcggttcg gctcaatgat aacgtcggca tatttaaaaa cgaggttatc gttgtctctt   1560
ttttcagaat atcgccaagg atatcgtcga gagattccgg tttaatcgat ttagaactga   1620
tcaataaatt ttttctgacc aatagatatt catcaaaatg aacattggca attgccataa   1680
aaacgataaa taacgtattg ggatgttgat taatgatgag cttgatacgc tgactgttag   1740
aagcatcgtg gatgaaacag tcctcattaa taaacaccac tgaagggcgc tgtgaatcac   1800
aagctatggc aaggtcatca acggtttcaa tgtcgttgat ttctcttttt ttaacccctc   1860
tactcaacag ataccggtt aaacctagtc gggtgtaact acataaatcc ataataatcg    1920
ttgacatggc ataccctcac tcaatgcgta acgataattc cccttacctg aatatttcat   1980
catgactaaa cggaacaaca tgggtcacct aatgcgccac tctcgcgatt tttcaggcgg   2040
acttactatc ccgtaaagtg ttgtataatt tgcctggaat tgtcttaaag taaagtaaat   2100
gttgcgatat gtgagtgagc ttaaaacaaa tatttcgctg caggagtatc ctggaagatg   2160
ttcgtagaag cttactgctc acaagaaaaa aggcacgtca tctgacgtgc ctttttatt    2220 tgtactaccc tgtacgatta ctgcagctcg agttaattca aatcttcttc agaaatcaat   2280
ttttgttcca aacccaattt tttaaccaac tttctcaccg cgcgcaacaa aggcaaggat   2340
ttttgataag ctttgcgata gattttaaaa gtggtgtttt gagagagttc taataaaggc   2400
gaagcgtttt gtaaaagccg gtcataatta accctcaaat catcataatt aaccctcaaa   2460
tcatcaatgg atactaacgg cttatgcaga tcgtactccc acatgaaaga tgttgagaat   2520
ttgtgataaa tcgtatcgtt ttctaaaatc gttttaaaaa atctaggat ttttttaaaa    2580 ctcaaatctt ggtaaaagta agctttccca tcaagggtgt ttaaagggtt ttcatagagc   2640
atgtctaaat aagcgtttgg gtgcgtgtgc aggtatttga tataatcaat cgcttcatca   2700
aagttgttga aatcatgcac attcacaaaa cttttagggt taaaatcttt cgccacgctg   2760
ggactccccc aataaatagg aatggtatgg ctaaaatacg catcaaggat ttttttcggtt   2820 acatagccat aaccttgcga gttttcaaaa cagagattga acttgtattg cttaaaaac    2880 tcgcttttgt ttccaacctt atagcctaaa gtgtttctca cacttcctcc cccagtaact   2940
ggctctatgg aatttagagc gtcataaaaa gcgttcctca taggagcgtt agcgttgctc   3000
gctacaaaac tggcaaaccc tctttttaaa agatcgctct catcattcac tactgcgcac   3060
aaattagggt ggttttcttt aaaatgatga gagggttttt ttaaagcata aaggctgttg   3120
```

```
tctttgagtt tgtagggcgc agtggtgtca ttaacaagct cggctttata gtgcaaatgg    3180
gcataataca aaggcattct caaataacga tcattaaaat ccaattcatc aaagcctatg    3240
gcgtaatcaa agaggttgaa attaggtgat tcgttttcac cggtgtaaaa cactcgttta    3300
gtgttttgat aagataaaat ctttctagcc gctccaagag gattgctaaa aactagatct    3360
gaaaattcat tggggttttg gtggagggtg attgcgtagc gttggcttag gataaaataa    3420
agaacgctct ttttaaattc tttaatttct tcatctcccc accaattcgc cacagcgatt    3480
tttagggggg ggggggagag tttagaggcc attttttcaa tggaagcgct ttctataaag    3540
gcgtctaata ggggttggaa catatgtata tctccttctt gaattctaaa aattgattga    3600
atgtatgcaa ataaatgcat acaccatagg tgtggtttaa tttgatgccc ttttttcaggg    3660 ctggaatgtg taagagcggg gttatttatg ctgttgtttt tttgttactc gggaagggct    3720
ttacctcttc cgcataaacg cttccatcag cgtttatagt taaaaaaatc tttcggaact    3780
ggttttgcgc ttaccccaac caacagggga tttgctgctt ccattgagc ctgtttctct    3840 gcgcgacgtt cgcggcggcg tgtttgtgca tccatctgga ttctcctgtc agttagcttt    3900
ggtggtgtgt ggcagttgta gtcctgaacg aaaacccccc gcgattggca cattggcagc    3960
taatccggaa tcgcacttac ggccaatgct tcgtttcgta tcacacaccc caaagccttc    4020
tgctttgaat gctgcccttc ttcagggctt aattttttaag agcgtcacct tcatggtggt    4080
cagtgcgtcc tgctgatgtg ctcagtatca ccgccagtgg tatttatgtc aacaccgcca    4140
gagataattt atcaccgcag atggttatct gtatgttttt tatatgaatt tattttttgc    4200
aggggggcat tgtttggtag gtgagagatc aattctgcat taatgaatcg ccaacgcgc    4260 ggggagaggc ggtttgcgta ttgggcgctc ttccgcttcc tcgctcactg actcgctgcg    4320
ctcggtcgtt cggctgcggc gagcggtatc agctcactca aaggcggtaa tacggttatc    4380
cacagaatca ggggataacg caggaaagaa catgtgagca aaaggccagc aaaaggccag    4440
gaaccgtaaa aaggccgcgt tgctggcgtt tttccatagg ctccgccccc ctgacgagca    4500
tcacaaaaat cgacgctcaa gtcagaggtg gcgaaacccg acaggactat aaagatacca    4560
ggcgtttccc cctggaagct ccctcgtgcg ctctcctgtt ccgaccctgc cgcttaccgg    4620
atacctgtcc gcctttctcc cttcgggaag cgtggcgctt tctcatagct cacgctgtag    4680
gtatctcagt tcggtgtagg tcgttcgctc caagctgggc tgtgtgcacg aaccccccgt    4740
tcagcccgac cgctgcgcct tatccggtaa ctatcgtctt gagtccaacc cggtaagaca    4800
cgacttatcg ccactggcag cagccactgg taacaggatt agcagagcga ggtatgtagg    4860
cggtgctaca gagttcttga agtggtggcc taactacggc tacactagaa ggacagtatt    4920
tggtatctgc gctctgctga gccagttac cttcggaaaa agagttggta gctcttgatc    4980
cggcaaacaa accaccgctg gtagcggtgg tttttttgtt tgcaagcagc agattacgcg    5040
cagaaaaaaa ggatctcaag aagatccttt gatcttttct acgggtctg acgctcagtg    5100 gaacgaaaac tcacgttaag ggattttggt catgagatta tcaaaaagga tcttcaccta    5160 gatccttta aattaaaaat gaagttttaa atcaatctaa agtatatatg agtaaacttg    5220
gtctgacagt taccaatgct taatcagtga ggcacctatc tcagcgatct gtctatttcg    5280
ttcatccata gttgcctgac tccccgtcgt gtagataact acgatacggg agggcttacc    5340
atctggcccc agtgctgcaa tgataccgcg agacccacgc tcaccggctc cagatttatc    5400
agcaataaac cagccagccg gaagggccga gcgcagaagt ggtcctgcaa ctttatccgc    5460
```

-continued

| | |
|---|---|
| ctccatccag tctattaatt gttgccggga agctagagta agtagttcgc cagttaatag | 5520 |
| tttgcgcaac gttgttgcca ttgctacagg catcgtggtg tcacgctcgt cgtttggtat | 5580 |
| ggcttcattc agctccggtt cccaacgatc aaggcgagtt acatgatccc ccatgttgtg | 5640 |
| caaaaaagcg gttagctcct tcggtcctcc gatcgttgtc agaagtaagt tggccgcagt | 5700 |
| gttatcactc atggttatgg cagcactgca taattctctt actgtcatgc catccgtaag | 5760 |
| atgcttttct gtgactggtg agtactcaac caagtcattc tgagaatagt gtatgcggcg | 5820 |
| accgagttgc tcttgcccgg cgtcaatacg ggataatacc gcgccacata gcagaacttt | 5880 |
| aaaagtgctc atcattggaa aacgttcttc ggggcgaaaa ctctcaagga tcttaccgct | 5940 |
| gttgagatcc agttcgatgt aacccactcg tgcacccaac tgatcttcag catcttttac | 6000 |
| tttcaccagc gtttctgggt gagcaaaaac aggaaggcaa aatgccgcaa aaagggaat | 6060 |
| aagggcgaca cggaaatgtt gaatactcat actcttcctt tttcaatatt attgaagcat | 6120 |
| ttatcagggt tattgtctca tgagcggata catatttgaa tgtatttaga aaaataaaca | 6180 |
| aatagggggtt ccgcgcacat ttccccgaaa agtgccacct gacgtctaag aaaccattat | 6240 |
| tatcatgaca ttaacctata aaaataggcg tatcacgagg ccctttcgtc | 6290 |

<210> SEQ ID NO 3
<211> LENGTH: 7250
<212> TYPE: DNA
<213> ORGANISM: Artificial Sequence
<220> FEATURE:
<223> OTHER INFORMATION: Sequence of pG177.

<400> SEQUENCE: 3

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatatg cggtgtgaaa taccgcacag atgcgtaagg agaaaatacc gcatcaggcg | 240 |
| ccatgaaaca gtatttagaa ctgatgcaaa aagtgctcga cgaaggcaca cagaaaaacg | 300 |
| accgtaccgg aaccggaacg cttttccattt ttggtcatca gatgcgtttt aacctgcaag | 360 |
| atggattccc gctggtgaca actaaacgtt gccacctgcg ttccatcatc catgaactgc | 420 |
| tgtggttttct gcagggcgac actaacattg cttatctaca cgaaaacaat gtcaccatct | 480 |
| gggacgaatg ggccgatgaa aacggcgacc tcgggccagt gtatggtaaa cagtggcgcg | 540 |
| cctggccaac gccagatggt cgtcatattg accagatcac tacggtactg aaccagctga | 600 |
| aaaacgaccc ggattcgcgc cgcattattg tttcagcgtg aacgtaggc gaactggata | 660 |
| aaatggcgct ggcaccgtgc catgcattct tccagttcta tgtggcagac ggcaaactct | 720 |
| cttgccagct ttatcagcgc tcctgtgacg tcttcctcgg cctgccgttc aacattgcca | 780 |
| gctacgcgtt attggtgcat atgatggcgc agcagtgcga tctggaagtg ggtgattttg | 840 |
| tctggaccgg tggcgacacg catctgtaca gcaaccatat ggatcaaact catctgcaat | 900 |
| taagccgcga accgcgtccg ctgccgaagt tgattatcaa acgtaaaccc gaatccatct | 960 |
| tcgactaccg tttcgaagac tttgagattg aaggctacga tccgcatccg gcattaaag | 1020 |
| cgccggtggc tatctaaggc gccattcgcc attcaggctg cgcaactgtt gggaagggcg | 1080 |
| atcggtgcgg gcctcttcgc tattacgcca gctggcgaaa gggggatgtg ctgcaaggcg | 1140 |
| attaagttgg gtaacgccag ggttttccca gtcacgacgt tgtaaaacga cggccagtgc | 1200 |
| caagcttttct ttaatgaagc agggcatcag gacggtatct ttgtggagaa agcagagtaa | 1260 |

```
tcttattcag cctgactggt gggaaaccac cagtcagaat gtgttagcgc atgttgacaa    1320
aaataccatt agtcacatta tccgtcagtc ggacgacatg gtagataacc tgtttattat    1380
gcgttttgat cttacgttta atattacctt tatgcgatga aacggtcttg gctttgatat    1440
tcatttggtc agagatttga atggttccct gacctgccat ccacattcgc aacatactcg    1500
attcggttcg gctcaatgat aacgtcggca tatttaaaaa cgaggttatc gttgtctctt    1560
ttttcagaat atcgccaagg atatcgtcga gagattccgg tttaatcgat ttagaactga    1620
tcaataaatt ttttctgacc aatagatatt catcaaaatg aacattggca attgccataa    1680
aaacgataaa taacgtattg ggatgttgat taatgatgag cttgatacgc tgactgttag    1740
aagcatcgtg gatgaaacag tcctcattaa aaacaccac tgaagggcgc tgtgaatcac    1800
aagctatggc aaggtcatca acggtttcaa tgtcgttgat ttctcttttt ttaacccctc    1860
tactcaacag atacccggtt aaacctagtc gggtgtaact acataaatcc ataataatcg    1920 ttgacatgg atacccctcac tcaatgcgta acgataattc cccttacctg aatatttcat    1980
catgactaaa cggaacaaca tgggtcacct aatgcgccac tctcgcgatt tttcaggcgg    2040
acttactatc ccgtaaagtg ttgtataatt tgcctggaat tgtcttaaag taaagtaaat    2100
gttgcgatat gtgagtgagc ttaaaacaaa tatttcgctg caggagtatc ctggaagatg    2160
ttcgtagaag cttactgctc acaagaaaaa aggcacgtca tctgacgtgc ctttttttatt    2220 tgtactaccc tgtacgatta ctgcagctcg agttaattca aatcttcttc agaaatcaat    2280
ttttgttcag cgttatactt tgggatttt acctcaaaat gggattctat tttcacccac    2340
tccttacaaa ggatattctc atgcccaaaa agccagtgtt tggggccaat aatgattttt    2400
tctggatttt ctatcaaata ggccgcccac cagctataag tgctattagc gataatgcca    2460
tgctgacaag attgcatgag cagcatgtcc caatacgcct cttcttcttt atccctagtg    2520
gtcatgtcca taaagggta gccaagatca agattttgcg tgaattctaa gtcttcgcaa    2580
aacacaaaaa gctccatgtt tggcacgcgc tttgccatat actcaagcgc ctttttttga    2640
tagtcaatac caagctgaca gccaatcccc acataatccc ctcttcttat atgcacaaac    2700
acgctgtttt tagcggctaa aatcaaagaa agcttgcact gatattcttc ctctttttta    2760
ttattattct tattattttc gggtggtggt ggtagagtga aggtttgctt gattaaaggg    2820
gatatagcat caaagtatcg tggatcttgg aaatagccaa aaaataagt caagcggctt    2880 ggctttagca atttaggctc gtattcaaaa acgatttctt gactcaccct atcaaatccc    2940
atgcatttga gcgcgtctct tactagcttg gggaggtgtt gcattttagc tatagcgatt    3000
tctttcgcgc tcgcataggg caaatcaata gggaaaagtt ctaattgcat tttcctatcg    3060
ctccaatcaa aagaagtgat atctaacagc acaggcgtat tagagtgttt ttgcaaactt    3120
ttagcgaaag cgtattgaaa catttgattc ccaagccctc cgcaaatttg caccaccta    3180 aaagccatat gtatatctcc ttcttgctcg agttaattca aatcttcttc agaaatcaat    3240
ttttgttcca aacccaattt tttaaccaac tttctcaccg cgcgcaacaa aggcaaggat    3300
ttttgataag ctttgcgata gattttaaaa gtggtgtttt gagagagttc taataaaggc    3360
gaagcgtttt gtaaaagccg gtcataatta accctcaaat catcataatt aaccctcaaa    3420
tcatcaatgg atactaacgg cttatgcaga tcgtactccc acatgaaaga tgttgagaat    3480
ttgtgataaa tcgtatcgtt ttctaaaatc gttttaaaaa atctaggat ttttttaaaa    3540 ctcaaatctt ggtaaaagta agctttccca tcaagggtgt ttaaagggtt ttcatagagc    3600
```

```
atgtctaaat aagcgtttgg gtgcgtgtgc aggtatttga tataatcaat cgcttcatca    3660
aagttgttga aatcatgcac attcacaaaa cttttagggt taaaatcttt cgccacgctg    3720
ggactccccc aataaatagg aatggtatgg ctaaaatacg catcaaggat tttttcggtt    3780
acatagccat aaccttgcga gttttcaaaa cagagattga acttgtattg cttaaaaac     3840 tcgcttttgt ttccaacctt atagcctaaa gtgtttctca cacttcctcc cccagtaact    3900
ggctctatgg aatttagagc gtcataaaaa gcgttcctca taggagcgtt agcgttgctc    3960
gctacaaaac tggcaaaccc tcttttaaa agatcgctct catcattcac tactgcgcac     4020
aaattagggt ggttttcttt aaaatgatga gagggttttt ttaaagcata aaggctgttg    4080
tctttgagtt tgtagggcgc agtggtgtca ttaacaagct cggctttata gtgcaaatgg    4140
gcataataca aaggcattct caaataacga tcattaaaat ccaattcatc aaagcctatg    4200
gcgtaatcaa agaggttgaa attaggtgat tcgttttcac cggtgtaaaa cactcgttta    4260
gtgttttgat aagataaaat ctttctagcc gctccaagag gattgctaaa aactagatct    4320
gaaaattcat tggggttttg gtggagggtg attgcgtagc gttggcttag gataaaataa    4380
agaacgctct ttttaaattc tttaatttct tcatctcccc accaattcgc cacagcgatt    4440
tttagggggg ggggggagag tttagaggcc attttttcaa tggaagcgct ttctataaag    4500
gcgtctaata ggggttggaa catatgtata tctccttctt gaattctaaa aattgattga    4560
atgtatgcaa ataaatgcat acaccatagg tgtggtttaa tttgatgccc ttttcaggg    4620 ctggaatgtg taagagcggg gttatttatg ctgttgtttt tttgttactc gggaagggct    4680
ttacctcttc cgcataaacg cttccatcag cgtttatagt taaaaaaatc tttcggaact    4740
ggttttgcgc ttaccccaac caacagggga tttgctgctt tccattgagc ctgtttctct    4800
gcgcgacgtt cgcggcggcg tgtttgtgca tccatctgga ttctcctgtc agttagcttt    4860
ggtggtgtgt ggcagttgta gtcctgaacg aaaaccccc gcgattggca cattggcagc    4920
taatccggaa tcgcacttac ggccaatgct tcgtttcgta tcacacaccc caaagccttc    4980
tgctttgaat gctgcccttc ttcagggctt aattttaag agcgtcacct tcatggtggt    5040
cagtgcgtcc tgctgatgtg ctcagtatca ccgccagtgg tatttatgtc aacaccgcca    5100
gagataattt atcaccgcag atggttatct gtatgttttt tatatgaatt tattttttgc    5160
aggggggcat tgtttggtag gtgagagatc aattctgcat taatgaatcg gccaacgcgc    5220
ggggagaggc ggtttgcgta ttgggcgctc ttccgcttcc tcgctcactg actcgctgcg    5280
ctcggtcgtt cggctgcggc gagcggtatc agctcactca aaggcggtaa tacggttatc    5340
cacagaatca ggggataacg caggaaagaa catgtgagca aaaggccagc aaaaggccag    5400
gaaccgtaaa aaggccgcgt tgctggcgtt ttttccatag gctccgcccc ctgacgagca    5460
tcacaaaaat cgacgctcaa gtcagaggtg gcgaaacccg acaggactat aaagatacca    5520
ggcgtttccc cctggaagct ccctcgtgcg ctctcctgtt ccgaccctgc cgcttaccgg    5580
atacctgtcc gcctttctcc cttcgggaag cgtggcgctt tctcatagct cacgctgtag    5640
gtatctcagt tcggtgtagg tcgttcgctc caagctgggc tgtgtgcacg aaccccccgt    5700
tcagcccgac cgctgcgcct tatccggtaa ctatcgtctt gagtccaacc cggtaagaca    5760
cgacttatcg ccactggcag cagccactgg taacaggatt agcagagcga ggtatgtagg    5820
cggtgctaca gagttcttga agtggtggcc taactacggc tacactagaa ggacagtatt    5880
tggtatctgc gctctgctga agccagttac cttcggaaaa agagttggta gctcttgatc    5940
cggcaaacaa accaccgctg gtagcggtgg ttttttttgtt tgcaagcagc agattacgcg    6000
```

```
cagaaaaaaa ggatctcaag aagatccttt gatcttttct acggggtctg acgctcagtg    6060
gaacgaaaac tcacgttaag ggattttggt catgagatta tcaaaaagga tcttcaccta    6120 gatccttta aattaaaaat gaagttttaa atcaatctaa agtatatatg agtaaacttg    6180
gtctgacagt taccaatgct taatcagtga ggcacctatc tcagcgatct gtctatttcg    6240
ttcatccata gttgcctgac tccccgtcgt gtagataact acgatacggg agggcttacc    6300
atctggcccc agtgctgcaa tgataccgcg agacccacgc tcaccggctc cagatttatc    6360
agcaataaac cagccagccg aagggccga gcgcagaagt ggtcctgcaa ctttatccgc    6420
ctccatccag tctattaatt gttgccggga agctagagta agtagttcgc cagttaatag    6480
tttgcgcaac gttgttgcca ttgctacagg catcgtggtg tcacgctcgt cgtttggtat    6540
ggcttcattc agctccggtt cccaacgatc aaggcgagtt acatgatccc ccatgttgtg    6600 caaaaagcg gttagctcct tcggtcctcc gatcgttgtc agaagtaagt tggccgcagt    6660
gttatcactc atggttatgg cagcactgca taattctctt actgtcatgc catccgtaag    6720
atgcttttct gtgactggtg agtactcaac caagtcattc tgagaatagt gtatgcggcg    6780
accgagttgc tcttgcccgg cgtcaatacg ggataatacc gcgccacata gcagaacttt    6840
aaaagtgctc atcattggaa aacgttcttc ggggcgaaaa ctctcaagga tcttaccgct    6900
gttgagatcc agttcgatgt aacccactcg tgcaccaac tgatcttcag catcttttac    6960
tttcaccagc gtttctgggt gagcaaaaac aggaaggcaa aatgccgcaa aaaagggaat    7020
aagggcgaca cggaaatgtt gaatactcat actcttcctt tttcaatatt attgaagcat    7080
ttatcagggt tattgtctca tgagcggata catatttgaa tgtatttaga aaaataaaca    7140 aatagggggtt ccgcgcacat ttccccgaaa agtgccacct gacgtctaag aaaccattat    7200
tatcatgaca ttaacctata aaaataggcg tatcacgagg ccctttcgtc                7250

<210> SEQ ID NO 4
<211> LENGTH: 870
<212> TYPE: DNA
<213> ORGANISM: Bacteroides fragilis

<400> SEQUENCE: 4
atgattgtat catctttgcg aggaggattg gggaatcaaa tgtttattta cgctatggtg      60
aaggccatgg cattaagaaa caatgtacca ttcgcttta atttgactac tgattttgca     120
aatgatgaag tttataaaag gaaacttta ttatcatatt ttgcattaga cttgcctgaa     180 aataaaaat taacatttga ttttcatat gggaattatt atagaaggct aagtcgtaat     240
ttaggttgtc atatacttca tccatcatat cgttatattt gcgaagagcg ccctccccac     300
tttgaatcaa ggtaattag ttctaagatt acaaatgctt ttctggaagg atattggcag     360
tcagaaaaat attttcttga ttataaacaa gagataaaag aggactttgt aatacaaaaa     420
aaattagaat acacatcgta tttggaattg aagaaaataa aattgctaga taagaatgcc     480
ataatgattg gggttagacg gtatcaggaa agtgatgtag ctcctggtgg agtgttagaa     540
gatgattact ataaatgtgc tatggatatt atggcatcaa aagttacttc tcctgttttc     600
ttttgttttt cacaagattt agaatggggtt gaaaacatc tagcgggaaa atatcctgtt     660
cgtttgataa gtaaaaagga ggatgatagt ggtactatag atgatatgtt tctaatgatg     720 catttttcgta attatataat atcgaatagc tctttttact ggtggggagc atggctttcg     780
aaatatgatg ataagctggt gattgctcca ggtaatttta taaataagga ttctgtacca     840
```

```
gaatcttggt ttaaattgaa tgtaagataa                                  870
```

<210> SEQ ID NO 5
<211> LENGTH: 6244
<212> TYPE: DNA
<213> ORGANISM: Artificial Sequence
<220> FEATURE:
<223> OTHER INFORMATION: Sequence of pG171.

<400> SEQUENCE: 5

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatatg cggtgtgaaa taccgcacag atgcgtaagg agaaaatacc gcatcaggcg   240
cctcctcaac ctgtatattc gtaaaccacg cccaatggga gctgtctcag gtttgttcct   300
gattggttac ggcgcgtttc gcatcattgt tgagttttc gccagcccg acgcgcagtt    360
taccggtgcc tgggtgcagt acatcagcat ggggcaaatt ctttccatcc cgatgattgt   420
cgcgggtgtg atcatgatgg tctgggcata tcgtcgcagc ccacagcaac acgtttcctg   480
aggaaccatg aaacagtatt tagaactgat gcaaaaagtg ctcgacgaag gcacacagaa   540
aaacgaccgt accggaaccg gaacgctttc cattttggt catcagatgc gttttaacct    600
gcaagatgga ttcccgctgg tgacaactaa acgttgccac ctgcgttcca tcatccatga   660
actgctgtgg tttctgcagg gcgacactaa cattgcttat ctacacgaaa acaatgtcac   720
catctgggac gaatgggccg atgaaaaacg cgacctcggg ccagtgtatg gtaaacagtg   780
gcgcgcctgg ccaacgccag atggtcgtca tattgaccag atcactacgg tactgaacca   840
gctgaaaaac gacccggatt cgcgccgcat tattgtttca gcgtggaacg taggcgaact   900
ggataaaatg gcgctggcac cgtgccatgc attcttccag ttctatgtgg cagacggcaa   960
actctcttgc cagctttatc agcgctcctg tgacgtcttc ctcggcctgc cgttcaacat  1020
tgccagctac gcgttattgg tgcatatgat ggcgcagcag tgcgatctgg aagtgggtga  1080
ttttgtctgg accggtggcg acacgcatct gtacagcaac catatggatc aaactcatct  1140
gcaattaagc cgcgaaccgc gtccgctgcc gaagttgatt atcaaacgta acccgaatc   1200
catcttcgac taccgtttcg aagactttga gattgaaggc tacgatccgc atccgggcat  1260
taaagcgccg gtggctatct aattacgaaa catcctgcca gagccgacgc cagtgtgcgt  1320
cggttttttt accctccgtt aaattcttcg agacgccttc ccgaaggcgc cattcgccat  1380
tcaggctgcg caactgttgg gaagggcgat cggtgcgggc ctcttcgcta ttacgccagc  1440
tggcgaaagg gggatgtgct gcaaggcgat taagttgggt aacgccaggg ttttcccagt  1500
cacgacgttg taaaacgacg gccagtgcca gctttctttt aatgaagcag ggcatcagga  1560
cggtatcttt gtggagaaag cagagtaatc ttattcagcc tgactggtgg gaaaccacca  1620
gtcagaatgt gttagcgcat gttgacaaaa ataccattag tcacattatc cgtcagtcgg  1680
acgacatggt agataaccctg tttattatgc gttttgatct tacgtttaat attacccttta  1740
tgcgatgaaa cggtcttggc tttgatattc atttggtcag agatttgaat ggttccctga  1800
cctgccatcc acattcgcaa catactcgat tcggttcggc tcaatgataa cgtcggcata  1860
tttaaaaacg aggttatcgt tgtctctttt ttcagaatat cgccaaggat atcgtcgaga  1920
gattccggtt taatcgattt agaactgatc aataaatttt ttctgaccaa tagatattca  1980
tcaaaatgaa cattggcaat tgccataaaa acgataaata acgtattggg atgttgatta  2040
```

```
atgatgagct tgatacgctg actgttagaa gcatcgtgga tgaaacagtc ctcattaata    2100
aacaccactg aagggcgctg tgaatcacaa gctatggcaa ggtcatcaac ggtttcaatg    2160
tcgttgattt ctcttttttt aaccctcta ctcaacagat acccggttaa acctagtcgg     2220
gtgtaactac ataaatccat aataatcgtt gacatggcat accctcactc aatgcgtaac    2280
gataattccc cttacctgaa tatttcatca tgactaaacg gaacaacatg ggtcacctaa    2340
tgcgccactc tcgcgatttt tcaggcggac ttactatccc gtaaagtgtt gtataatttg    2400
cctggaattg tcttaaagta aagtaaatgt tgcgatatgt gagtgagctt aaaacaaata    2460
tttcgctgca ggagtatcct ggaagatgtt cgtagaagct tactgctcac aagaaaaaag    2520
gcacgtcatc tgacgtgcct tttttatttg tactaccctg tacgattact gcagctcgag    2580
tttaattcaa atcttcttca gaaatcaatt tttgttcagc gttatacttt tgggatttta    2640
cctcaaaatg ggattctatt tcacccact ccttacaaag gatattctca tgcccaaaaa     2700
gccagtgttt ggggccaata atgattttt ctggattttc tatcaaatag gccgcccacc     2760
agctataagt gctattagcg ataatgccat gctgacaaga ttgcatgagc agcatgtccc    2820
aatacgcctc ttcttcttta tccctagtgg tcatgtccat aaaagggtag ccaagatcaa    2880
gattttgcgt gaattctaag tcttcgcaaa acacaaaaag ctccatgttt ggcacgcgct    2940
ttgccatata ctcaagcgcc ttttttgat agtcaataccc aagctgacag ccaatcccca    3000
cataatcccc tcttcttata tgcacaaaca cgctgttttt agcggctaaa atcaaagaaa    3060
gcttgcactg atattcttcc tcttttttat tattattctt attattttcg ggtggtggtg    3120
gtagagtgaa ggtttgcttg attaaagggg atatagcatc aaagtatcgt ggatcttgga    3180
aatagccaaa aaaataagtc aagcggcttg gctttagcaa tttaggctcg tattcaaaaa    3240
cgatttcttg actcacccta tcaaatccca tgcatttgag cgcgtctctt actagcttgg    3300
ggaggtgttg cattttagct atagcgattt ctttcgcgct cgcatagggc aaatcaatag    3360
ggaaaagttc taattgcatt ttcctatcgc tccaatcaaa agaagtgata tctaacagca    3420
caggcgtatt agagtgtttt tgcaaacttt tagcgaaagc gtattgaaac atttgattcc    3480
caagccctcc gcaaatttgc accaccttaa aagccatatg tatatctcct tcttgaattc    3540
taaaaattga ttgaatgtat gcaaataaat gcatacacca taggtgtggt ttaatttgat    3600
gccctttttc agggctggaa tgtgtaagag cggggttatt tatgctgttg ttttttttgtt   3660 actcgggaag ggctttacct cttccgcata aacgcttcca tcagcgttta tagttaaaaa    3720 aatcttcgg aactggtttt gcgcttaccc caaccaacag gggatttgct gctttccatt     3780
gagcctgttt ctctgcgcga cgttcgcggc ggcgtgtttg tgcatccatc tggattctcc    3840
tgtcagttag ctttggtggt gtgtggcagt tgtagtcctg aacgaaaacc cccgcgatt     3900 ggcacattgg cagctaatcc ggaatcgcac ttacggccaa tgcttcgttt cgtatcacac    3960
accccaaagc cttctgcttt gaatgctgcc cttcttcagg gcttaatttt taagagcgtc    4020
accttcatgg tggtcagtgc gtcctgctga tgtgctcagt atcaccgcca gtggtattta    4080
tgtcaacacc gccagagata atttatcacc gcagatggtt atctgtatgt ttttatatg     4140 aatttatttt ttgcaggggg gcattgtttg gtaggtgaga atcaattct gcattaatga     4200 atcggccaac gcgcggggag aggcggtttg cgtattgggc gctcttccgc ttcctcgctc    4260
actgactcgc tgcgctcggt cgttcggctg cggcgagcgg tatcagctca ctcaaaggcg    4320
gtaatacggt tatccacaga atcaggggat aacgcaggaa agaacatgtg agcaaaaggc    4380
```

```
cagcaaaagg ccaggaaccg taaaaaggcc gcgttgctgg cgttttttcca taggctccgc    4440 cccccctgacg agcatcacaa aaatcgacgc tcaagtcaga ggtggcgaaa cccgacagga    4500
ctataaagat accaggcgtt tccccctgga agctccctcg tgcgctctcc tgttccgacc    4560
ctgccgctta ccgatacct gtccgccttt ctcccttcgg gaagcgtggc gctttctcat    4620
agctcacgct gtaggtatct cagttcggtg taggtcgttc gctccaagct gggctgtgtg    4680
cacgaacccc ccgttcagcc cgaccgctgc gccttatccg gtaactatcg tcttgagtcc    4740
aacccggtaa gacacgactt atcgccactg gcagcagcca ctggtaacag gattagcaga    4800
gcgaggtatg taggcggtgc tacagagttc ttgaagtggt ggcctaacta cggctacact    4860
agaaggacag tatttggtat ctgcgctctg ctgaagccag ttaccttcgg aaaaagagtt    4920
ggtagctctt gatccggcaa acaaaccacc gctggtagcg gtggtttttt tgtttgcaag    4980
cagcagatta cgcgcagaaa aaaggatct caagaagatc ctttgatctt ttctacgggg    5040
tctgacgctc agtggaacga aaactcacgt taagggattt tggtcatgag attatcaaaa    5100
aggatcttca cctagatcct tttaaattaa aaatgaagtt ttaaatcaat ctaaagtata    5160
tatgagtaaa cttggtctga cagttaccaa tgcttaatca gtgaggcacc tatctcagcg    5220
atctgtctat ttcgttcatc catagttgcc tgactccccg tcgtgtagat aactacgata    5280
cgggagggct taccatctgg ccccagtgct gcaatgatac cgcgagaccc acgctcaccg    5340
gctccagatt tatcagcaat aaaccagcca gccggaaggg ccgagcgcag aagtggtcct    5400
gcaactttat ccgcctccat ccagtctatt aattgttgcc gggaagctag agtaagtagt    5460 tcgcagtta atagtttgcg caacgttgtt gccattgcta caggcatcgt ggtgtcacgc    5520
tcgtcgtttg gtatggcttc attcagctcc ggttcccaac gatcaaggcg agttacatga    5580
tcccccatgt tgtgcaaaaa agcggttagc tccttcggtc ctccgatcgt tgtcagaagt    5640
aagttggccg cagtgttatc actcatggtt atggcagcac tgcataattc tcttactgtc    5700
atgccatccg taagatgctt ttctgtgact ggtgagtact caaccaagtc attctgagaa    5760
tagtgtatgc ggcgaccgag ttgctcttgc ccggcgtcaa tacgggataa taccgcgcca    5820
catagcagaa ctttaaaagt gctcatcatt ggaaaacgtt cttcggggcg aaaactctca    5880
aggatcttac cgctgttgag atccagttcg atgtaaccca ctcgtgcacc caactgatct    5940
tcagcatctt ttactttcac cagcgtttct gggtgagcaa aaacaggaag gcaaaatgcc    6000
gcaaaaaagg gaataagggc gacacggaaa tgttgaatac tcatactctt ccttttttcaa    6060 tattattgaa gcatttatca gggttattgt ctcatgagcg gatacatatt tgaatgtatt    6120
tagaaaaata acaaataggg gttccgcgc acatttcccc gaaaagtgcc acctgacgtc    6180
taagaaacca ttattatcat gacattaacc tataaaaata ggcgtatcac gaggcccttt    6240
cgtc                                                                 6244
```

<210> SEQ ID NO 6
<211> LENGTH: 6216
<212> TYPE: DNA
<213> ORGANISM: Artificial Sequence
<220> FEATURE:
<223> OTHER INFORMATION: Sequence of pG180.

<400> SEQUENCE: 6

```
tcgcgcgttt cggtgatgac ggtgaaaacc tctgacacat gcagctcccg gagacggtca      60
cagcttgtct gtaagcggat gccggagca gacaagcccg tcaggcgcg tcagcgggtg       120 ttggcgggtg tcgggctgg cttaactatg cggcatcaga gcagattgta ctgagagtgc      180
```

```
accatatatg cggtgtgaaa taccgcacag atgcgtaagg agaaaatacc gcatcaggcg    240
cctcctcaac ctgtatattc gtaaaccacg cccaatggga gctgtctcag gtttgttcct    300
gattggttac ggcgcgtttc gcatcattgt tgagtttttc cgccagcccg acgcgcagtt    360
taccggtgcc tgggtgcagt acatcagcat ggggcaaatt ctttccatcc cgatgattgt    420
cgcgggtgtg atcatgatgg tctgggcata tcgtcgcagc ccacagcaac acgtttcctg    480
aggaaccatg aaacagtatt tagaactgat gcaaaaagtg ctcgacgaag gcacacagaa    540
aaacgaccgt accggaaccg gaacgctttc cattttggt catcagatgc gttttaacct     600
gcaagatgga ttcccgctgg tgacaactaa acgttgccac ctgcgttcca tcatccatga    660
actgctgtgg tttctgcagg gcgacactaa cattgcttat ctacacgaaa acaatgtcac    720
catctgggac gaatgggccg atgaaaacgg cgacctcggg ccagtgtatg gtaaacagtg    780
gcgcgcctgg ccaacgccag atggtcgtca tattgaccag atcactacgg tactgaacca    840
gctgaaaaac gacccggatt cgcgccgcat tattgtttca gcgtggaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta acccgaatc    1200 catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggttttttt accctccgtt aaattcttcg agacgccttc ccgaaggcgc cattcgccat   1380
tcaggctgcg caactgttgg aagggcgat cggtgcgggc ctcttcgcta ttacgccagc    1440
tggcgaaagg gggatgtgct gcaaggcgat taagttgggt aacgccaggg ttttcccagt   1500
cacgacgttg taaaacgacg gccagtgcca agctttcttt aatgaagcag ggcatcagga   1560
cggtatcttt gtggagaaag cagagtaatc ttattcagcc tgactggtgg gaaaccacca   1620
gtcagaatgt gttagcgcat gttgacaaaa ataccattag tcacattatc cgtcagtcgg   1680
acgacatggt agataacctg tttattatgc gttttgatct tacgtttaat attaccttta   1740
tgcgatgaaa cggtcttggc tttgatattc atttggtcag agatttgaat ggttccctga   1800
cctgccatcc acattcgcaa catactcgat tcggttcggc tcaatgataa cgtcggcata   1860
tttaaaaacg aggttatcgt tgtctctttt ttcagaatat cgccaaggat atcgtcgaga   1920
gattccggtt taatcgattt agaactgatc aataaatttt ttctgaccaa tagatattca   1980
tcaaaatgaa cattggcaat tgccataaaa acgataaata acgtattggg atgttgatta   2040
atgatgagct tgatacgctg actgttagaa gcatcgtgga tgaaacagtc ctcattaata   2100
aacaccactg aagggcgctg tgaatcacaa gctatgcaa ggtcatcaac ggtttcaatg    2160
tcgttgattt ctcttttttt aaccccctcta ctcaacagat accggttaa acctagtcgg   2220 gtgtaactac ataaatccat aataatcgtt gacatggcat accctcactc aatgcgtaac   2280
gataattccc cttacctgaa tatttcatca tgactaaacg gaacaacatg ggtcacctaa   2340
tgcgccactc tcgcgatttt tcaggcggac ttactatccc gtaaagtgtt gtataatttg   2400
cctggaattg tcttaaagta aagtaaatgt tgcgatatgt gagtgagctt aaaacaaata   2460
tttcgctgca ggagtatcct ggaagatgtt cgtagaagct tactgctcac aagaaaaaag   2520
```

```
gcacgtcatc tgacgtgcct tttttatttg tactaccctg tacgattact gcagctcgag    2580
tttaattcaa atcttcttca gaaatcaatt tttgttctct tacattcaat ttaaaccaag    2640
attctggtac agaatcctta tttataaaat tacctggagc aatcaccagc ttatcatcat    2700
atttcgaaag ccatgctccc caccagtaaa aagagctatt cgatattata taattacgaa    2760
aatgcatcat tagaaacata tcatctatag taccactatc atcctccttt ttacttatca    2820
aacgaacagg atattttccc gctagatgtt tttcaaccca ttctaaatct tgtgaaaaac    2880
aaaagaaaac aggagaagta acttttgatg ccataatatc catagcacat ttatagtaat    2940
catcttctaa cactccacca ggagctacat cactttcctg ataccgtcta accccaatca    3000
ttatggcatt cttatctagc aatttttatt cttccaattc caaatacgat gtgtattcta    3060
attttttttg tattacaaag tcctctttta tctcttgttt ataatcaaga aaatattttt    3120
ctgactgcca atatccttcc agaaaagcat ttgtaatctt agaactaatt aaccttgatt    3180
caaagtgggg agggcgctct tcgcaaatat aacgatatga tggatgaagt atatgacaac    3240
ctaaattacg acttagcctt ctataataat tcccatatga aaaatcaaat gttaattttt    3300
tattttcagg caagtctaat gcaaaatatg ataataaaag tttccttttta taaacttcat    3360 catttgcaaa atcagtagtc aaattaaaag cgaatggtac attgtttctt aatgccatgg    3420
ccttcaccat agcgtaaata aacatttgat tccccaatcc tcctcgcaaa gatgatacaa    3480
tcatatgtat atctccttct tgtctagaat tctaaaaatt gattgaatgt atgcaaataa    3540
atgcatacac ataggtgtg gtttaatttg atgcccttt tcagggctgg aatgtgtaag    3600
agcggggtta tttatgctgt tgttttttg ttactcggga agggctttac ctcttccgca    3660
taaacgcttc catcagcgtt tatagttaaa aaatctttc ggaactggtt ttgcgcttac    3720
cccaaccaac aggggatttg ctgctttcca ttgagcctgt ttctctgcgc gacgttcgcg    3780
gcggcgtgtt tgtgcatcca tctggattct cctgtcagtt agctttggtg gtgtgtggca    3840
gttgtagtcc tgaacgaaaa ccccccgcga ttggcacatt ggcagctaat ccggaatcgc    3900
acttacggcc aatgcttcgt ttcgtatcac acaccccaaa gccttctgct ttgaatgctg    3960
cccttcttca gggcttaatt tttaagagcg tcaccttcat ggtggtcagt gcgtcctgct    4020
gatgtgctca gtatcaccgc cagtggtatt tatgtcaaca ccgccagaga taatttatca    4080
ccgcagatgg ttatctgtat gttttttata tgaatttatt ttttgcaggg gggcattgtt    4140
tggtaggtga gagatcaatt ctgcattaat gaatcggcca acgcgcgggg agaggcggtt    4200
tgcgtattgg gcgctcttcc gcttcctcgc tcactgactc gctgcgctcg gtcgttcggc    4260
tgcggcgagc ggtatcagct cactcaaagg cggtaatacg ttatccaca gaatcagggg    4320 ataacgcagg aaagaacatg tgagcaaaag gccagcaaaa ggccaggaac cgtaaaaagg    4380
ccgcgttgct ggcgtttttc cataggctcc gcccccctga cgagcatcac aaaaatcgac    4440
gctcaagtca gaggtggcga aacccgacag gactataaag ataccaggcg tttccccctg    4500
gaagctccct cgtgcgctct cctgttccga ccctgccgct taccggatac ctgtccgcct    4560
ttctcccttc gggaagcgtg gcgctttctc atagctcacg ctgtaggtat ctcagttcgg    4620
tgtaggtcgt tcgctccaag ctgggctgtg tgcacgaacc ccccgttcag cccgaccgct    4680
gcgccttatc cggtaactat cgtcttgagt ccaacccggt aagacacgac ttatcgccac    4740
tggcagcagc cactggtaac aggattagca gagcgaggta tgtaggcggt gctacagagt    4800
tcttgaagtg gtggcctaac tacggctaca ctagaaggac agtatttggt atctgcgctc    4860
tgctgaagcc agttaccttc ggaaaaagag ttggtagctc ttgatccggc aaacaaacca    4920
```

```
ccgctggtag cggtggtttt tttgtttgca agcagcagat tacgcgcaga aaaaaaggat    4980
ctcaagaaga tcctttgatc ttttctacgg ggtctgacgc tcagtggaac gaaaactcac    5040
gttaagggat tttggtcatg agattatcaa aaaggatctt cacctagatc cttttaaatt    5100
aaaaatgaag ttttaaatca atctaaagta tatatgagta aacttggtct gacagttacc    5160
aatgcttaat cagtgaggca cctatctcag cgatctgtct atttcgttca tccatagttg    5220
cctgactccc cgtcgtgtag ataactacga tacgggaggg cttaccatct ggccccagtg    5280
ctgcaatgat accgcgagac ccacgctcac cggctccaga tttatcagca ataaaccagc    5340
cagccggaag ggccgagcgc agaagtggtc ctgcaacttt atccgcctcc atccagtcta    5400
ttaattgttg ccgggaagct agagtaagta gttcgccagt taatagtttg cgcaacgttg    5460
ttgccattgc tacaggcatc gtggtgtcac gctcgtcgtt tggtatggct tcattcagct    5520
ccggttccca acgatcaagg cgagttacat gatcccccat gttgtgcaaa aaagcggtta    5580
gctccttcgg tcctccgatc gttgtcagaa gtaagttggc cgcagtgtta tcactcatgg    5640
ttatggcagc actgcataat tctcttactg tcatgccatc cgtaagatgc ttttctgtga    5700
ctggtgagta ctcaaccaag tcattctgag aatagtgtat gcggcgaccg agttgctctt    5760
gcccggcgtc aatacgggat aataccgcgc cacatagcag aactttaaaa gtgctcatca    5820
ttggaaaacg ttcttcgggg cgaaaactct caaggatctt accgctgttg agatccagtt    5880
cgatgtaacc cactcgtgca cccaactgat cttcagcatc ttttactttc accagcgttt    5940
ctgggtgagc aaaaacagga aggcaaaatg ccgcaaaaaa gggaataagg gcgacacgga    6000
aatgttgaat actcatactc ttcctttttc aatattattg aagcatttat cagggttatt    6060
gtctcatgag cggatacata tttgaatgta tttagaaaaa taaacaaata ggggttccgc    6120
gcacatttcc ccgaaaagtg ccacctgacg tctaagaaac cattattatc atgacattaa    6180
cctataaaaa taggcgtatc acgaggccct ttcgtc                              6216

<210> SEQ ID NO 7
<211> LENGTH: 5049
<212> TYPE: DNA
<213> ORGANISM: Escherichia coli

<400> SEQUENCE: 7
gtccatggaa gacgtcgaaa aagtggttat cgacgagtcg gtaattgatg gtcaaagcaa      60
accgttgctg atttatggca agccggaagc gcaacaggca tctggtgaat aattaaccat     120
tcccatacaa ttagttaacc aaaaagggggg gattttatct ccccttaat ttttcctcta     180 ttctcggcgt tgaatgtggg ggaaacatcc ccatatactg acgtacatgt taatagatgg     240
cgtgaagcac agtcgtgtca tctgattacc tggcggaaat taaactaaga gagagctcta     300
tgattccggg gatccgtcga cctgcagttc gaagttccta ttctctagaa agtataggaa     360
cttcagagcg cttttgaagc tcacgctgcc gcaagcactc agggcgcaag gctgctaaa     420 ggaagcggaa cacgtagaaa gccagtccgc agaaacggtg ctgacccggg atgaatgtca     480
gctactgggc tatctggaca agggaaaacg caagcgcaaa gagaaagcag gtagcttgca     540
gtgggcttac atggcgatag ctagactggg cggttttatg acagcaagc gaaccggaat     600 tgccagctgg ggcgccctct ggtaaggttg gaagccctg caaagtaaac tggatggctt     660
tcttgccgcc aaggatctga tggcgcaggg gatcaagatc tgatcaagag acaggatgag     720
gatcgtttcg catgattgaa caagatggat tgcacgcagg ttctccggcc gcttgggtgg     780
```

| | |
|---|---|
| agaggctatt cggctatgac tgggcacaac agacaatcgg ctgctctgat gccgccgtgt | 840 |
| tccggctgtc agcgcagggg cgcccggttc tttttgtcaa gaccgacctg tccggtgccc | 900 |
| tgaatgaact gcaggacgag gcagcgcggc tatcgtggct ggccacgacg ggcgttcctt | 960 |
| gcgcagctgt gctcgacgtt gtcactgaag cgggaaggga ctggctgcta ttgggcgaag | 1020 |
| tgccggggca ggatctcctg tcatctcacc ttgctcctgc cgagaaagta tccatcatgg | 1080 |
| ctgatgcaat gcggcggctg catacgcttg atccggctac ctgcccattc gaccaccaag | 1140 |
| cgaaacatcg catcgagcga gcacgtactc ggatggaagc cggtcttgtc gatcaggatg | 1200 |
| atctggacga agagcatcag gggctcgcgc cagccgaact gttcgccagg ctcaaggcgc | 1260 |
| gcatgcccga cggcgaggat ctcgtcgtga cccatggcga tgcctgcttg ccgaatatca | 1320 |
| tggtggaaaa tggccgcttt tctggattca tcgactgtgg ccggctgggt gtggcggacc | 1380 |
| gctatcagga catagcgttg gctacccgtg atattgctga gagcttggc ggcgaatggg | 1440 |
| ctgaccgctt cctcgtgctt tacggtatcg ccgctcccga ttcgcagcgc atcgccttct | 1500 |
| atcgccttct tgacgagttc ttctaataag gggatcttga agttcctatt ccgaagttcc | 1560 |
| tattctctag aaagtatagg aacttcgaag cagctccagc ctacataaag cggccgctta | 1620 |
| ttttgacac cagaccaact ggtaatggta gcgaccggcg ctcagctgga attccgccga | 1680 |
| tactgacggg ctccaggagt cgtcgccacc aatccccata tggaaaccgt cgatattcag | 1740 |
| ccatgtgcct tcttccgcgt gcagcagatg gcgatggctg gtttccatca gttgctgttg | 1800 |
| actgtagcgg ctgatgttga actggaagtc gccgcgccac tggtgtgggc cataattcaa | 1860 |
| ttcgcgcgtc ccgcagcgca gaccgttttc gctcggaag acgtacgggg tatacatgtc | 1920 |
| tgacaatggc agatcccagc ggtcaaaaca ggcggcagta aggcggtcgg gatagttttc | 1980 |
| ttgcggccct aatccgagcc agtttacccg ctctgctacc tgcgccagct ggcagttcag | 2040 |
| gccaatccgc gccggatgcg gtgtatcgct cgccacttca acatcaacgg taatcgccat | 2100 |
| ttgaccacta ccatcaatcc ggtaggtttt ccggctgata aataaggttt tcccctgatg | 2160 |
| ctgccacgcg tgagcggtcg taatcagcac cgcatcagca agtgtatctg ccgtgcactg | 2220 |
| caacaacgct gcttcggcct ggtaatggcc cgccgcttc cagcgttcga cccaggcgtt | 2280 |
| agggtcaatg cgggtcgctt cacttacgcc aatgtcgtta ccagcggtg cacgggtgaa | 2340 |
| ctgatcgcgc agcggcgtca gcagttgttt tttatcgcca atccacatct gtgaaagaaa | 2400 |
| gcctgactgg cggttaaatt gccaacgctt attacccagc tcgatgcaaa aatccatttc | 2460 |
| gctggtggtc agatgcggga tggcgtggga cgcggcgggg agcgtcacac tgaggttttc | 2520 |
| cgccagacgc cactgctgcc aggcgctgat gtgcccggct tctgaccatg cggtcgcgtt | 2580 |
| cggttgcact acgcgtactg tgagccgag ttgcccggcg ctctccggct gcggtagttc | 2640 |
| aggcagttca atcaactgtt taccttgtgg agcgacatcc agaggcactt caccgcttgc | 2700 |
| cagcggctta ccatccagcg ccaccatcca gtgcaggagc tcgttatcgc tatgacggaa | 2760 |
| caggtattcg ctggtcactt cgatggtttg cccggataaa cggaactgga aaaactgctg | 2820 |
| ctggtgtttt gcttccgtca gcgctggatg cggcgtgcgg tcggcaaaga ccagaccgtt | 2880 |
| catacagaac tggcgatcgt tcggcgtatc gccaaaatca ccgccgtaag ccgaccacgg | 2940 |
| gttgccgttt tcatcatatt taatcagcga ctgatccacc cagtcccaga cgaagccgcc | 3000 |
| ctgtaaacgg ggatactgac gaaacgcctg ccagtattta gcgaaaccgc caagactgtt | 3060 |
| acccatcgcg tgggcgtatt cgcaaaggat cagcgggcgc gtctctccag gtagcgaaag | 3120 |
| ccatttttg atggaccatt tcggcacagc cgggaagggc tggtcttcat ccacgcgcgc | 3180 |

| | |
|---|---:|
| gtacatcggg caaataatat cggtggccgt ggtgtcggct ccgccgcctt catactgcac | 3240 |
| cgggcgggaa ggatcgacag atttgatcca gcgatacagc gcgtcgtgat tagcgccgtg | 3300 |
| gcctgattca ttccccagcg accagatgat cacactcggg tgattacgat cgcgctgcac | 3360 |
| cattcgcgtt acgcgttcgc tcatcgccgg tagccagcgc ggatcatcgg tcagacgatt | 3420 |
| cattggcacc atgccgtggg tttcaatatt ggcttcatcc accacataca ggccgtagcg | 3480 |
| gtcgcacagc gtgtaccaca gcggatggtt cggataatgc gaacagcgca cggcgttaaa | 3540 |
| gttgttctgc ttcatcagca ggatatcctg caccatcgtc tgctcatcca tgacctgacc | 3600 |
| atgcagagga tgatgctcgt gacgttaac gcctcgaatc agcaacggct tgccgttcag | 3660 |
| cagcagcaga ccattttcaa tccgcacctc gcggaaaccg acatcgcagg cttctgcttc | 3720 |
| aatcagcgtg ccgtcggcgg tgtgcagttc aaccaccgca cgatagagat tcgggatttc | 3780 |
| ggcgctccac agtttcgggt tttcgacgtt cagacgtagt gtgacgcgat cggcataacc | 3840 |
| accacgctca tcgataattt caccgccgaa aggcgcggtg ccgctggcga cctgcgtttc | 3900 |
| accctgccat aaagaaactg ttacccgtag gtagtcacgc aactcgccgc acatctgaac | 3960 |
| ttcagcctcc agtacagcgc ggctgaaatc atcattaaag cgagtggcaa catgaaaatc | 4020 |
| gctgatttgt gtagtcggtt tatgcagcaa cgagacgtca cggaaaatgc cgctcatccg | 4080 |
| ccacatatcc tgatcttcca gataactgcc gtcactccag cgcagcacca tcaccgcgag | 4140 |
| gcggttttct ccggcgcgta aaatgcgct caggtcaaat tcagacggca aacgactgtc | 4200 |
| ctggccgtaa ccgacccagc gcccgttgca ccacagatga aacgccgagt taacgccatc | 4260 |
| aaaaataatt cgcgtctggc cttcctgtag ccagctttca tcaacattaa atgtgagcga | 4320 |
| gtaacaaccc gtcggattct ccgtgggaac aaacggcgga ttgaccgtaa tgggataggt | 4380 |
| cacgttggtg tagatgggcg catcgtaacc gtgcatctgc cagtttgagg ggacgacgac | 4440 |
| agtatcggcc tcaggaagat cgcactccag ccagctttcc ggcaccgctt ctggtgccgg | 4500 |
| aaaccaggca agcgccatt cgccattcag gctgcgcaac tgttgggaag ggcgatcggt | 4560 |
| gcgggcctct tcgctattac gccagctggc gaaaggggga tgtgctgcaa ggcgattaag | 4620 |
| ttgggtaacg ccagggtttt cccagtcacg acgttgtaaa acgacggcca gtgaatccgt | 4680 |
| aatcatggtc atagtaggtt tcctcaggtt gtgactgcaa aatagtgacc tcgcgcaaaa | 4740 |
| tgcactaata aaaacagggc tggcaggcta attcgggctt gccagccttt ttttgtctcg | 4800 |
| ctaagttaga tggcggatcg ggcttgccct tattaagggg tgttgtaagg ggatggctgg | 4860 |
| cctgatataa ctgctgcgcg ttcgtacctt gaaggattca agtgcgatat aaattataaa | 4920 |
| gaggaagaga agagtgaata aatctcaatt gatcgacaag attgctgcag gggctgatat | 4980 |
| ctctaaagct gcggctggcc gtgcgttaga tgctattatt gcttccgtaa ctgaatctct | 5040 |
| gaaagaagg | 5049 |

<210> SEQ ID NO 8
<211> LENGTH: 6917
<212> TYPE: DNA
<213> ORGANISM: Artificial Sequence
<220> FEATURE:
<223> OTHER INFORMATION: Sequence of pG186.

<400> SEQUENCE: 8

| | |
|---|---:|
| tcgcgcgttt cggtgatgac ggtgaaaacc tctgacacat gcagctcccg gagacggtca | 60 |
| cagcttgtct gtaagcggat gccggagca gacaagcccg tcagggcgcg tcagcgggtg | 120 |

```
ttggcgggtg tcggggctgg cttaactatg cggcatcaga gcagattgta ctgagagtgc    180
accatatatg cggtgtgaaa taccgcacag atgcgtaagg agaaaatacc gcatcaggcg    240
cctcctcaac ctgtatattc gtaaaccacg cccaatggga gctgtctcag gtttgttcct    300
gattggttac ggcgcgtttc gcatcattgt tgagttttc cgccagcccg acgcgcagtt     360
taccggtgcc tgggtgcagt acatcagcat ggggcaaatt ctttccatcc cgatgattgt    420
cgcgggtgtg atcatgatgg tctgggcata tcgtcgcagc ccacagcaac acgtttcctg    480
aggaaccatg aaacagtatt tagaactgat gcaaaaagtg ctcgacgaag gcacacagaa    540
aaacgaccgt accggaaccg gaacgctttc cattttggt catcagatgc gttttaacct      600
gcaagatgga ttcccgctgg tgacaactaa acgttgccac ctgcgttcca tcatccatga    660
actgctgtgg tttctgcagg gcgacactaa cattgcttat ctacacgaaa acaatgtcac    720
catctgggac gaatgggccg atgaaaacgg cgacctcggg ccagtgtatg gtaaacagtg    780
gcgcgcctgg ccaacgccag atggtcgtca tattgaccag atcactacgg tactgaacca    840
gctgaaaaac gacccggatt cgcgccgcat tattgtttca gcgtgaaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta aacccgaatc   1200
catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggttttttt accctccgtt aaattcttcg agacgccttc ccgaaggcgc cattcgccat   1380
tcaggctgcg caactgttgg gaagggcgat cggtgcgggc ctcttcgcta ttacgccagc   1440
tggcgaaagg gggatgtgct gcaaggcgat taagttgggt aacgccaggg ttttcccagt   1500
cacgacgttg taaaacgacg gccagtgcca agctttcttt aatgaagcag ggcatcagga   1560
cggtatcttt gtggagaaag cagagtaatc ttattcagcc tgactggtgg aaaccacca    1620
gtcagaatgt gttagcgcat gttgacaaaa ataccattag tcacattatc cgtcagtcgg   1680
acgacatggt agataacctg tttattatgc gttttgatct tacgtttaat attacctta     1740
tgcgatgaaa cggtcttggc tttgatattc atttggtcag agatttgaat ggttccctga   1800
cctgccatcc acattcgcaa catactcgat tcggttcggc tcaatgataa cgtcggcata   1860
tttaaaaacg aggttatcgt tgtctctttt ttcagaatat cgccaaggat atcgtcgaga   1920
gattccggtt taatcgattt agaactgatc aataaatttt ttctgaccaa tagatattca   1980
tcaaaatgaa cattggcaat tgccataaaa acgataaata acgtattggg atgttgatta   2040
atgatgagct tgatacgctg actgttagaa gcatcgtgga tgaaacagtc ctcattaata   2100
aacaccactg aagggcgctg tgaatcacaa gctatggcaa ggtcatcaac ggtttcaatg   2160
tcgttgattt ctcttttttt aacccctcta ctcaacagat acccggttaa acctagtcgg   2220
gtgtaactac ataaatccat aataatcgtt gacatggcat accctcactc aatgcgtaac   2280
gataattccc cttacctgaa tatttcatca tgactaaacg gaacaacatg ggtcacctaa   2340
tgcgccactc tcgcgatttt tcaggcggac ttactatccc gtaaagtgtt gtataatttg   2400
cctggaattc tcttaaagta aagtaaatgt tgcgatatgt gagtgagctt aaaacaaata   2460
tttcgctgca ggagtatcct ggaagatgtt cgtagaagct tactgctcac aagaaaaaag   2520
```

```
gcacgtcatc tgacgtgcct tttttatttg tactaccctg tacgattact gcagctcgag    2580
ttagtcttta tctgccggac ttaaggtcac tgaagagaga taattcagca gggcgatatc    2640
gttctcgaca cccagcttca tcatcgcaga tttcttctgg ctactgatgg ttttaatact    2700
gcggttcagc ttttagcga tctcggtcac caggaagcct tccgcaaaca ggcgcagaac    2760
ttcactctct tttggcgaga gacgcttgtc accgtaacca ccagcactga ttttttccaa    2820
caggcgagaa acgctttccg gggtaaattt cttcccttc tgcagcgcgg cgagagcttt     2880
cggcagatcg gtcggtgcac cttgtttcag cacgatccct tcgatatcca gatccaatac    2940
cgcactaaga atcgccgggt tgttgttcat agtcagaaca atgatcgaca ggcttgggaa    3000
atggcgcttg atgtacttga ttaaggtaat gccatcgccg tacttatcgc caggcatgga    3060
gagatcggta atcaacacat gcgcatccag tttcggcagg ttgttgatca gtgctgtaga    3120
gtcttcaaat tcgccgacaa cattcaccca ctcaatttgc tcaagtgatt gcgaatacc    3180 gaacaagact atcggatggt catcggcaat aattacgttc atattgttca ttgtatatct    3240
ccttcttctc gagtttaatt caaatcttct tcagaaatca attttgttc agcgttatac     3300 ttttgggatt ttacctcaaa atgggattct attttcaccc actccttaca aaggatattc    3360
tcatgcccaa aaagccagtg tttggggcca ataatgattt tttctggatt ttctatcaaa    3420
taggccgccc accagctata agtgctatta gcgataatgc catgctgaca agattgcatg    3480
agcagcatgt cccaatacgc ctcttcttct ttatccctag tggtcatgtc cataaaggg    3540 tagccaagat caagattttg cgtgaattct aagtcttcgc aaaacacaaa aagctccatg    3600
tttggcacgc gctttgccat atactcaagc gcctttttt gatagtcaat accaagctga     3660
cagccaatcc ccacataatc ccctcttctt atatgcacaa acacgctgtt tttagcggct    3720
aaaatcaaag aaagcttgca ctgatattct tcctcttttt tattattatt cttattattt    3780
tcgggtggtg gtggtagagt gaaggtttgc ttgattaaag gggatatagc atcaaagtat    3840
cgtggatctt ggaaatagcc aaaaaaataa gtcaagcggc ttggctttag caatttaggc    3900
tcgtattcaa aaacgatttc ttgactcacc ctatcaaatc ccatgcattt gagcgcgtct    3960
cttactagct tggggaggtg ttgcattta gctatagcga tttctttcgc gctcgcatag     4020
ggcaaatcaa tagggaaaag ttctaattgc attttcctat cgctccaatc aaaagaagtg    4080
atatctaaca gcacaggcgt attagagtgt ttttgcaaac ttttagcgaa agcgtattga    4140
aacatttgat tcccaagccc tccgcaaatt tgcaccacct taaaagccat atgtatatct    4200
ccttcttgaa ttctaaaaat tgattgaatg tatgcaaata aatgcataca ccataggtgt    4260
ggtttaattt gatgcccttt ttcagggctg gaatgtgtaa gagcggggtt atttatgctg    4320
ttgttttttt gttactcggg aagggcttta cctcttccgc ataaacgctt ccatcagcgt    4380
ttatagttaa aaaaatcttt cggaactggt tttgcgctta ccccaaccaa caggggattt    4440 gctgcttttcc attgagcctg tttctctgcg cgacgttcgc ggcggcgtgt ttgtgcatcc    4500
atctggattc tcctgtcagt tagctttggt ggtgtgtggc agttgtagtc ctgaacgaaa    4560
accccccgcg attggcacat tggcagctaa tccggaatcg cacttacggc caatgcttcg    4620
tttcgtatca cacaccccaa agccttctgc tttgaatgct gcccttcttc agggcttaat    4680
ttttaagagc gtcaccttca tggtggtcag tgcgtcctgc tgatgtgctc agtatcaccg    4740
ccagtggtat ttagtgtcaac accgccgagag ataattatc accgcagatg gttatctgta    4800
tgttttttat atgaatttat ttttgcagg ggggcattgt ttggtaggtg agagatcaat     4860
```

```
tctgcattaa tgaatcggcc aacgcgcggg gagaggcggt tgcgtattg ggcgctcttc    4920
cgcttcctcg ctcactgact cgctgcgctc ggtcgttcgg ctgcggcgag cggtatcagc    4980
tcactcaaag gcggtaatac ggttatccac agaatcaggg gataacgcag gaaagaacat    5040
gtgagcaaaa ggccagcaaa aggccaggaa ccgtaaaaag gccgcgttgc tggcgttttt    5100
ccataggctc cgcccccctg acgagcatca aaaaatcga cgctcaagtc agaggtggcg    5160
aaacccgaca ggactataaa gataccaggc gtttccccct ggaagctccc tcgtgcgctc    5220
tcctgttccg accctgccgc ttaccggata cctgtccgcc tttctccctt cgggaagcgt    5280
ggcgctttct catagctcac gctgtaggta tctcagttcg gtgtaggtcg ttcgctccaa    5340
gctgggctgt gtgcacgaac cccccgttca gcccgaccgc tgcgccttat ccggtaacta    5400
tcgtcttgag tccaacccgg taagacacga cttatcgcca ctggcagcag ccactggtaa    5460
caggattagc agagcgaggt atgtaggcgg tgctacagag ttcttgaagt ggtggcctaa    5520
ctacggctac actagaagga cagtatttgg tatctgcgct ctgctgaagc cagttacctt    5580
cggaaaaaga gttggtagct cttgatccgg caaacaaacc accgctggta gcggtggttt    5640
ttttgtttgc aagcagcaga ttacgcgcag aaaaaaagga tctcaagaag atcctttgat    5700
cttttctacg gggtctgacg ctcagtggaa cgaaaactca cgttaaggga ttttggtcat    5760
gagattatca aaaaggatct tcacctagat ccttttaaat taaaaatgaa gttttaaatc    5820
aatctaaagt atatatgagt aaacttggtc tgacagttac caatgcttaa tcagtgaggc    5880
acctatctca gcgatctgtc tatttcgttc atccatagtt gcctgactcc ccgtcgtgta    5940
gataactacg atacgggagg gcttaccatc tggccccagt gctgcaatga taccgcgaga    6000
cccacgctca ccggctccag atttatcagc aataaaccag ccagccggaa gggccgagcg    6060
cagaagtggt cctgcaactt tatccgcctc catccagtct attaattgtt gccgggaagc    6120
tagagtaagt agttcgccag ttaatagttt gcgcaacgtt gttgccattg ctacaggcat    6180
cgtggtgtca cgctcgtcgt ttggtatggc ttcattcagc tccggttccc aacgatcaag    6240
gcgagttaca tgatccccca tgttgtgcaa aaaagcggtt agctccttcg gtcctccgat    6300
cgttgtcaga agtaagttgg ccgcagtgtt atcactcatg gttatggcag cactgcataa    6360
ttctcttact gtcatgccat ccgtaagatg cttttctgtg actggtgagt actcaaccaa    6420
gtcattctga gaatagtgta tgcggcgacc gagttgctct tgcccggcgt caatacggga    6480
taataccgcg ccacatagca gaactttaaa agtgctcatc attggaaaac gttcttcggg    6540
gcgaaaactc tcaaggatct taccgctgtt gagatccagt tcgatgtaac ccactcgtgc    6600
acccaactga tcttcagcat cttttacttt caccagcgtt tctgggtgag caaaaacagg    6660
aaggcaaaat gccgcaaaaa agggaataag ggcgacacgg aaatgttgaa tactcatact    6720
cttccttttt caatattatt gaagcattta tcagggttat tgtctcatga gcggatacat    6780
atttgaatgt atttagaaaa ataaacaaat aggggttccg cgcacatttc cccgaaaagt    6840
gccacctgac gtctaagaaa ccattattat catgacatta acctataaaa ataggcgtat    6900
cacgaggccc tttcgtc                                                  6917
```

<210> SEQ ID NO 9
<211> LENGTH: 424
<212> TYPE: PRT
<213> ORGANISM: Escherichia coli

<400> SEQUENCE: 9

Met Thr Asp Lys Arg Lys Asp Gly Ser Gly Lys Leu Leu Tyr Cys Ser

```
1               5                    10                   15
    Phe Cys Gly Lys Ser Gln His Glu Val Arg Lys Leu Ile Ala Gly Pro
                    20                   25                  30

Ser Val Tyr Ile Cys Asp Glu Cys Val Asp Leu Cys Asn Asp Ile Ile
                    35                   40                  45

Arg Glu Glu Ile Lys Glu Val Ala Pro His Arg Glu Arg Ser Ala Leu
                    50                   55                  60

Pro Thr Pro His Glu Ile Arg Asn His Leu Asp Asp Tyr Val Ile Gly
    65                   70                   75                  80

Gln Glu Gln Ala Lys Lys Val Leu Ala Val Ala Val Tyr Asn His Tyr
                        85                   90                  95

Lys Arg Leu Arg Asn Gly Asp Thr Ser Asn Gly Val Glu Leu Gly Lys
                        100                  105                 110

Ser Asn Ile Leu Leu Ile Gly Pro Thr Gly Ser Gly Lys Thr Leu Leu
                        115                  120                 125

Ala Glu Thr Leu Ala Arg Leu Leu Asp Val Pro Phe Thr Met Ala Asp
                        130                  135                 140

Ala Thr Thr Leu Thr Glu Ala Gly Tyr Val Gly Glu Asp Val Glu Asn
    145                  150                  155                 160

Ile Ile Gln Lys Leu Leu Gln Lys Cys Asp Tyr Asp Val Gln Lys Ala
                        165                  170                 175

Gln Arg Gly Ile Val Tyr Ile Asp Glu Ile Asp Lys Ile Ser Arg Lys
                        180                  185                 190

Ser Asp Asn Pro Ser Ile Thr Arg Asp Val Ser Gly Glu Gly Val Gln
                        195                  200                 205

Gln Ala Leu Leu Lys Leu Ile Glu Gly Thr Val Ala Ala Val Pro Pro
                        210                  215                 220

Gln Gly Gly Arg Lys His Pro Gln Gln Glu Phe Leu Gln Val Asp Thr
    225                  230                  235                 240

Ser Lys Ile Leu Phe Ile Cys Gly Gly Ala Phe Ala Gly Leu Asp Lys
                        245                  250                 255

Val Ile Ser His Arg Val Glu Thr Gly Ser Gly Ile Gly Phe Gly Ala
                        260                  265                 270

Thr Val Lys Ala Lys Ser Asp Lys Ala Ser Glu Gly Glu Leu Leu Ala
                        275                  280                 285

Gln Val Glu Pro Glu Asp Leu Ile Lys Phe Gly Leu Ile Pro Glu Phe
                        290                  295                 300

Ile Gly Arg Leu Pro Val Val Ala Thr Leu Asn Glu Leu Ser Glu Glu
    305                  310                  315                 320

Ala Leu Ile Gln Ile Leu Lys Glu Pro Lys Asn Ala Leu Thr Lys Gln
                        325                  330                 335

Tyr Gln Ala Leu Phe Asn Leu Glu Gly Val Asp Leu Glu Phe Arg Asp
                        340                  345                 350

Glu Ala Leu Asp Ala Ile Ala Lys Lys Ala Met Ala Arg Lys Thr Gly
                        355                  360                 365

Ala Arg Gly Leu Arg Ser Ile Val Glu Ala Ala Leu Leu Asp Thr Met
                        370                  375                 380

Tyr Asp Leu Pro Ser Met Glu Asp Val Glu Lys Val Val Ile Asp Glu
    385                  390                  395                 400

Ser Val Ile Asp Gly Gln Ser Lys Pro Leu Leu Ile Tyr Gly Lys Pro
                        405                  410                 415

Glu Ala Gln Gln Ala Ser Gly Glu
                        420
```

<210> SEQ ID NO 10
<211> LENGTH: 784
<212> TYPE: PRT
<213> ORGANISM: Escherichia coli

<400> SEQUENCE: 10

Met Asn Pro Glu Arg Ser Glu Arg Ile Glu Ile Pro Val Leu Pro Leu
1               5                   10                  15

Arg Asp Val Val Val Tyr Pro His Met Val Ile Pro Leu Phe Val Gly
                20                  25                  30

Arg Glu Lys Ser Ile Arg Cys Leu Glu Ala Ala Met Asp His Asp Lys
            35                  40                  45

Lys Ile Met Leu Val Ala Gln Lys Glu Ala Ser Thr Asp Glu Pro Gly
        50                  55                  60

Val Asn Asp Leu Phe Thr Val Gly Thr Val Ala Ser Ile Leu Gln Met
65                  70                  75                  80

Leu Lys Leu Pro Asp Gly Thr Val Lys Val Leu Val Glu Gly Leu Gln
                85                  90                  95

Arg Ala Arg Ile Ser Ala Leu Ser Asp Asn Gly Glu His Phe Ser Ala
            100                 105                 110

Lys Ala Glu Tyr Leu Glu Ser Pro Thr Ile Asp Glu Arg Glu Gln Glu
        115                 120                 125

Val Leu Val Arg Thr Ala Ile Ser Gln Phe Glu Gly Tyr Ile Lys Leu
    130                 135                 140

Asn Lys Lys Ile Pro Pro Glu Val Leu Thr Ser Leu Asn Ser Ile Asp
145                 150                 155                 160

Asp Pro Ala Arg Leu Ala Asp Thr Ile Ala Ala His Met Pro Leu Lys
                165                 170                 175

Leu Ala Asp Lys Gln Ser Val Leu Glu Met Ser Asp Val Asn Glu Arg
            180                 185                 190

Leu Glu Tyr Leu Met Ala Met Met Glu Ser Glu Ile Asp Leu Leu Gln
        195                 200                 205

Val Glu Lys Arg Ile Arg Asn Arg Val Lys Lys Gln Met Glu Lys Ser
    210                 215                 220

Gln Arg Glu Tyr Tyr Leu Asn Glu Gln Met Lys Ala Ile Gln Lys Glu
225                 230                 235                 240

Leu Gly Glu Met Asp Asp Ala Pro Asp Glu Asn Glu Ala Leu Lys Arg
                245                 250                 255

Lys Ile Asp Ala Ala Lys Met Pro Lys Glu Ala Lys Glu Lys Ala Glu
            260                 265                 270

Ala Glu Leu Gln Lys Leu Lys Met Met Ser Pro Met Ser Ala Glu Ala
        275                 280                 285

Thr Val Val Arg Gly Tyr Ile Asp Trp Met Val Gln Val Pro Trp Asn
    290                 295                 300

Ala Arg Ser Lys Val Lys Lys Asp Leu Arg Gln Ala Gln Glu Ile Leu
305                 310                 315                 320

Asp Thr Asp His Tyr Gly Leu Glu Arg Val Lys Asp Arg Ile Leu Glu
                325                 330                 335

Tyr Leu Ala Val Gln Ser Arg Val Asn Lys Ile Lys Gly Pro Ile Leu
            340                 345                 350

Cys Leu Val Gly Pro Pro Gly Val Gly Lys Thr Ser Leu Gly Gln Ser
        355                 360                 365

Ile Ala Lys Ala Thr Gly Arg Lys Tyr Val Arg Met Ala Leu Gly Gly

```
                370                 375                 380
Val Arg Asp Glu Ala Glu Ile Arg Gly His Arg Arg Thr Tyr Ile Gly
385                 390                 395                 400

Ser Met Pro Gly Lys Leu Ile Gln Lys Met Ala Lys Val Gly Val Lys
                405                 410                 415

Asn Pro Leu Phe Leu Leu Asp Glu Ile Asp Lys Met Ser Ser Asp Met
                420                 425                 430

Arg Gly Asp Pro Ala Ser Ala Leu Leu Glu Val Leu Asp Pro Glu Gln
                435                 440                 445

Asn Val Ala Phe Ser Asp His Tyr Leu Glu Val Asp Tyr Asp Leu Ser
            450                 455                 460

Asp Val Met Phe Val Ala Thr Ser Asn Ser Met Asn Ile Pro Ala Pro
465                 470                 475                 480

Leu Leu Asp Arg Met Glu Val Ile Arg Leu Ser Gly Tyr Thr Glu Asp
                485                 490                 495

Glu Lys Leu Asn Ile Ala Lys Arg His Leu Leu Pro Lys Gln Ile Glu
                500                 505                 510

Arg Asn Ala Leu Lys Lys Gly Glu Leu Thr Val Asp Asp Ser Ala Ile
            515                 520                 525

Ile Gly Ile Ile Arg Tyr Tyr Thr Arg Glu Ala Gly Val Arg Gly Leu
530                 535                 540

Glu Arg Glu Ile Ser Lys Leu Cys Arg Lys Ala Val Lys Gln Leu Leu
545                 550                 555                 560

Leu Asp Lys Ser Leu Lys His Ile Glu Ile Asn Gly Asp Asn Leu His
                565                 570                 575

Asp Tyr Leu Gly Val Gln Arg Phe Asp Tyr Gly Arg Ala Asp Asn Glu
            580                 585                 590

Asn Arg Val Gly Gln Val Thr Gly Leu Ala Trp Thr Glu Val Gly Gly
            595                 600                 605

Asp Leu Leu Thr Ile Glu Thr Ala Cys Val Pro Gly Lys Gly Lys Leu
            610                 615                 620

Thr Tyr Thr Gly Ser Leu Gly Glu Val Met Gln Glu Ser Ile Gln Ala
625                 630                 635                 640

Ala Leu Thr Val Val Arg Ala Arg Ala Glu Lys Leu Gly Ile Asn Pro
                645                 650                 655

Asp Phe Tyr Glu Lys Arg Asp Ile His Val His Val Pro Glu Gly Ala
                660                 665                 670

Thr Pro Lys Asp Gly Pro Ser Ala Gly Ile Ala Met Cys Thr Ala Leu
                675                 680                 685

Val Ser Cys Leu Thr Gly Asn Pro Val Arg Ala Asp Val Ala Met Thr
            690                 695                 700

Gly Glu Ile Thr Leu Arg Gly Gln Val Leu Pro Ile Gly Gly Leu Lys
705                 710                 715                 720

Glu Lys Leu Leu Ala Ala His Arg Gly Gly Ile Lys Thr Val Leu Ile
                725                 730                 735

Pro Phe Glu Asn Lys Arg Asp Leu Glu Glu Ile Pro Asp Asn Val Ile
                740                 745                 750

Ala Asp Leu Asp Ile His Pro Val Lys Arg Ile Glu Glu Val Leu Thr
                755                 760                 765

Leu Ala Leu Gln Asn Glu Pro Ser Gly Met Gln Val Val Thr Ala Lys
            770                 775                 780

<210> SEQ ID NO 11
```

<211> LENGTH: 264
<212> TYPE: PRT
<213> ORGANISM: Escherichia coli

<400> SEQUENCE: 11

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 12
<211> LENGTH: 1024
<212> TYPE: PRT
<213> ORGANISM: Escherichia coli

<400> SEQUENCE: 12

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80
```

```
Glu Ala Asp Thr Val Val Pro Ser Asn Trp Gln Met His Gly Tyr
             85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
    370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
        435                 440                 445

Arg Asn His Pro Ser Val Ile Ile Trp Ser Leu Gly Asn Glu Ser Gly
    450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495
```

```
Thr Asp Ile Ile Cys Pro Met Tyr Ala Arg Val Asp Glu Asp Gln Pro
                500                 505                 510
Phe Pro Ala Val Pro Lys Trp Ser Ile Lys Trp Leu Ser Leu Pro
            515                 520                 525
Gly Glu Thr Arg Pro Leu Ile Leu Cys Glu Tyr Ala His Ala Met Gly
        530                 535                 540
Asn Ser Leu Gly Gly Phe Ala Lys Tyr Trp Gln Ala Phe Arg Gln Tyr
545                 550                 555                 560
Pro Arg Leu Gln Gly Gly Phe Val Trp Asp Trp Val Asp Gln Ser Leu
                565                 570                 575
Ile Lys Tyr Asp Glu Asn Gly Asn Pro Trp Ser Ala Tyr Gly Gly Asp
            580                 585                 590
Phe Gly Asp Thr Pro Asn Asp Arg Gln Phe Cys Met Asn Gly Leu Val
        595                 600                 605
Phe Ala Asp Arg Thr Pro His Pro Ala Leu Thr Glu Ala Lys His Gln
        610                 615                 620
Gln Gln Phe Phe Gln Phe Arg Leu Ser Gly Gln Thr Ile Glu Val Thr
625                 630                 635                 640
Ser Glu Tyr Leu Phe Arg His Ser Asp Asn Glu Leu Leu His Trp Met
                645                 650                 655
Val Ala Leu Asp Gly Lys Pro Leu Ala Ser Gly Glu Val Pro Leu Asp
            660                 665                 670
Val Ala Pro Gln Gly Lys Gln Leu Ile Glu Leu Pro Glu Leu Pro Gln
        675                 680                 685
Pro Glu Ser Ala Gly Gln Leu Trp Leu Thr Val Arg Val Val Gln Pro
        690                 695                 700
Asn Ala Thr Ala Trp Ser Glu Ala Gly His Ile Ser Ala Trp Gln Gln
705                 710                 715                 720
Trp Arg Leu Ala Glu Asn Leu Ser Val Thr Leu Pro Ala Ala Ser His
                725                 730                 735
Ala Ile Pro His Leu Thr Thr Ser Glu Met Asp Phe Cys Ile Glu Leu
            740                 745                 750
Gly Asn Lys Arg Trp Gln Phe Asn Arg Gln Ser Gly Phe Leu Ser Gln
        755                 760                 765
Met Trp Ile Gly Asp Lys Lys Gln Leu Leu Thr Pro Leu Arg Asp Gln
770                 775                 780
Phe Thr Arg Ala Pro Leu Asp Asn Asp Ile Gly Val Ser Glu Ala Thr
785                 790                 795                 800
Arg Ile Asp Pro Asn Ala Trp Val Glu Arg Trp Lys Ala Ala Gly His
                805                 810                 815
Tyr Gln Ala Glu Ala Ala Leu Leu Gln Cys Thr Ala Asp Thr Leu Ala
            820                 825                 830
Asp Ala Val Leu Ile Thr Thr Ala His Ala Trp Gln His Gln Gly Lys
        835                 840                 845
Thr Leu Phe Ile Ser Arg Lys Thr Tyr Arg Ile Asp Gly Ser Gly Gln
        850                 855                 860
Met Ala Ile Thr Val Asp Val Glu Val Ala Ser Asp Thr Pro His Pro
865                 870                 875                 880
Ala Arg Ile Gly Leu Asn Cys Gln Leu Ala Gln Val Ala Glu Arg Val
                885                 890                 895
Asn Trp Leu Gly Leu Gly Pro Gln Glu Asn Tyr Pro Asp Arg Leu Thr
            900                 905                 910
Ala Ala Cys Phe Asp Arg Trp Asp Leu Pro Leu Ser Asp Met Tyr Thr
```

-continued

```
                915                 920                 925

Pro Tyr Val Phe Pro Ser Glu Asn Gly Leu Arg Cys Gly Thr Arg Glu
    930                 935                 940

Leu Asn Tyr Gly Pro His Gln Trp Arg Gly Asp Phe Gln Phe Asn Ile
945                 950                 955                 960

Ser Arg Tyr Ser Gln Gln Leu Met Glu Thr Ser His Arg His Leu
            965                 970                 975

Leu His Ala Glu Glu Gly Thr Trp Leu Asn Ile Asp Gly Phe His Met
                980                 985                 990

Gly Ile Gly Gly Asp Asp Ser Trp Ser Pro Ser Val Ser Ala Glu Phe
                995                 1000                1005

Gln Leu Ser Ala Gly Arg Tyr His Tyr Gln Leu Val Trp Cys Gln
    1010                1015                1020

Lys
```

<210> SEQ ID NO 13
<211> LENGTH: 784
<212> TYPE: PRT
<213> ORGANISM: Escherichia coli

<400> SEQUENCE: 13

```
Met Asn Pro Glu Arg Ser Glu Arg Ile Glu Ile Pro Val Leu Pro Leu
1               5                   10                  15

Arg Asp Val Val Val Tyr Pro His Met Val Ile Pro Leu Phe Val Gly
                20                  25                  30

Arg Glu Lys Ser Ile Arg Cys Leu Glu Ala Ala Met Asp His Asp Lys
            35                  40                  45

Lys Ile Met Leu Val Ala Gln Lys Glu Ala Ser Thr Asp Glu Pro Gly
50                  55                  60

Val Asn Asp Leu Phe Thr Val Gly Thr Val Ala Ser Ile Leu Gln Met
65                  70                  75                  80

Leu Lys Leu Pro Asp Gly Thr Val Lys Val Leu Val Glu Gly Leu Gln
                85                  90                  95

Arg Ala Arg Ile Ser Ala Leu Ser Asp Asn Gly Glu His Phe Ser Ala
            100                 105                 110

Lys Ala Glu Tyr Leu Glu Ser Pro Thr Ile Asp Glu Arg Glu Gln Glu
        115                 120                 125

Val Leu Val Arg Thr Ala Ile Ser Gln Phe Glu Gly Tyr Ile Lys Leu
    130                 135                 140

Asn Lys Lys Ile Pro Pro Glu Val Leu Thr Ser Leu Asn Ser Ile Asp
145                 150                 155                 160

Asp Pro Ala Arg Leu Ala Asp Thr Ile Ala Ala His Met Pro Leu Lys
                165                 170                 175

Leu Ala Asp Lys Gln Ser Val Leu Glu Met Ser Asp Val Asn Glu Arg
            180                 185                 190

Leu Glu Tyr Leu Met Ala Met Met Glu Ser Glu Ile Asp Leu Leu Gln
        195                 200                 205

Val Glu Lys Arg Ile Arg Asn Arg Val Lys Lys Gln Met Glu Lys Ser
    210                 215                 220

Gln Arg Glu Tyr Tyr Leu Asn Glu Gln Met Lys Ala Ile Gln Lys Glu
225                 230                 235                 240

Leu Gly Glu Met Asp Asp Ala Pro Asp Glu Asn Glu Ala Leu Lys Arg
                245                 250                 255

Lys Ile Asp Ala Ala Lys Met Pro Lys Glu Ala Lys Glu Lys Ala Glu
```

-continued

```
            260                 265                 270
Ala Glu Leu Gln Lys Leu Lys Met Met Ser Pro Met Ser Ala Glu Ala
            275                 280                 285
Thr Val Val Arg Gly Tyr Ile Asp Trp Met Val Gln Val Pro Trp Asn
            290                 295                 300
Ala Arg Ser Lys Val Lys Lys Asp Leu Arg Gln Ala Gln Glu Ile Leu
305                 310                 315                 320
Asp Thr Asp His Tyr Gly Leu Glu Arg Val Lys Asp Arg Ile Leu Glu
                    325                 330                 335
Tyr Leu Ala Val Gln Ser Arg Val Asn Lys Ile Lys Gly Pro Ile Leu
                340                 345                 350
Cys Leu Val Gly Pro Pro Gly Val Gly Lys Thr Ser Leu Gly Gln Ser
                355                 360                 365
Ile Ala Lys Ala Thr Gly Arg Lys Tyr Val Arg Met Ala Leu Gly Gly
            370                 375                 380
Val Arg Asp Glu Ala Glu Ile Arg Gly His Arg Arg Thr Tyr Ile Gly
385                 390                 395                 400
Ser Met Pro Gly Lys Leu Ile Gln Lys Met Ala Lys Val Gly Val Lys
                    405                 410                 415
Asn Pro Leu Phe Leu Leu Asp Glu Ile Asp Lys Met Ser Ser Asp Met
                420                 425                 430
Arg Gly Asp Pro Ala Ser Ala Leu Leu Glu Val Leu Asp Pro Glu Gln
            435                 440                 445
Asn Val Ala Phe Ser Asp His Tyr Leu Glu Val Asp Tyr Asp Leu Ser
            450                 455                 460
Asp Val Met Phe Val Ala Thr Ser Asn Ser Met Asn Ile Pro Ala Pro
465                 470                 475                 480
Leu Leu Asp Arg Met Glu Val Ile Arg Leu Ser Gly Tyr Thr Glu Asp
                    485                 490                 495
Glu Lys Leu Asn Ile Ala Lys Arg His Leu Leu Pro Lys Gln Ile Glu
                500                 505                 510
Arg Asn Ala Leu Lys Lys Gly Glu Leu Thr Val Asp Asp Ser Ala Ile
            515                 520                 525
Ile Gly Ile Ile Arg Tyr Tyr Thr Arg Glu Ala Gly Val Arg Gly Leu
            530                 535                 540
Glu Arg Glu Ile Ser Lys Leu Cys Arg Lys Ala Val Lys Gln Leu Leu
545                 550                 555                 560
Leu Asp Lys Ser Leu Lys His Ile Glu Ile Asn Gly Asp Asn Leu His
                    565                 570                 575
Asp Tyr Leu Gly Val Gln Arg Phe Asp Tyr Gly Arg Ala Asp Asn Glu
                580                 585                 590
Asn Arg Val Gly Gln Val Thr Gly Leu Ala Trp Thr Glu Val Gly Gly
            595                 600                 605
Asp Leu Leu Thr Ile Glu Thr Ala Cys Val Pro Gly Lys Gly Lys Leu
            610                 615                 620
Thr Tyr Thr Gly Ser Leu Gly Glu Val Met Gln Glu Ser Ile Gln Ala
625                 630                 635                 640
Ala Leu Thr Val Val Arg Ala Arg Ala Glu Lys Leu Gly Ile Asn Pro
                    645                 650                 655
Asp Phe Tyr Glu Lys Arg Asp Ile His Val His Val Pro Glu Gly Ala
                660                 665                 670
Thr Pro Lys Asp Gly Pro Ser Ala Gly Ile Ala Met Cys Thr Ala Leu
            675                 680                 685
```

Val Ser Cys Leu Thr Gly Asn Pro Val Arg Ala Asp Val Ala Met Thr
    690                 695                 700

Gly Glu Ile Thr Leu Arg Gly Gln Val Leu Pro Ile Gly Gly Leu Lys
705                 710                 715                 720

Glu Lys Leu Leu Ala Ala His Arg Gly Gly Ile Lys Thr Val Leu Ile
                725                 730                 735

Pro Phe Glu Asn Lys Arg Asp Leu Glu Glu Ile Pro Asp Asn Val Ile
            740                 745                 750

Ala Asp Leu Asp Ile His Pro Val Lys Arg Ile Glu Glu Val Leu Thr
        755                 760                 765

Leu Ala Leu Gln Asn Glu Pro Ser Gly Met Gln Val Val Thr Ala Lys
    770                 775                 780

<210> SEQ ID NO 14
<211> LENGTH: 90
<212> TYPE: PRT
<213> ORGANISM: Escherichia coli

<400> SEQUENCE: 14

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
            20                  25                  30

Thr Glu Ser Leu Lys Glu Gly Asp Asp Val Ala Leu Val Gly Phe Gly
        35                  40                  45

Thr Phe Ala Val Lys Glu Arg Ala Ala Arg Thr Gly Arg Asn Pro Gln
    50                  55                  60

Thr Gly Lys Glu Ile Thr Ile Ala Ala Ala Lys Val Pro Ser Phe Arg
65                  70                  75                  80

Ala Gly Lys Ala Leu Lys Asp Ala Val Asn
                85                  90

<210> SEQ ID NO 15
<211> LENGTH: 5049
<212> TYPE: DNA
<213> ORGANISM: Escherichia coli

<400> SEQUENCE: 15
gtccatggaa gacgtcgaaa aagtggttat cgacgagtcg gtaattgatg gtcaaagcaa      60
accgttgctg atttatggca agccggaagc gcaacaggca tctggtgaat aattaaccat     120
tcccatacaa ttagttaacc aaaaaggggg gattttatct cccctttaat ttttcctcta     180
ttctcggcgt tgaatgtggg ggaaacatcc ccatatactg acgtacatgt taatagatgg     240
cgtgaagcac agtcgtgtca tctgattacc tggcggaaat taaactaaga gagagctcta     300
tgattccggg gatccgtcga cctgcagttc gaagttccta ttctctagaa agtataggaa     360
cttcagagcg cttttgaagc tcacgctgcc gcaagcactc agggcgcaag gctgctaaa      420 ggaagcggaa cacgtagaaa gccagtccgc agaaacggtg ctgaccccgg atgaatgtca     480
gctactgggc tatctggaca agggaaaacg caagcgcaaa gagaaagcag gtagcttgca     540
gtgggcttac atggcgatag ctagactggg cggttttatg acagcaagc gaaccggaat      600 tgccagctgg ggcgccctct ggtaaggttg ggaagccctg caaagtaaac tggatggctt     660
tcttgccgcc aaggatctga tggcgcaggg gatcaagatc tgatcaagag acaggatgag     720
gatcgtttcg catgattgaa caagatggat tgcacgcagg ttctccggcc gcttgggtgg     780

```
agaggctatt cggctatgac tgggcacaac agacaatcgg ctgctctgat gccgccgtgt    840
tccggctgtc agcgcagggg cgcccggttc tttttgtcaa gaccgacctg tccggtgccc    900
tgaatgaact gcaggacgag gcagcgcggc tatcgtggct ggccacgacg ggcgttcctt    960
gcgcagctgt gctcgacgtt gtcactgaag cgggaaggga ctggctgcta ttgggcgaag   1020
tgccggggca ggatctcctg tcatctcacc ttgctcctgc cgagaaagta tccatcatgg   1080
ctgatgcaat gcggcggctg catacgcttg atccggctac ctgcccattc gaccaccaag   1140
cgaaacatcg catcgagcga gcacgtactc ggatggaagc cggtcttgtc gatcaggatg   1200
atctggacga agagcatcag gggctcgcgc cagccgaact gttcgccagg ctcaaggcgc   1260
gcatgcccga cggcgaggat ctcgtcgtga cccatggcga tgcctgcttg ccgaatatca   1320
tggtggaaaa tggccgcttt tctggattca tcgactgtgg ccggctgggt gtggcggacc   1380
gctatcagga catagcgttg gctacccgtg atattgctga gagcttggc ggcgaatggg   1440 ctgaccgctt cctcgtgctt tacggtatcg ccgctcccga ttcgcagcgc atcgccttct   1500
atcgccttct tgacgagttc ttctaataag gggatcttga agttcctatt ccgaagttcc   1560
tattctctag aaagtatagg aacttcgaag cagctccagc ctacataaag cggccgctta   1620
tttttgacac cagaccaact ggtaatggta gcgaccggcg ctcagctgga attccgccga   1680
tactgacggg ctccaggagt cgtcgccacc aatccccata tggaaaccgt cgatattcag   1740
ccatgtgcct tcttccgcgt gcagcagatg gcgatggctg gtttccatca gttgctgttg   1800
actgtagcgg ctgatgttga actggaagtc gccgcgccac tggtgtgggc cataattcaa   1860
ttcgcgcgtc ccgcagcgca gaccgttttc gctcggaag acgtacgggg tatacatgtc   1920
tgacaatggc agatcccagc ggtcaaaaca ggcggcagta aggcggtcgg gatagttttc   1980
ttgcggccct aatccgagcc agtttacccg ctctgctacc tgcgccagct ggcagttcag   2040
gccaatccgc gccggatgcg gtgtatcgct cgccacttca acatcaacgg taatcgccat   2100
ttgaccacta ccatcaatcc ggtaggtttt ccggctgata aataaggttt tcccctgatg   2160
ctgccacgcg tgagcggtcg taatcagcac cgcatcagca agtgtatctg ccgtgcactg   2220
caacaacgct gcttcggcct ggtaatggcc cgccgcttc cagcgttcga cccaggcgtt   2280
agggtcaatg cgggtcgctt cacttacgcc aatgtcgtta tccagcggtg cacgggtgaa   2340
ctgatcgcgc agcggcgtca gcagttgttt tttatcgcca atccacatct gtgaaagaaa   2400
gcctgactgg cggttaaatt gccaacgctt attcccagc tcgatgcaaa aatccatttc   2460
gctggtggtc agatgcggga tggcgtggga cgcggcgggg agcgtcacac tgaggttttc   2520
cgccagacgc cactgctgcc aggcgctgat gtgcccggct tctgaccatg cggtcgcgtt   2580
cggttgcact acgcgtactg tgagccgagt tgcccggcg ctctccggct gcggtagttc   2640
aggcagttca atcaactgtt taccttgtgg agcgacatcc agaggcactt caccgcttgc   2700
cagcggctta ccatccagcg ccaccatcca gtgcaggagc tcgttatcgc tatgacggaa   2760
caggtattcg ctggtcactt cgatggtttg cccggataaa cggaactgga aaaactgctg   2820
ctggtgtttt gcttccgtca gcgctggatg cggcgtgcgg tcggcaaaga ccagaccgtt   2880
catacagaac tggcgatcgt tcggcgtatc gccaaaatca ccgccgtaag ccgaccacgg   2940
gttgccgttt tcatcatatt taatcagcga ctgatccacc cagtcccaga cgaagccgcc   3000
ctgtaaacgg ggatactgac gaaacgcctg ccagtattta gcgaaaccgc caagactgtt   3060
acccatcgcg tgggcgtatt cgcaaaggat cagcgggcgc gtctctccag gtagcgaaag   3120
ccattttttg atggaccatt tcggcacagc cgggaagggc tggtcttcat ccacgcgcgc   3180
```

```
gtacatcggg caaataatat cggtggccgt ggtgtcggct ccgccgcctt catactgcac    3240
cgggcgggaa ggatcgacag atttgatcca gcgatacagc gcgtcgtgat tagcgccgtg    3300
gcctgattca ttccccagcg accagatgat cacactcggg tgattacgat cgcgctgcac    3360
cattcgcgtt acgcgttcgc tcatcgccgg tagccagcgc ggatcatcgg tcagacgatt    3420
cattggcacc atgccgtggg tttcaatatt ggcttcatcc accacataca ggccgtagcg    3480
gtcgcacagc gtgtaccaca gcggatggtt cggataatgc gaacagcgca cggcgttaaa    3540
gttgttctgc ttcatcagca ggatatcctg caccatcgtc tgctcatcca tgacctgacc    3600
atgcagagga tgatgctcgt gacggttaac gcctcgaatc agcaacggct tgccgttcag    3660
cagcagcaga ccattttcaa tccgcacctc gcggaaaccg acatcgcagg cttctgcttc    3720
aatcagcgtg ccgtcggcgg tgtgcagttc aaccaccgca cgatagagat tcgggatttc    3780
ggcgctccac agtttcgggt tttcgacgtt cagacgtagt gtgacgcgat cggcataacc    3840
accacgctca tcgataattt caccgccgaa aggcgcggtg ccgctggcga cctgcgtttc    3900
accctgccat aaagaaactg ttacccgtag gtagtcacgc aactcgccgc acatctgaac    3960
ttcagcctcc agtacagcgc ggctgaaatc atcattaaag cgagtggcaa catggaaatc    4020
gctgatttgt gtagtcggtt tatgcagcaa cgagacgtca cggaaaatgc cgctcatccg    4080
ccacatatcc tgatcttcca gataactgcc gtcactccag cgcagcacca tcaccgcgag    4140
gcggttttct ccggcgcgta aaaatgcgct caggtcaaat tcagacggca aacgactgtc    4200
ctggccgtaa ccgacccagc gcccgttgca ccacagatga aacgccgagt taacgccatc    4260
aaaaataatt cgcgtctggc cttcctgtag ccagctttca tcaacattaa atgtgagcga    4320
gtaacaaccc gtcggattct ccgtgggaac aaacggcgga ttgaccgtaa tgggataggt    4380
cacgttggtg tagatgggcg catcgtaacc gtgcatctgc cagtttgagg ggacgacgac    4440
agtatcggcc tcaggaagat cgcactccag ccagctttcc ggcaccgctt ctggtgccgg    4500
aaaccaggca aagcgccatt cgccattcag gctgcgcaac tgttgggaag ggcgatcggt    4560
gcgggcctct tcgctattac gccagctggc gaaaggggga tgtgctgcaa ggcgattaag    4620
ttgggtaacg ccagggtttt cccagtcacg acgttgtaaa acgacggcca gtgaatccgt    4680
aatcatggtc atagtaggtt tcctcaggtt gtgactgcaa aatagtgacc tcgcgcaaaa    4740
tgcactaata aaaacagggc tggcaggcta attcgggctt gccagccttt ttttgtctcg    4800
ctaagttaga tggcggatcg ggcttgccct tattaagggg tgttgtaagg ggatggctgg    4860
cctgatataa ctgctgcgcg ttcgtacctt gaaggattca agtgcgatat aaattataaa    4920
gaggaagaga agagtgaata aatctcaatt gatcgacaag attgctgcag gggctgatat    4980
ctctaaagct gcggctggcc gtgcgttaga tgctattatt gcttccgtaa ctgaatctct    5040
gaaagaagg                                                            5049
```